US009883819B2

(12) United States Patent
Jensen et al.

(10) Patent No.: US 9,883,819 B2
(45) Date of Patent: Feb. 6, 2018

(54) INGESTION-RELATED BIOFEEDBACK AND PERSONALIZED MEDICAL THERAPY METHOD AND SYSTEM

(75) Inventors: Marc Jensen, Los Gatos, CA (US); Robert Leichner, Menlo Park, CA (US); Patrick Beaulieu, San Jose, CA (US); Kit Yee Au-Yeung, San Francisco, CA (US); Lawrence Arne, Palo Alto, CA (US); Mark Zdeblick, Portola Valley, CA (US); Andrew Thompson, Portola Valley, CA (US); George Savage, Portola Valley, CA (US); Timothy Robertson, Belmont, CA (US); Yashar Behzadi, San Francisco, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 13/141,048

(22) PCT Filed: Jan. 6, 2010

(86) PCT No.: PCT/US2010/020269
§ 371 (c)(1),
(2), (4) Date: Jun. 20, 2011

(87) PCT Pub. No.: WO2010/080843
PCT Pub. Date: Jul. 15, 2010

(65) Prior Publication Data
US 2011/0270052 A1    Nov. 3, 2011

Related U.S. Application Data

(60) Provisional application No. 61/142,869, filed on Jan. 6, 2009, provisional application No. 61/260,325, filed on Nov. 11, 2009.

(51) Int. Cl.
A61B 5/07    (2006.01)
A61B 5/00    (2006.01)
(Continued)

(52) U.S. Cl.
CPC ............ *A61B 5/073* (2013.01); *A61B 5/0002* (2013.01); *A61B 5/6833* (2013.01);
(Continued)

(58) Field of Classification Search
CPC .................................. A61B 5/07; A61B 5/073
See application file for complete search history.

(56) References Cited

U.S. PATENT DOCUMENTS 3,345,989 A    10/1967    Reynolds
3,409,721 A    11/1968    Applezweig
(Continued)

FOREIGN PATENT DOCUMENTS

CN    1588649    3/2005
CN    2748032    12/2005
(Continued)

OTHER PUBLICATIONS

AADE, "AADE 37th Annual Meeting San Antonio Aug. 4-7, 2010" American Association of Diabetes Educators Aug. 2010; http://www.diabeteseducator.org/annualmeeting/2010/index.html; 2 pp.
(Continued)

*Primary Examiner* — Christian Jang
(74) *Attorney, Agent, or Firm* — K&L Gates LLP

(57) ABSTRACT

Methods, devices and systems for acquiring information useful to support a patient in implementing and adhering to a medically prescribed therapy plan are provided. The therapy may incorporate biofeedback methods and/or personalized therapy aspects. A method includes steps of receiving, by a receiving device, biometric information associated with an ingestible event marker; analyzing, by a
(Continued)

computing device having a microprocessor configured to perform a biometric information analysis, the biometric information; and determining a therapeutic recommendation at least partly on the basis of the analysis and/or integrating biofeedback techniques into patient therapy or activity. A system includes a biometric information module to receive biometric information associated with an ingestible event marker; an analysis module to analyze the biometric information; and a determination module to optionally determine and communicate a therapeutic recommendation at least partly on the basis of the analysis.

23 Claims, 44 Drawing Sheets

(51) Int. Cl.
    *G06F 19/00*         (2011.01)
    *H04B 13/00*         (2006.01)
    *A61B 5/021*         (2006.01)
    *A61B 5/024*         (2006.01)
    *A61B 5/11*          (2006.01)
(52) U.S. Cl.
    CPC ......... *G06F 19/322* (2013.01); *H04B 13/005* (2013.01); *A61B 5/021* (2013.01); *A61B 5/024* (2013.01); *A61B 5/1112* (2013.01); *A61B 5/486* (2013.01); *G06F 19/3456* (2013.01); *G06F 19/3481* (2013.01)

(56) References Cited

U.S. PATENT DOCUMENTS

| | | |
|---|---|---|
| 3,419,736 A | 12/1968 | Walsh |
| 3,589,943 A | 6/1971 | Grubb et al. |
| 3,607,788 A | 9/1971 | Adolph |
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,727,616 A | 4/1973 | Lenzkes |
| 3,799,802 A | 3/1974 | Schneble, Jr. et al. |
| 3,825,016 A | 7/1974 | Lale et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,105,023 A | 8/1978 | Merchese et al. |
| 4,106,348 A | 8/1978 | Auphan |
| 4,129,125 A | 12/1978 | Lester |
| 4,133,730 A | 1/1979 | DuBois et al. |
| 4,141,349 A | 2/1979 | Ory et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,281,664 A | 8/1981 | Duggan |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,526,474 A | 7/1985 | Simon |
| 4,547,391 A | 10/1985 | Jenkins |
| 4,559,950 A | 12/1985 | Vaughan |
| 4,564,363 A | 1/1986 | Bagnall et al. |
| 4,578,061 A | 3/1986 | Lemelson |
| 4,618,533 A | 10/1986 | Steuck |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,809,705 A | 3/1989 | Ascher |
| 4,835,373 A | 5/1989 | Adams et al. |
| 4,844,076 A | 7/1989 | Lesho |
| 4,871,974 A | 10/1989 | Davis et al. |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,997 A | 3/1991 | Eckenhoff et al. |
| 5,016,634 A | 5/1991 | Vock et al. |
| 5,079,006 A | 1/1992 | Urguhart |
| 5,167,626 A | 12/1992 | Casper |
| 5,176,626 A | 1/1993 | Soehendra |
| 5,179,578 A | 1/1993 | Ishizu |
| 5,245,332 A | 9/1993 | Katzenstein et al. |
| 5,261,402 A | 11/1993 | DiSabito |
| 5,263,481 A | 11/1993 | Axelgaard et al. |
| 5,276,710 A | 1/1994 | Iwasaki |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,411,535 A | 5/1995 | Fujii et al. |
| 5,412,372 A | 5/1995 | Parkhurst et al. |
| 5,428,961 A | 7/1995 | Sakakibara |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,468,222 A | 11/1995 | Altchuler |
| 5,485,841 A | 1/1996 | Watkin et al. |
| 5,511,548 A | 4/1996 | Riazzi et al. |
| 5,551,953 A | 9/1996 | Lattin et al. |
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,634,466 A | 6/1997 | Gruner |
| 5,634,468 A | 6/1997 | Platt |
| 5,638,406 A | 6/1997 | Sogabe |
| 5,645,063 A | 7/1997 | Straka et al. |
| 5,705,189 A | 1/1998 | Lehmann et al. |
| 5,720,771 A | 2/1998 | Snell |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,836,474 A | 11/1998 | Wessberg |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,917,346 A | 6/1999 | Gord |
| 5,921,925 A | 7/1999 | Cartmell et al. |
| 5,925,030 A | 7/1999 | Gross et al. |
| 5,925,066 A | 7/1999 | Kroll et al. |

(56) References Cited

U.S. PATENT DOCUMENTS

| | | |
|---|---|---|
| 5,957,854 A | 9/1999 | Besson et al. |
| 5,963,132 A | 10/1999 | Yoakum et al. |
| 5,965,629 A | 10/1999 | Jung et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,099,482 A | 8/2000 | Brune et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |
| 6,206,702 B1 | 3/2001 | Hayden et al. |
| 6,217,744 B1 | 3/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,411,567 B1 | 6/2002 | Niemiec et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,525,996 B1 | 2/2003 | Miyazawa |
| 6,526,315 B1 | 2/2003 | Inagawa |
| 6,531,026 B1 | 3/2003 | Takeichi et al. |
| 6,540,699 B1 | 4/2003 | Smith |
| 6,544,174 B2 | 4/2003 | West |
| 6,564,079 B1 | 5/2003 | Cory |
| 6,572,636 B1 | 6/2003 | Hagen et al. |
| 6,574,425 B1 | 6/2003 | Weiss et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,638,231 B2 | 10/2003 | Govari et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,679,830 B2 | 1/2004 | Kolarovic et al. |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,771,174 B2 | 8/2004 | Broas |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,939,292 B2 | 9/2005 | Mizuno |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,062,308 B1 * | 6/2006 | Jackson ............ 600/361 |
| 7,076,437 B1 | 7/2006 | Levy |
| 7,081,693 B2 | 7/2006 | Hamel et al. |
| 7,118,531 B2 | 10/2006 | Krill |
| 7,125,382 B2 | 10/2006 | Zhou et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |

(56) References Cited

U.S. PATENT DOCUMENTS

| | | |
|---|---|---|
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,295,877 B2 | 11/2007 | Govari |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,732 B1 | 2/2008 | Wiss |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,366,675 B1 | 4/2008 | Walker et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,419,468 B2 | 9/2008 | Shimizu et al. |
| 7,424,268 B2 | 9/2008 | Diener |
| 7,424,319 B2 | 9/2008 | Muehlsteff |
| 7,427,266 B2 | 9/2008 | Ayer et al. |
| 7,433,731 B2 | 10/2008 | Matsumura et al. |
| 7,471,665 B2 | 12/2008 | Perlman |
| 7,485,095 B2 | 2/2009 | Shusterman |
| 7,499,674 B2 | 3/2009 | Salokannel |
| 7,502,643 B2 | 3/2009 | Farringdon et al. |
| 7,505,795 B1 | 3/2009 | Lim et al. |
| 7,508,248 B2 | 3/2009 | Yoshida |
| 7,510,121 B2 | 3/2009 | Koenck |
| 7,512,448 B2 | 3/2009 | Malick |
| 7,512,860 B2 | 3/2009 | Miyazaki et al. |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,558,965 B2 | 7/2009 | Wheeler et al. |
| 7,575,005 B2 | 8/2009 | Mumford |
| 7,616,111 B2 | 11/2009 | Covannon |
| 7,616,710 B2 | 11/2009 | Kim et al. |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,689,437 B1 | 3/2010 | Teller et al. |
| 7,689,833 B2 | 3/2010 | Lange |
| 7,697,994 B2 | 4/2010 | VanDanacker et al. |
| 7,712,288 B2 | 5/2010 | Ramasubramanian et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,747,454 B2 | 6/2010 | Bartfeld et al. |
| 7,756,587 B2 | 7/2010 | Penner et al. |
| 7,764,996 B2 | 7/2010 | Zhang et al. |
| 7,779,614 B1 | 8/2010 | McGonagle et al. |
| 7,796,043 B2 | 9/2010 | Euliano et al. |
| 7,797,033 B2 | 9/2010 | D'Andrea et al. |
| 7,806,852 B1 | 10/2010 | Jursen |
| 7,809,399 B2 | 10/2010 | Lu |
| 7,844,341 B2 | 11/2010 | Von Arx et al. |
| 7,857,766 B2 | 12/2010 | Lasater et al. |
| 7,860,731 B2 | 12/2010 | Jackson et al. |
| 7,899,526 B2 | 3/2011 | Benditt et al. |
| 7,904,133 B2 | 3/2011 | Gehman et al. |
| D639,437 S | 6/2011 | Bishay et al. |
| 8,025,149 B2 | 9/2011 | Sterry et al. |
| 8,036,731 B2 | 10/2011 | Kimchy et al. |
| 8,036,748 B2 | 10/2011 | Zdeblick et al. |
| 8,060,249 B2 | 11/2011 | Bear et al. |
| 8,073,707 B2 | 12/2011 | Teller et al. |
| 8,083,128 B2 | 12/2011 | Dembo et al. |
| 8,123,576 B2 | 2/2012 | Kim |
| 8,135,596 B2 | 3/2012 | Jung et al. |
| 8,180,425 B2 | 5/2012 | Selvitelli et al. |
| 8,185,191 B1 | 5/2012 | Shapiro et al. |
| 8,185,646 B2 | 5/2012 | Headley |
| 8,200,320 B2 | 6/2012 | Kovacs |
| 8,209,018 B2 | 6/2012 | Osorio et al. |
| 8,214,007 B2 | 7/2012 | Baker et al. |
| 8,224,667 B1 | 7/2012 | Miller et al. |
| 8,238,998 B2 | 8/2012 | Park |
| 8,249,686 B2 | 8/2012 | Libbus et al. |
| 8,254,853 B2 | 8/2012 | Rofougaran |
| 8,258,962 B2 | 9/2012 | Robertson et al. |
| 8,262,394 B2 | 9/2012 | Walker et al. |
| 8,271,106 B2 | 9/2012 | Wehba et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,314,619 B2 | 11/2012 | Takiguchi |
| 8,315,687 B2 | 11/2012 | Cross et al. |
| 8,343,068 B2 | 1/2013 | Najafi et al. |
| 8,369,936 B2 | 2/2013 | Farringdon et al. |
| 8,386,009 B2 | 2/2013 | Lindberg et al. |
| 8,389,003 B2 | 3/2013 | Mintchev et al. |

(56) References Cited

U.S. PATENT DOCUMENTS

| | | | |
|---|---|---|---|
| 8,404,275 B2 | 3/2013 | Habboushe |
| 8,440,274 B2 | 5/2013 | Wang |
| 8,454,528 B2 | 6/2013 | Yuen et al. |
| 8,454,561 B2 | 6/2013 | Uber, III et al. |
| 8,514,086 B2 | 8/2013 | Harper et al. |
| 8,542,123 B2 | 9/2013 | Robertson |
| 8,564,432 B2 | 10/2013 | Covannon et al. |
| 8,564,627 B2 | 10/2013 | Suzuki et al. |
| 8,583,227 B2 | 11/2013 | Savage et al. |
| 8,597,186 B2 | 12/2013 | Hafezi et al. |
| 8,634,838 B2 | 1/2014 | Hellwig et al. |
| 8,660,645 B2 | 2/2014 | Stevenson et al. |
| 8,668,280 B2 | 3/2014 | Heller et al. |
| 8,718,193 B2 | 5/2014 | Arne et al. |
| 8,722,085 B2 | 5/2014 | McKinney et al. |
| 8,762,733 B2 | 6/2014 | Derchak et al. |
| 8,771,183 B2 | 7/2014 | Sloan |
| 8,810,260 B1 | 8/2014 | Zhou |
| 8,823,510 B2 | 9/2014 | Downey et al. |
| 8,836,513 B2 | 9/2014 | Hafezi et al. |
| 8,838,217 B2 | 9/2014 | Myr |
| 8,868,453 B2 | 10/2014 | Zdeblick |
| 8,908,943 B2 | 12/2014 | Berry et al. |
| 8,926,509 B2 | 1/2015 | Magar et al. |
| 8,932,221 B2 | 1/2015 | Colliou et al. |
| 8,945,005 B2 | 2/2015 | Hafezi et al. |
| 8,956,287 B2 | 2/2015 | Zdeblick et al. |
| 8,966,973 B1 | 3/2015 | Milone |
| 8,989,837 B2 | 3/2015 | Weinstein et al. |
| 9,031,658 B2 | 5/2015 | Chiao et al. |
| 9,047,746 B1 | 6/2015 | Euliano et al. |
| 9,060,708 B2 | 6/2015 | Robertson et al. |
| 9,083,589 B2 | 7/2015 | Arne et al. |
| 9,125,868 B2 | 9/2015 | McKinney et al. |
| 9,189,941 B2 | 11/2015 | Eschelman et al. |
| 9,226,663 B2 | 1/2016 | Fei |
| 9,226,679 B2 | 1/2016 | Balda |
| 9,235,683 B2 | 1/2016 | Robertson et al. |
| 9,258,035 B2 | 2/2016 | Robertson et al. |
| 9,270,025 B2 | 2/2016 | Robertson et al. |
| 9,277,864 B2 | 3/2016 | Yang et al. |
| 9,278,177 B2 | 3/2016 | Edwards et al. |
| 9,433,371 B2 | 9/2016 | Hafezi et al. |
| 9,439,582 B2 | 9/2016 | Berkman et al. |
| 9,439,599 B2 | 9/2016 | Thompson et al. |
| 9,517,012 B2 | 12/2016 | Lane et al. |
| 9,603,550 B2 | 3/2017 | Behzadi |
| 2001/0027331 A1 | 10/2001 | Thompson |
| 2001/0031071 A1 | 10/2001 | Nichols et al. |
| 2001/0039503 A1 | 11/2001 | Chan et al. |
| 2001/0044588 A1 | 11/2001 | Mault |
| 2001/0051766 A1 | 12/2001 | Gazdzinski |
| 2001/0056262 A1 | 12/2001 | Cabiri et al. |
| 2002/0002326 A1 | 1/2002 | Causey et al. |
| 2002/0019586 A1 | 2/2002 | Teller et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0067270 A1 | 6/2002 | Yarin et al. |
| 2002/0077620 A1 | 6/2002 | Sweeney et al. |
| 2002/0132226 A1 | 9/2002 | Nair |
| 2002/0138009 A1 | 9/2002 | Brockway et al. |
| 2002/0173696 A1* | 11/2002 | Kolarovic ............... A61G 11/00 600/22 |
| 2002/0184415 A1 | 12/2002 | Naghavi et al. |
| 2002/0192159 A1 | 12/2002 | Reitberg |
| 2002/0193669 A1 | 12/2002 | Glukhovsky |
| 2002/0193846 A1 | 12/2002 | Pool et al. |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0037063 A1 | 2/2003 | Schwartz |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0198619 A1 | 10/2003 | Dong et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0216793 A1 | 11/2003 | Karlsson et al. |
| 2003/0229382 A1 | 12/2003 | Sun et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115507 A1 | 6/2004 | Potter et al. |
| 2004/0115517 A1 | 6/2004 | Fukada et al. |
| 2004/0121015 A1 | 6/2004 | Chidlaw et al. |
| 2004/0122296 A1* | 6/2004 | Hatlestad ............ A61B 5/02055 600/300 |
| 2004/0122297 A1 | 6/2004 | Stahmann et al. |
| 2004/0138558 A1 | 7/2004 | Dunki-Jacobs et al. |
| 2004/0147326 A1 | 7/2004 | Stiles |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0181155 A1* | 9/2004 | Glukhovsky ......... A61B 1/00147 600/476 |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/1215084 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0021372 A1 | 1/2005 | Mikkelsen |
| 2005/0024198 A1 | 2/2005 | Ward |
| 2005/0027175 A1 | 2/2005 | Yang |

(56) References Cited

U.S. PATENT DOCUMENTS

| | | |
|---|---|---|
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1* | 6/2005 | Alt et al. ............ 600/508 |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154277 A1 | 7/2005 | Tang et al. |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267550 A1 | 12/2005 | Hess et al. |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285732 A1 | 12/2005 | Sengupta et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0089858 A1 | 4/2006 | Ling |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253004 A1 | 11/2006 | Frisch et al. |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0287693 A1 | 12/2006 | Kraft et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0072156 A1 | 3/2007 | Kaufman et al. |
| 2007/0073353 A1 | 3/2007 | Rooney et al. |
| 2007/0088194 A1 | 4/2007 | Tahar |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0244810 A1 | 10/2007 | Rudolph |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |

(56) References Cited

U.S. PATENT DOCUMENTS

| | | |
|---|---|---|
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0004503 A1 | 1/2008 | Nisani et al. |
| 2008/0014866 A1 | 1/2008 | Lipowshi |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1* | 3/2008 | Schaldach et al. ........... 600/509 |
| 2008/0077188 A1 | 3/2008 | Denker et al. |
| 2008/0077430 A1 | 3/2008 | Singer et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188763 A1 | 8/2008 | John et al. |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214903 A1 | 9/2008 | Orbach |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0303665 A1 | 12/2008 | Naik et al. |
| 2008/0306357 A1 | 12/2008 | Korman |
| 2008/0306359 A1 | 12/2008 | Zdeblick et al. |
| 2008/0306360 A1* | 12/2008 | Robertson et al. ........... 600/302 |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0006133 A1 | 1/2009 | Weinert |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076350 A1 | 3/2009 | Bly et al. |
| 2009/0076397 A1 | 3/2009 | Libbus et al. |
| 2009/0082645 A1* | 3/2009 | Hafezi .................. A61B 5/073 600/302 |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149708 A1 | 6/2009 | Hyde et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1* | 7/2009 | Riskey ................ A61B 5/0031 600/302 |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |

(56) References Cited

U.S. PATENT DOCUMENTS

| | | |
|---|---|---|
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0247836 A1 | 10/2009 | Cole et al. |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0287109 A1 | 11/2009 | Ferren et al. |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0015584 A1 | 1/2010 | Singer et al. |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0082367 A1 | 4/2010 | Hains et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0100237 A1 | 4/2010 | Ratnakar |
| 2010/0106001 A1 | 4/2010 | Say et al. |
| 2010/0118853 A1 | 5/2010 | Godfrey |
| 2010/0131434 A1 | 5/2010 | Magent et al. |
| 2010/0139672 A1 | 6/2010 | Kroll et al. |
| 2010/0160742 A1* | 6/2010 | Seidl et al. ............... 600/301 |
| 2010/0168659 A1 | 7/2010 | Say et al. |
| 2010/0179398 A1 | 7/2010 | Say et al. |
| 2010/0183199 A1 | 7/2010 | Smith et al. |
| 2010/0185055 A1 | 7/2010 | Robertson |
| 2010/0191073 A1 | 7/2010 | Tarassenko et al. |
| 2010/0203394 A1 | 8/2010 | Bae et al. |
| 2010/0210299 A1 | 8/2010 | Gorbachov |
| 2010/0217100 A1 | 8/2010 | LeBoeuf et al. |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |
| 2011/0004079 A1 | 1/2011 | Al Ali et al. |
| 2011/0009715 A1* | 1/2011 | O'Reilly et al. ............... 600/302 |
| 2011/0021983 A1 | 1/2011 | Jurson |
| 2011/0029622 A1 | 2/2011 | Walker et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0081860 A1 | 4/2011 | Brown et al. |
| 2011/0105864 A1 | 5/2011 | Robertson et al. |
| 2011/0112686 A1 | 5/2011 | Nolan et al. |
| 2011/0124983 A1 | 5/2011 | Kroll et al. |
| 2011/0144470 A1 | 6/2011 | Mazar et al. |
| 2011/0160549 A1 | 6/2011 | Saroka et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0270112 A1 | 11/2011 | Manera et al. |
| 2011/0270135 A1 | 11/2011 | Dooley et al. |
| 2011/0279963 A1 | 11/2011 | Kumar et al. |
| 2012/0029309 A1 | 2/2012 | Paquet et al. |
| 2012/0062371 A1 | 3/2012 | Radivojevic et al. |
| 2012/0071743 A1 | 3/2012 | Todorov et al. |
| 2012/0024889 A1 | 4/2012 | Robertson et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0116184 A1 | 5/2012 | Shieh |
| 2012/0179004 A1 | 7/2012 | Roesicke et al. |
| 2012/0197144 A1 | 8/2012 | Christ et al. |
| 2012/0214140 A1 | 8/2012 | Brynelson et al. |
| 2012/0265544 A1 | 10/2012 | Hwang et al. |
| 2012/0299723 A1 | 11/2012 | Hafezi et al. |

(56) References Cited

U.S. PATENT DOCUMENTS

| | | | |
|---|---|---|---|
| 2012/0310070 A1 | 12/2012 | Kumar et al. | |
| 2012/0316413 A1 | 12/2012 | Liu et al. | |
| 2013/0030259 A1 | 1/2013 | Thomsen et al. | |
| 2013/0057385 A1 | 3/2013 | Murakami et al. | |
| 2013/0060115 A1 | 3/2013 | Gehman et al. | |
| 2013/0171596 A1 | 7/2013 | French | |
| 2013/0196012 A1 | 8/2013 | Dill | |
| 2014/0039445 A1 | 2/2014 | Austin et al. | |
| 2014/0280125 A1 | 9/2014 | Bhardwaj et al. | |
| 2014/0308930 A1 | 10/2014 | Tran | |
| 2014/0315170 A1 | 10/2014 | Ionescu et al. | |
| 2014/0349256 A1 | 11/2014 | Connor | |
| 2014/0374276 A1 | 12/2014 | Guthrie et al. | |
| 2015/0051465 A1 | 2/2015 | Robertson et al. | |
| 2015/0080677 A1 | 3/2015 | Thompson et al. | |
| 2015/0080678 A1 | 3/2015 | Frank et al. | |
| 2015/0080679 A1 | 3/2015 | Frank et al. | |
| 2015/0080680 A1 | 3/2015 | Zdeblick et al. | |
| 2015/0080681 A1 | 3/2015 | Hafezi et al. | |
| 2015/0127737 A1 | 5/2015 | Thompson et al. | |
| 2015/0127738 A1 | 5/2015 | Thompson et al. | |
| 2015/0149375 A1 | 5/2015 | Thompson et al. | |
| 2015/0165313 A1 | 6/2015 | Thompson et al. | |
| 2015/0171924 A1 | 6/2015 | Zdeblick | |
| 2015/0182463 A1 | 7/2015 | Hafezi et al. | |
| 2015/0193593 A1 | 7/2015 | Zdeblick et al. | |
| 2015/0230728 A1 | 8/2015 | Hafezi et al. | |
| 2015/0365115 A1 | 12/2015 | Arne et al. | |
| 2016/0106339 A1 | 4/2016 | Behzadi et al. | |
| 2016/0155316 A1 | 6/2016 | Hafezi et al. | |
| 2017/0000180 A1 | 1/2017 | Arne et al. | |
| 2017/0215761 A1 | 8/2017 | Zdeblick | |

FOREIGN PATENT DOCUMENTS

| | | |
|---|---|---|
| CN | 1991868 | 7/2007 |
| CN | 101005470 | 7/2007 |
| CN | 201076456 | 6/2008 |
| CN | 101524267 | 9/2009 |
| DE | 10313005 | 10/2004 |
| EP | 0344939 | 12/1989 |
| EP | 0526166 | 2/1993 |
| EP | 1199670 | 4/2002 |
| EP | 1246356 | 10/2002 |
| EP | 1342447 | 9/2003 |
| EP | 1534054 | 5/2005 |
| EP | 1702553 | 9/2006 |
| EP | 1098591 | 1/2007 |
| EP | 2143369 | 1/2010 |
| GB | 775071 | 5/1957 |
| GB | 2432862 | 6/2007 |
| IL | 172917 | 6/2010 |
| JP | 61017949 | 1/1986 |
| JP | 61072712 | 4/1986 |
| JP | S63280393 | 11/1988 |
| JP | H01285247 | 11/1989 |
| JP | 05-228128 | 9/1993 |
| JP | H0646539 | 2/1994 |
| JP | H0884779 | 4/1996 |
| JP | 09-330159 | 12/1997 |
| JP | 10-14898 | 1/1998 |
| JP | H11195415 | 7/1999 |
| JP | 2000-506410 | 5/2000 |
| JP | 2001078974 | 3/2001 |
| JP | 2002-224053 | 8/2002 |
| JP | 2002263185 | 9/2002 |
| JP | 2002282218 | 10/2002 |
| JP | 2002282219 | 10/2002 |
| JP | 2002291684 | 10/2002 |
| JP | 2003210395 | 7/2003 |
| JP | 2003325440 | 11/2003 |
| JP | 2004-7187 | 1/2004 |
| JP | 2004507188 | 3/2004 |
| JP | 2004134384 | 4/2004 |
| JP | 2004-313242 | 11/2004 |
| JP | 2004318534 | 11/2004 |
| JP | 2004364016 | 12/2004 |
| JP | 2005-073886 | 3/2005 |
| JP | 2005-087552 | 4/2005 |
| JP | 2005-304880 | 4/2005 |
| JP | 2005124708 | 5/2005 |
| JP | 2005148021 | 6/2005 |
| JP | 2005152037 | 6/2005 |
| JP | 2005287691 | 10/2005 |
| JP | 2005-532841 | 11/2005 |
| JP | 2005-532849 | 11/2005 |
| JP | 2005343515 | 12/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2006346000 | 12/2006 |
| JP | 3876573 | 1/2007 |
| JP | 2007151809 | 6/2007 |
| JP | 2007159631 | 6/2007 |
| JP | 2007-313340 | 12/2007 |
| JP | 2007330677 | 12/2007 |
| JP | 2008011865 | 1/2008 |
| JP | 2008501415 | 1/2008 |
| JP | 2008191955 | 8/2008 |
| JP | 2008289724 | 12/2008 |
| JP | 2009034345 | 2/2009 |
| JP | 2009-061236 | 3/2009 |
| JP | 2009050541 | 3/2009 |
| JP | 2011519583 | 7/2011 |
| KR | 20020015907 | 3/2002 |
| KR | 20020061744 | 7/2002 |
| KR | 200609977523 | 7/2006 |
| KR | 927471 | 11/2009 |
| KR | 20110137001 | 12/2011 |
| KR | 10-2012-09995 | 9/2012 |
| TW | 200301864 | 7/2003 |
| TW | 553735 | 9/2003 |
| TW | 200724094 | 7/2007 |
| TW | 200812556 | 3/2008 |
| TW | 201120673 | 6/2011 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO9516393 | 6/1995 |
| WO | WO1997014112 | 4/1997 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000033246 | 6/2000 |
| WO | WO2001000085 | 1/2001 |
| WO | WO2001047466 | 7/2001 |
| WO | WO2001049364 | 7/2001 |
| WO | WO2001074011 | 10/2001 |
| WO | WO2001080731 | 11/2001 |
| WO | WO0235997 | 5/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |

(56) References Cited

FOREIGN PATENT DOCUMENTS

| | | |
|---|---|---|
| WO | WO2004110555 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005069887 | 8/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2006009404 | 1/2006 |
| WO | WO2006016370 | 2/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006059338 | 6/2006 |
| WO | WO2006075016 | 7/2006 |
| WO | WO2006100620 | 9/2006 |
| WO | WO 2006109072 | 10/2006 |
| WO | WO2006/123346 | 11/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007123923 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2008104843 | 1/2008 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008085131 | 7/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009005759 | 1/2009 |
| WO | WO2009006615 | 1/2009 |
| WO | WO2009022343 | 2/2009 |
| WO | WO2009029453 | 3/2009 |
| WO | WO2009032381 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010107980 | 9/2010 |
| WO | WO2010115194 | 10/2010 |
| WO | WO2010132331 | 11/2010 |
| WO | WO2010135516 | 11/2010 |
| WO | WO2011024560 | 3/2011 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |
| WO | WO2015112603 | 7/2015 |

OTHER PUBLICATIONS

Arshak et al., A Review and Adaptation of Methods of Object Tracking to Telemetry Capsules IC-Med; Jan. 2007 vol. 1, No. 1, Issue 1, 12pp.

"ASGE Technology Status Evaluation Report: wireless capsule endoscopy" American Soc. for Gastrointestinal Endoscopy; Apr. 2006 vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; Sep. 2003; Abstract Only.

Barrie, Heidelberg pH capsule gastric analysis. Texbook of Natural Medicine, (1992), Pizzorno, Murray & Barrie.

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastoenterology; Oct. 2008 vol. 22, Issue 5, 1pp. (Abstract Only).

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

(56) References Cited

OTHER PUBLICATIONS

Fawaz et al., "Enhanced Telemetry System using CP-QPSK Band-Pass Modulation Technique Suitable for Smart Pill Medical Application" IFIP IEEE Dubai Conference Apr. 2008; http://www.asic.fh-offenburg.de/downloads/ePille/IFIP_IEEE_Dubai_Conference.pdf.
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Gaglani S. "Put Your Phone, or Skin, on Vibrate" MedGadget; Mar. 2012 http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng; Dec. 2007 54(12) 1pp. (Abstract Only).
Greene, "Edible RFID microchip monitor can tell if you take your medicine" Bloomberg Businessweek; Mar. 2010 2 pp.; http://www.businessweek.com/idg/2010-03-31/edible-rfid-microchip-monitor-can-tell-if-you-take-your-medicine.html.
Halthion Medical Technologies "Providing Ambulatory Medical Devices Which Monitor, Measure and Record" webpage. Online website: http://www.halthion.com/; downloaded May 30, 2012.
Heydari et al., "Analysis of the PLL jitter due to power/ground and substrate noise"; IEEE Transactions on Circuits and Systems (2004) 51(12): 2404-16.
Hoeksma, J. "New 'smart pill' to track adherence" E-Health-Insider May 2010 http://www.e-health-insider.com/news/5910/new_'smart_pill'_monitors_medicines.
Hoover et al., "Rx for health: Engineers design pill that signals it has been swallowed" University of Florida News; Mar. 2010 2pp.; http://news.ufl.edu/2010/03/31/antenna-pill-2/.
ISFET—Ion Sensitive Field-Effect Transistor; Microsens S.A. pdf document. Office Action dated Jun. 13, 2011 for U.S. Appl. No. 12/238,345; 4pp.
Intromedic, MicroCam Innovative Capsule Endoscope Pamphlet. (2006) 8 pp (http://www.intromedic.com/en/product/productinfo.asp).
Juvenile Diabetes Research Foundation International (JDRF), "Artificial Pancreas Project" Jun. 2010; http://www.artificialpancreasproject.com/; 3 pp.
Kamada K., "Electrophoretic deposition assisted by soluble anode" Materials Letters 57 (2003) 2348-2351.
Li, P-Y, et al. "An electrochemical intraocular drug delivery device", Sensors and Actuators A 143; p. 41-48.; Jul. 2007.
Lifescan, "OneTouch UltraLink™" http://www.lifescan.com/products/meters/ultralink; Jul. 2010 2 pp.
MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
MacKay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
Medtronic, "CareLink Therapy Management Software for Diabetes" Jul. 2010; https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® Real-Time Revel™ System" Aug. 2010 http://www.medtronicdiabetes.com/products/index.html; 2 pp.
Medtronic, "Mini Med Paradigm® Revel™ Insulin Pump" Jul. 2010 http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget; Jul. 2008; http://www.engadget.com/2008/07/29/walkers-swallow-rfid-pills-for-science/.
Minimitter Co. Inc. "Actiheart" Traditional 510(k) Summary. Sep. 27, 2005.
Minimitter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. 9-21 (1999).
Mini Mitter Co, Inc. 510(k) Premarket Notification for VitalSense. Apr. 22, 2004.
Minimitter Co. Inc. VitalSense Integrated Physiological Monitoring System. Product Description. Jul. 2005.
Minimitter Co. Inc. VitalSense Wireless Vital Signs Monitoring. Temperatures.com Mar. 31, 2009.
Mojaverian et al., "Estimation of gastric residence time of the Heidelberg capsule in humans: effect of varying food composition" Gastroenterology (1985) 89:(2): 392-7.
NPL_AntennaBasics.pdf, Radio Antennae, http://www.erikdeman.de/html/sail018h.htm; (2008) 3pp.
O'Brien et al., "The Production and Characterization of Chemically Reactive Porous Coatings of Zirconium Via Unbalanced Magnetron Sputtering" Surface and Coatings Technology (1996) 86-87; 200-206.
Park, "Medtronic to Buy MiniMed for $3.7 Billion" (2001) HomeCare; http://homecaremag.com/mag/medical_medtronic_buy_minimed/; 2 pp.
"RFID "pill" monitors marchers" RFID News; Jul. 2008 http://www.rfidnews.org/2008/07/23/rfid-pill-monitors-marchers/.
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6; May 2002, p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics—Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).
"Smartlife awarded patent for knitted transducer" Innovation in Textiles News: http://www.innovationintextiles.com/articles/208.php; 2pp. Aug. 2009.
"The SmartPill Wireless Motility Capsule" Smartpill, The Measure of GI Health; May 2010 http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1 3pp.

(56) References Cited

OTHER PUBLICATIONS

Tajalli et al., "Improving the power-delay performance in subthreshold source-coupled logic circuits" Integrated Circuit and System Design. Power and Timing Modeling, Optimization and Stimulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
U.S. Appl. No. 12/238,345, filed Sep. 25, 2008, Hooman et al., Non-Final Office Action dated Jun. 13, 2011 22pp.
Walkey, "MOSFET Structure and Processing"; 97.398* Physical Electronics Lecture 20; Office Action dated Jun. 13, 2011 for U.S. Appl. No. 12/238,345; 24 pp.
Watson, et al., "Determination of the relationship between the pH and conductivity of gastric juice" Physiol Meas. 17 (1996) pp. 21-27.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Zworkin, "A Radio Pill" Nature, (1957) 898, 179 Nature Publishing Group.
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Owano, N., "Study proposes smart sutures with sensors for wounds" phys.org. Aug. 2012. http://phys.org/news/2012-08-smart-sutures-sensors-wounds.html.
Platt, D., "Modulation and Deviation" AE6EO, Foothills Amateur Radio Society; Oct. 26, 2007; 61 pp.
"PALO Bluetooth Baseband" PALO Bluetooth Resource Center (2002) Retrieved from internet Dec. 12, 2012 at URL: http://palowireless.com/bluearticles/baseband.asp; first cited in Office Action dated Jan. 17, 2013 for EP08853901.0.
Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.
Hotz "The Really Smart Phone" The Wall Street Journal, What They Know (2011); 6 pp.; http://online.wsj.com/article/SB10001424052748704547604576263261679848814.html?mod=djemTECH_t.
Winter, J. et al. "The material properties of gelatin gels"; USA Ballistic Research Laboratories, Mar. 1975, p. 1-157.
Lin et al., "Do Physiological Data Relate to Traditional Usability Indexes?" Proceedings of OZCHI 2005, Canberra, Australia(2005) 10 pp.
Mandryk et al., "A physiological approach for continuously modeling user emotion in interactive play environments" Proceedings of Measuring Behavior (2008) (Maastrichtm The Netherlandsm Aug. 26-29) 2 pp.
Mandryk et al., "Objectively Evaluating Entertainment Technology" Simon Fraser University; CHI (2004) ACM 1-58113-703-6/04/0004; 2 pp.
Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Evanczuk, S., "PIC MCU software library uses human body for secure communications link" EDN Network; edn.com; Feb. 26, 2013 Retrieved from internet Jun. 19, 2013 at http://www.edn.com/electronics-products/other/4407842/PIC-MCU-software-library-uses-human-body-for-secure-communications-link; 5 pp.
Kim et al., "A Semi-Interpenetrating Network System for a Polymer Membrane"; Eur. Polym. J. vol. 33 No. 7; pp. 1009-1014 (1997).
Au-Yeung, K., et al., "A Networked System for Self-Management of Drug Therapy and Wellness", Wireless Health '10, Oct. 5-7, 2010, San Diego, 9 pages.
Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.
Ferguson et al., "Wireless communication with implanted medical devices using the conductive properties of the body," Expert Rev Med Devices, Jul. 2011, 8(4): 427-433.
Greene, "Medicaid Efforts to Incentivize Healthy Behaviours", Center for Health Care Strategies, Inc., Resource Paper, Jul. 2007.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
McDermott-Wells, P., "What is Bluetooth?", IEEE Potentials, IEEE, New York, NY, vol. 23, No. 5, Dec. 1, 2004, pp. 33-35.
Sharma, et al., "The Future is Wireless: Advances in Wireless Diagnostic and Therapeutic Technologies in Gastoenterology," Gastroenterology, Elsevier, Philadelphia, PA, vol. 137, No. 2, Aug. 1, 2009, pp. 434-439.
Aronson, J., "Meyer's Side Effects of Cardiovascular Drugs," Elsevier, Mar. 2, 2009, Medical , 840 pages. (Not Attached).
Herbig, S.M., "Asymmetric-membrane tablet coatings for osmotic drug delivery", Journal of Controlled Release 35 (1995) 127-136.
Lee, K. B.; "Two-step activation of paper batteries for high power generation: design and fabrication of biofluid- and wateractivated paper batteries"; J. Micromech. Microeng. 16 (2006) 2312-2317.
Lee, K. B.; "Urine-activated paper batteries for Biosystems"; J. Micromech. Microeng. 15 (2005) S21 O-S214.
Sammoura, F. et al., "Water-activated disposable and long shelf life microbatteries", Sensors and Actuators A 111 (2004) 79-86.
vonStetten, F. et al., "Biofuel cells as power generation for implantable devices", Pore. Eurosensors XX, (2006), pp. 22-225.
Chan, Adrian D.C., et al.,; "Wavelet Distance Measure for Person Identification Using Electrocardiograms," IEEE Transactions on Instrumentation and Measurement, IEEE Service Center, Piscataway, NJ, US, vol. 57, No. 2, Feb. 1, 2008, pp. 248-253.
Zhang, Y-T. et al., "Wireless Biomedical Sensing," Wiley Encyclopedia of Biomedical Engineering, 2006, pp. 1-9.

* cited by examiner

FIRST CALL RECORD 226.A

| PHONE ID 226.A.1 | 2ND PARTY ID 226.A.2 | ORIGIN 226.A.3 |
|---|---|---|
| START 226.A.4 | DURATION 226.A.5 | GPS 226.A.6 |

FIRST GPS RECORD 228.A

| PHONE ID 228.A. | GPS S DATA 228.A.2 | GPS TIME 228.A.3 |

FIRST TEXT RECORD 230.A

| PHONE ID 230.A.1 | 2ND PARTY ID 230.A.2 | TEXT TIME 230.A.3 | TEXT ORIGIN 230.A.4 |

FIRST PATIENT RECORD 232.A

| PATIENT ID 232.A.1 | PHONE ID 232.A.2 | BIOMETRIC DATA 232.A.3 | INGESTION RECORDS 232.A.4 | REMINDER MESSAGE INSTRUCTIONS 232.A.5 | BEHAVIOR DATA 232.A.6 |
|---|---|---|---|---|---|

| PATIENT ID 232.A.1 | PHONE ID 232.A.2 | FIRST ACTIVITY NOTE 234.A.1 | 2ND ACTIVITY NOTE 234.A.2 | FI2RD ACTIVITY NOTE 234.A.2 | NTH ACTIVITY NOTE 234.A.N |
|---|---|---|---|---|---|

FIRST PATIENT ACTIVITY LOG 234.A

FIGURE 32

| PATIENT ID 232.A.1 | PHONE ID 232.A.2 | FIRST GENETIC TEST NOTE 238.A.1 | SECOND GENETIC TEST NOTE 238.A.2 | THIRD GENETIC TEST NOTE 238.A.3 | FIRST GENETIC TEST NOTE 238.A.N |
|---|---|---|---|---|---|

FIRST PATIENT GENETIC RECORD 238.A

INGESTION-RELATED BIOFEEDBACK AND PERSONALIZED MEDICAL THERAPY METHOD AND SYSTEM

CROSS-REFERENCE TO RELATED APPLICATIONS

The present application is a U.S. national phase application filed under 35 U.S.C. § 371 of International Patent Application No. PCT/US2010/020269, entitled "INGESTION-RELATED BIOFEEDBACK AND PERSONALIZED MEDICAL THERAPY METHOD AND SYSTEM," filed Jan. 6, 2010, which application claims the benefit of both U.S. Provisional Patent Application No. 61/142,869, filed on Jan. 6, 2009, titled "INGESTION-RELATED BIOFEEDBACK METHOD AND SYSTEM"; and U.S. Provisional Patent Application No. 61/260,325, filed on Nov. 11, 2009, titled "METHOD AND SYSTEM FOR PERSONALIZED MEDICAL THERAPY", the entire disclosures of which are hereby incorporated by reference herein.

INTRODUCTION

The present invention relates generally to medical therapy systems, devices, and methods. More specifically, the invention relates to systems, devices, and methods for applying information related to an ingestion by a patient of a device, medication or substance.

Proper adjustment of medical treatment is an important factor in the success of medical therapies. Although some conclusions regarding the efficacy of treatment may be drawn from analysis of the patient's direct sensory symptoms during treatment and used as a modification indicator, many conditions exist where the patient has little direct sensory awareness. Hypertension is one such disease state. Patient adherence is another important factor in the success of medical therapies. Reliable adherence information may be used to inform efficacy and modification determinations. Lack of reliable adherence information, however, may be an issue. Adherence information may not be available. Further, adherence information may be faulty, inaccurate, or inadequate. Poorly informed medical treatment decisions, for example, those made in the absence of comprehensive, adherence information, may result in suboptimal therapy programs. Such programs may result in loss of quality of life, loss in health, and/or loss of life span.

Biofeedback is one technique that can be used to adjust medical treatment and to encourage patient adherence to medical therapy. Biofeedback may be defined as the technique of revealing certain selected internal physiologic indicators of physical health by presenting verbal, textual, visual and/or auditory signals to a monitored person in order to help the monitored person to manipulate these otherwise involuntary, unfelt and/or little felt vital processes (such as blood pressure, heart beat and respiration rate and intensity). Biofeedback techniques can enable a person to modify a monitored physiologic indicator to achieve, or more consistently maintain, a healthy condition. Achieving such health management goals typically requires voluntary cooperation on the part of the subject.

The management of certain chronic diseases or ongoing health conditions, hypertension for example, can be supported by monitoring and controlling one or more vital aspects of a patient. Examples of these disease control parameters include blood glucose of diabetes patients, respiratory flow of asthma sufferers, blood pressure of hypertensive patients, cholesterol of cardiovascular disease victims, body weight of eating disorder patients, T-cell or viral count of HIV bearers, and frequency or timing of undesirable episodes of depression of mental health patients. Because of the continuous nature of these diseases, clinicians can gain valuable information by monitoring one or more vital health processes on a regular basis outside of a clinical care facility.

A patient may monitor and control one or more vital health parameters in clinician assisted self-care or outpatient treatment programs. The term "health parameter" refers to any parameter associated with health, e.g., the health of a patient, athlete, or other living being. In these treatment programs, patients are responsible for performing self-care actions which impact the control parameter. Patients are also responsible for measuring the control parameter to determine the success of the self-care actions and the need for further adjustments. The successful implementation of such a treatment program requires a high degree of motivation, training, and understanding on the part of the patients to select and perform the appropriate self-care actions. When reliable, useful guidance is provided to the patient in a timely manner, the patient's confidence may increase in the health improvement program. With an increase in confidence, the patient may be more likely to adhere to the health improvement program. Adherence, in turn, increases the likelihood of success of the health improvement program.

Further, ingestible pharmaceutical agents, for example, prescription and non-prescription medicines and substances can be an important aspect of a therapeutic regime prescribed to a given patient. Reliable monitoring of adherence to scheduled dosages of pharmaceutical agents is desirable to optimize biofeedback effectiveness.

There is a long-felt need to provide behavioral guidance developed in view of various physiologic parameters and longitudinal monitoring of vital health aspects of the patient.

SUMMARY

The present disclosure seeks to address at least some of the previously discussed problems. The present disclosure includes methods and systems for acquiring information useful to support a patient in implementing and adhering to a medically prescribed therapy plan. The therapy may incorporate biofeedback methods and/or personalized therapy aspects.

A method includes steps of acquiring biometric information associated with an ingestible event marker; analyzing, by a computing device having a microprocessor configured to perform a biometric information analysis, the biometric information; and determining a therapeutic recommendation at least partly on the basis of the analysis. The method further optionally includes integrating biofeedback techniques into patient therapy and/or activity.

A system includes a biometric information module to acquire information associated with an ingestible event marker; an analysis module to analyze the information; and a determination module to optionally determine and communicate a therapeutic recommendation to a patient at least partly on the basis of the analysis of the information.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Such incorporations include United States Patent Application Publication No. 20080284599 published on Nov. 20, 2008 titled "Pharma-Informatics System"; United States Patent Application Publication No. 20090135886 titled "Transbody Communication Systems Employing Communication Channels", United States Patent Application No. 20090082645, published on Mar. 26, 2009 titled "In-Body Device With Virtual Dipole Signal Amplification"; U.S. patent application Ser. No. 12/546,017 filed Sep. 21, 2009 titled, "Communication System With Partial Power Source"; U.S. Provisional Patent Application No. 61/251,088 filed Oct. 13, 2009 titled "Receiver and Method"; and U.S. Provisional Patent Application No. 61/034,085, filed Mar. 5, 2008.

Such incorporations further include patent applications filed under the Patent Cooperation Treaty ("PCT"), to include PCT Patent Application Serial No. PCT/US2006/016370, filed Apr. 28, 2006; PCT Patent Application Serial No. PCT/US07/82563, filed Oct. 17, 2007; PCT Patent Application Serial No. PCT/US2008/52845 filed Feb. 1, 2008; PCT Patent Application Serial No. PCT/US2006/016370 published as WO/2006/116718; PCT Patent Application Serial No. PCT/US2007/082563 published as WO/2008/052136; PCT Patent Application Serial No. PCT/US2007/024225 published as WO/2008/063626; PCT Patent Application Serial No. PCT/US2007/022257 published as WO/2008/066617; PCT Patent Application Serial No. PCT/US2008/053999 published as WO/2008/101107; PCT Patent Application Serial No. PCT/US2008/056296 published as WO/2008/112577; PCT Patent Application Serial No. PCT/US2008/056299 published as WO/2008/112578; and PCT Patent Application Serial No. PCT/US2008/077753.

The publications discussed or mentioned herein are provided solely for their disclosure prior to the filing date of the present application. Nothing herein is to be construed as an admission that the present invention is not entitled to antedate such publication by virtue of prior invention. Furthermore, the dates of publication provided herein may differ from the actual publication dates which may need to be independently confirmed.

BRIEF DESCRIPTION OF THE FIGURES

These, and further features of various aspects of the present invention, may be better understood with reference to the accompanying specification, wherein:

FIG. 32 is a schematic of an exemplary patient activity log.

DETAILED DESCRIPTION

While the present invention has been described with reference to specific methods, devices and systems, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Methods recited herein may be carried out in any order of the recited events which is logically possible, as well as the recited order of events.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 1:
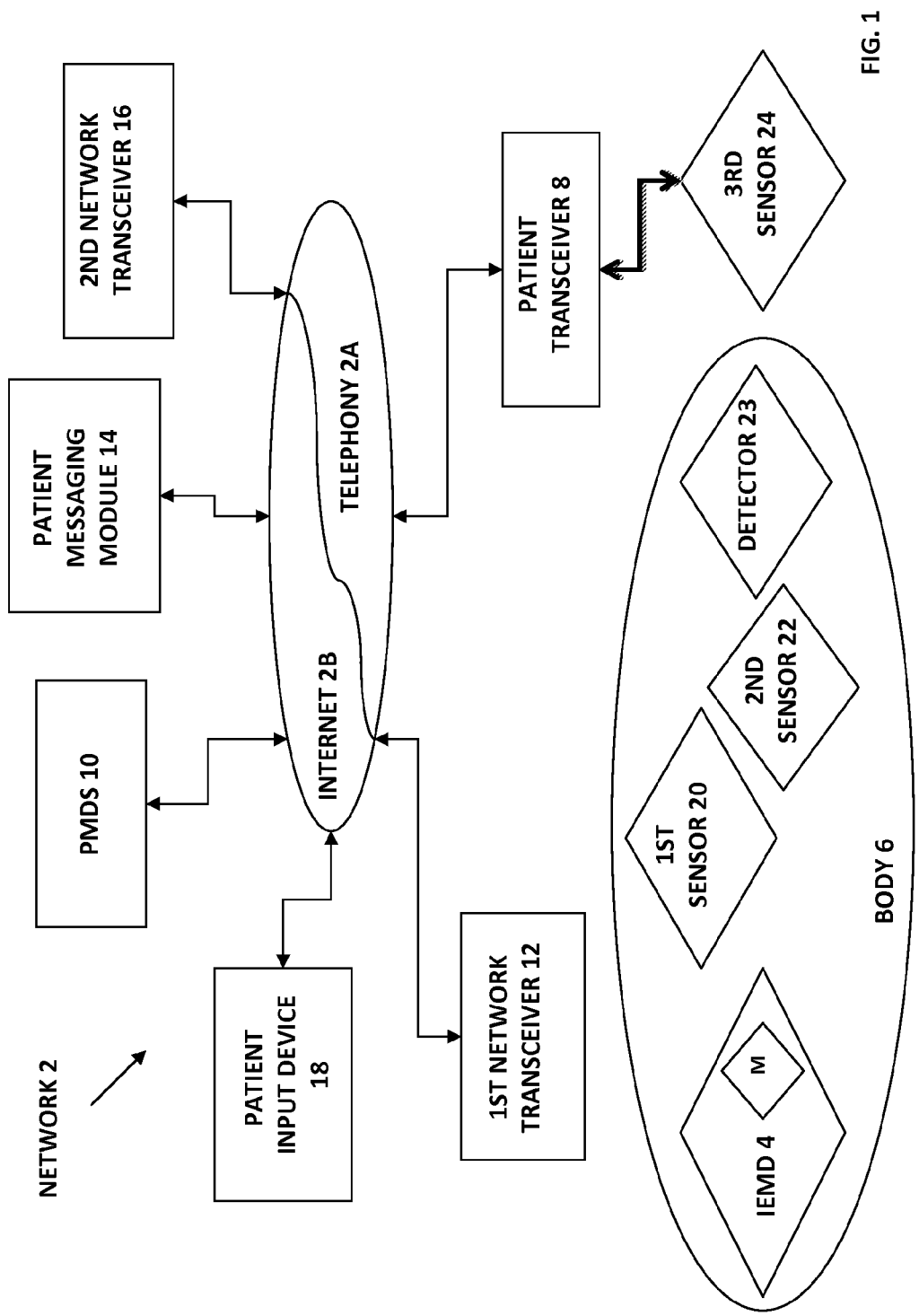
FIG. 1 is a schematic of an electronic communications network communicatively coupled with an IEMD, a patient management data system and one or more vital parameter sensors.

Referring now generally to the Figures and particularly to FIG. 1, FIG. 1 is a schematic of an electronic communications network 2 communicatively coupled with an ingestible device 4 (hereinafter "IEMD" 4) wherein the IEMD 4 has been ingested within a patient's body 6. A patient transceiver 8 is configured to receive a wireless transmission from the IEMD 4 that includes an ingestible event datum M, or "IEM M". Alternatively, the patient transceiver 8 may be configured to acquire communicated information comprising an IEM M, or a datum of an IEM M, via the electronic communications network 2 or an aspect device or source 6-24 communicatively coupled with or comprised within the electronic communications network 2.

The IEMD 4 gathers, collects, and/or generates ingestion data via various methods, e.g., ingestion timing, contact with alimentary system substances, sampling, etc. Further, various ingestible event marker data source devices IEMD 4 communicate the IEM M data via various methods, e.g., wireless methods, conductive methods via body tissue, etc. The following are examples of the ingestible devices 300*a*.

A pharma-informatics system described in PCT/US2006/016370, filed Apr. 28, 2006, includes compositions, systems and methods that allow for the detection of the actual physical delivery of a pharmaceutical agent to the body 6 are provided. Embodiments of the compositions include an identifier and an active agent.

A system described in PCT/US2008/52845, filed Feb. 1, 2008, includes an IEMD 4 referred to therein as an ingestible event marker IEM and patient transceiver 8 referred to therein as a personal signal receiver. Aspects of data transmitted from the IEMD 4 may include an identifier, which may or may not be present in a physiologically acceptable carrier. The identifier is characterized by being activated upon contact with a target internal physiological site of the body 6, such as digestive tract internal target site. The patient transceiver 8 may be configured to be associated with a physiological location, e.g., inside of or on the body 6, and to receive a signal from the IEMD 4. During use, the IEMD 4 broadcasts a signal which is received by the patient transceiver 8.

The ingestion data associated with the electronic communications network 2 (hereinafter "network" 2) include personal patient data, e.g., physiologic data generated by the IEMD 4. Examples are derived metrics, e.g., processed physical data to derive various metrics such as time of ingestion data; combined metrics, e.g., derived metrics combined with other derived metric data such as time of ingestion data combined with data identifying the ingested substance; and patient data, e.g., derived metrics and/or combined metrics aggregated with various physiologic data such as time of ingestion data combined with data identifying the ingested substance and physiologic data such as ECG data, temperature, etc.

Embodiments of activation component based on battery completion formats employ a battery that includes, when completed, a cathode, an anode, and an electrolyte, where the electrolyte is made up, at least in part, by fluid present at the target physiologic site (stomach fluid present in the stomach, where the stomach is the target physiological site). For example, when a stomach fluid activated IEM is ingested, it travels through the esophagus and proceeds to enter the stomach. The cathode and anode provided on the IEM do not constitute a full battery. However, when the cathode and anode are exposed to stomach fluid, the stomach fluid acts as the electrolyte component of the battery and completes the battery. Therefore, as the IEM contacts the target site, a power source is provided which activates the identifier. The data signal is then transmitted.

In certain embodiments, the IEMD is dimensioned to be orally ingestible, e.g., either by itself or upon combination with a physiologically acceptable carrier component of the composition so as to produce a composition that can be readily administered to a subject in need thereof. As such, in certain embodiments, the identifier element is dimensioned to have a width ranging from about 0.05 to about 2 or more mm, e.g., from about 0.05 mm to about 1 mm, such as from about 0.1 mm to about 0.2 mm; a length ranging from about 0.05 to about 2 or more mm, e.g., from about 0.05 mm to about 1 mm, such as from about 0.1 mm to about 0.2 mm and a height ranging from about 0.05 to about 2 or more mm, e.g., from about 0.1 mm to about 1 mm, such as from about 0.05 mm to about 0.3 mm, including from about 0.1 mm to about 0.2 mm. In certain embodiments the identifier is 1 mm3 or smaller, such as 0.1 mm3 or smaller, including 0.2 mm3 or smaller. The identifier element may take a variety of different configurations, such as but not limited to: a chip configuration, a cylinder configuration, a spherical configuration, a disc configuration, etc., where a particular configuration may be selected based on intended application, method of manufacture, etc.

A controlled activation ingestible identifier described in PCT Patent Application PCT/US07/82563, filed Oct. 17, 2007, includes ingestible compositions such as pharma-informatics enabled compositions. The controlled activation ingestible identifiers include a controlled activation element that provides for activation of the identifier in response to the presence of a predetermined stimulus at a target site of interest.

A life cycle pharma informatics system described in U.S. Patent Provisional Application Ser. No. 61/034,085, filed Mar. 5, 2008 includes RFID and conductive communications technology combined with medication and/or medication packaging such that the medication can be tracked for the duration of its existence. The system further allows in-body data transmissions while addressing the potential privacy and signal degradation concerns associated with RFID technology.

Additional examples of ingestible identifiers of interest include those described in Examples of different types of identifiers of interest include, but are not limited to, those identifiers described in PCT application serial no. PCT/US2006/016370 published as WO/2006/116718; PCT Patent Application Serial No. PCT/US2007/082563 published as WO/2008/052136; PCT Patent Application Serial No. PCT/US2007/024225 published as WO/2008/063626; PCT Patent Application Serial No. PCT/US2007/022257 published as WO/2008/066617; PCT Patent Application Serial No. PCT/US2008/052845 published as WO/2008/095183; PCT Patent Application Serial No. PCT/US2008/053999 published as WO/2008/101107; PCT Patent Application Serial No. PCT/US2008/056296 published as WO/2008/112577; PCT Patent Application Serial No. PCT/US2008/056299 published as WO/2008/112578; and PCT Patent Application Serial No. PCT/US2008/077753; the disclosures of which are herein incorporated by reference.

The patient transceiver 8 may be or comprise an electronic communications device configured for receipt of wireless transmissions from the IEMD 4 and optionally comprising, for example, (a.) an information appliance; (b.) a television set-top box; (c.) a VAIO FS8900™ notebook computer marketed by Sony Corporation of America, of New York City, N.Y., (d.) a SUN SPARCSERVER™ computer workstation marketed by Sun Microsystems of Santa Clara, Calif. and running a LINUX™ or a UNIX™ operating system; (e.) a wireless communications enabled personal computer configured for running WINDOWS XP™ or VISTA™ operating system marketed by Microsoft Corporation of Redmond, Wash.; (f.) a PowerBook G4™ personal computer as marketed by Apple Computer of Cupertino, Calif.; (g.) an iPhone™ cellular telephone as marketed by Apple Computer of Cupertino, Calif.; and/or (h.) a personal digital assistant enabled for wireless communications.

The electronic communications network 2 may be or comprise, for example, in whole or in part, a telephony network 2A, a wireless communications network, a computer network, and/or the Internet 2B.

The patient transceiver 8 is communicatively coupled with a patient management data system 10 (hereinafter, "PMDS" 10) via the electronics communications network 2. The patient transceiver 8 may be communicatively coupled with the electronics communications network 2 (hereinafter, "the network" 2) by a hard wire connection and/or a wireless communications mode with a first network transceiver 12, wherein the first network transceiver 12 is communicatively coupled with the network 2 by a hard wire connection.

A patient messaging module 14 is additionally coupled with the network 2, wherein the patient messaging module 14 enables a clinician or an automated information system (not shown) to transmit recommendations to the patient regarding medicinal ingestion, patient behavior and therapeutic activity. The patient messaging module 14 and/or the PDMS transceiver 8 may be communicatively coupled with the network 2 by means of a hard wire connection and/or a wireless communications mode with a second network transceiver 16, wherein the first network transceiver 12 is communicatively coupled with the network 2 by a hard wire connection.

It is understood that the patient messaging module 14 may be comprised within the PMDS 10, and that the patient messaging module 14 and/or the PMDS 10 may comprise or be comprised within a unified or distributed electronic information technology system configured for communication via the network 2 and optionally comprising, for example, (a.) an information appliance; (b.) a television set-top box; (c.) a VAIO FS8900™ notebook computer marketed by Sony Corporation of America, of New York City, N.Y., (d.) a SUN SPARCSERVER™ computer workstation marketed by Sun Microsystems of Santa Clara, Calif. and running a LINUX™ or a UNIX™ operating system; (e.) a wireless communications enabled personal computer configured for running WINDOWS XP™ or VISTA™ operating system marketed by Microsoft Corporation of Redmond, Wash.; (f.) a PowerBook G4™ personal computer as marketed by Apple Computer of Cupertino, Calif.; (g.) a mobile or cellular digital telephone; (h.) an iPhone™ cellular telephone as marketed by Apple Computer of Cupertino, Calif.; and/or (i.) a personal digital assistant enabled for wireless communications.

A patient input device 18 is additionally coupled with the network 2, wherein the patient input device 18 enables a patient or caregiver (not shown) to transmit reports and information regarding patient adherence or non-adherence to recommended therapy; patient behavior; patient physical, mental, or emotional condition; risk taking or risk seeking behavior by the patient; and therapeutic activity of the patient. The patient input device 18 may be included within the patient transceiver 8, and/or may comprise or be comprised within an electronic communications device, or a unified or distributed electronic information technology system configured for communication via the network 2 and optionally comprising, for example, (a.) an information appliance; (b.) a television set-top box; (c.) a VAIO FS8900™ notebook computer marketed by Sony Corporation of America, of New York City, N.Y., (d.) a SUN SPARCSERVER™ computer workstation marketed by Sun Microsystems of Santa Clara, Calif. and running a LINUX™ or a UNIX™ operating system; (e.) a wireless communications enabled personal computer configured for running WINDOWS XP™ or VISTA™ operating system marketed by Microsoft Corporation of Redmond, Wash.; (f.) a PowerBook G4™ personal computer as marketed by Apple Computer of Cupertino, Calif.; (g.) an iPhone™ cellular telephone as marketed by Apple Computer of Cupertino, Calif.; (h.) an iPhone™ cellular telephone as marketed by Apple Computer of Cupertino, Calif.; and/or (i.) a personal digital assistant enabled for wireless communications.

A first vital parameter monitor 20, or "first sensor" 20, is coupled with the patient's body 6 and may be or comprise, for example, a motion detector, a heart rate monitor, a blood pressure monitor, a respiration monitor, and/or a patient skin electrical current conductivity monitor. A second vital parameter monitor 22, or "second sensor" 22, is coupled with the patient's body 6 and may additionally be or comprise, for example, a motion detector 23, a heart rate monitor, a blood pressure monitor, a respiration monitor, and/or a patient skin electrical current conductivity monitor.

The motion detector 23 is communicatively coupled to the analysis module and the PMDS 10 whereby the PMDS 10 incorporates a patient motion datum generated by and communicated from the motion detector 23 in an analysis of at least one health parameter of a patient. The motion detector 23 may be, comprise, or comprised within, for example, a cellular telephone, an accelerometer and/or a global positioning signal device.

A third vital parameter monitor 24 is positioned remotely from the patient's body 6, and is configured to monitor a vital parameter of the patient's body 6 by remote sensing, for example, sound detection, air pressure variation, light energy reflection, and/or heat detection. The third sensor 24 may be or comprise a motion detector, for example, a heart rate monitor, a blood pressure monitor, a respiration monitor, and/or a patient skin electrical current conductivity monitor.

A system described in PCT/US2008/52845, filed Feb. 1, 2008, includes an IEMD 4 referred to therein as an ingestible event marker IEMD 4 and patient transceiver 8 referred to therein as a personal signal receiver. Aspects of IEM M data transmitted from the IEMD 4 and/or sensors 20, 22, 23 and 24 may include an identifier (sometimes, for example, referred to herein as an "ingestible event marker", an "ionic emission module", and/or an "IEM"), which may or may not be present in a physiologically acceptable carrier. The identifier is characterized by being activated upon contact with a target internal physiological site of a body, such as digestive tract internal target site. The patient transceiver 8 may be configured to be associated with a physiological location, e.g., inside of or on the body, and to receive a signal from the IEMD 4 and/or sensors 20, 22, 23 and 24. During use, the IEMD 4 and/or sensors 20, 22, 23 and 24 broadcasts signals that are received by the patient transceiver 8.

The ingestion data associated with the network 2 include personal data, e.g., physiologic data generated by the IEMD 4 and/or sensors 20, 22, 23 and 24. Examples are derived metrics, e.g., processed physical data to derive various metrics such as time of ingestion data; combined metrics, e.g., derived metrics combined with other derived metric data such as time of ingestion data combined with data identifying the ingested substance; and patient data, e.g., derived metrics and/or combined metrics aggregated with various physiologic data such as time of ingestion data combined with data identifying the ingested substance and physiologic data such as ECG data, temperature, etc.

A controlled activation ingestible identifier described in PCT/US07/82563, filed Oct. 17, 2007, includes ingestible compositions such as pharma-informatics enabled compositions. The controlled activation ingestible identifiers include a controlled activation element that provides for activation of the identifier in response to the presence of a predetermined stimulus at a target site of interest.

A life cycle pharma informatics system described in U.S. Patent Application Ser. No. 61/034,085, filed Mar. 5, 2008 includes RFID and conductive communications technology combined with medication and/or medication packaging such that the medication can be tracked for the duration of its existence. The system further allows in-body data transmissions while addressing the potential privacy and signal degradation concerns associated with RFID technology.

Figure 2:
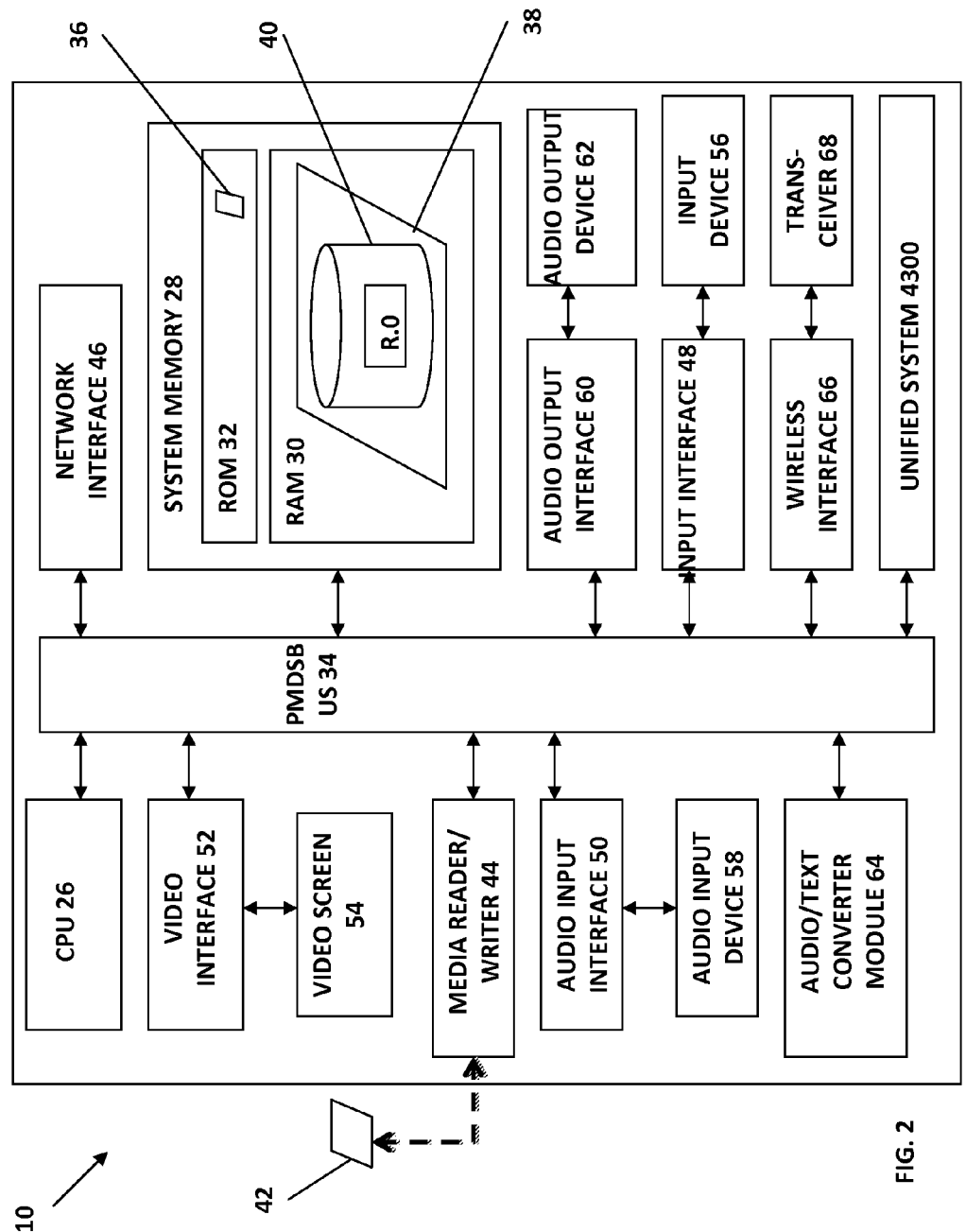
FIG. 2 is a schematic of the patient management data system of FIG. 1

The computer architecture shown in FIG. 2 illustrates the aspects of the PMDS 10, including a central processing unit 26 (hereinafter, "CPU"), a system memory 28, including a random access memory 30 (hereinafter, "RAM") and a read-only memory (hereinafter, "ROM") 32, and a power and communications system bus 34 that couples the system memory 28 to the CPU 26. A basic input/output system 36 containing the basic software-encoded instructions and routines that help to transfer information between elements within the PMDS 10, such as during startup, is stored in the ROM 20. The PMDS 10 further includes a system software 38 and a database management system 40 (hereinafter "DBMS" 40), which will be described in greater detail below, stored in the system memory 28 and/or a computer-readable medium 42.

A media writer/reader 44 is bi-directionally communicatively coupled to the CPU 26 through the power and communications system bus 34 (hereinafter "the bus" 34). The media writer/reader 44 and the associated computer-readable media 42 are selected and configure to provide non-volatile storage for the PMDS 10. Although the description of computer-readable media 42 contained herein refers to a mass storage device, such as a hard disk or CD-ROM drive, it should be appreciated by those skilled in the art that computer-readable media can be any available media that can be accessed by the PMDS 10.

By way of example, and not limitation, computer-readable media 42 may comprise computer storage media and communication media. Computer storage media includes volatile and non-volatile, removable and non-removable media implemented in any method or technology for storage of information such as computer-readable instructions, data structures, program modules or other data. Computer storage media includes, for example, but is not limited to, RAM, ROM, EPROM, EEPROM, flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the PMDS 10.

The computer-readable medium 42 may comprise machine-readable instructions which when executed by the PMDS 10 to cause the PMDS 10 to perform one or more steps as described in the Figures and enabled by the present disclosure. The bus 34 further bi-directionally communicatively couples a network interface 46, a user input interface 48, a user audio input interface 50, and a video screen interface 52 with the CPU 26 and the system memory 28. The video screen interface 52 directs visual presentations of data on a visual display screen 54 and bi-directionally communicatively couples the visual display screen 54 with the CPU 26 via the communications bus 34. The user input interface 48 couples a user input device 56, for example, an electronic keyboard, a computer mouse, a computer trackball, or a computer mouse pad, with the CPU 26 via the communications bus 34 and enables the clinician to input icon selections, commands and data to the PMDS 10. The icon selections may be chosen from images presented on the visual display screen 54.

The audio input interface 50 couples a user audio input device 58, for example an audio microphone, with the CPU 26 via the communications bus 34 and enables the clinician to input vocal input that communicates icon selections, commands and data to the PMDS 10, and/or digitized representations of verbal expressions. The digitized representations of verbal expressions may be transmitted via the network interface 46 to enable VoIP communications with the patient input device 18 and/or the patient transceiver 8.

An audio output interface 60 communicatively coupled with the communications bus 34 receives digitized verbal information, for example, VoIP messages, from the network 2 via the network interface 46 and drives the audio output device 62 to audibly output verbal message derived from the digitized verbal communications.

An audio/text converter module 64 (1.) converts digitized audio data into textual data for storage in a patient record R.0; and (b.) converts text data into audio data representative of vocalizations of the source text data. The converted text data may be received via the bus 34 and from the system memory 28 or the network 2, or generated by the CPU 26.

A wireless interface 66 enables bi-directional communication between the bus 34 and a wireless transceiver 68, whereby the PMDS 10 may communicate via the wireless and/or hard wired telephony network 2A with an element 8-16 to the network 2.

It is understood that the additional elements 8 and 12-16 of the network 2 may include one, several or all of the aspects 26-68 of the PMDS 10. It is further understood that the PMDS 10 may optionally, additionally or alternatively be configured to acquire a communicated information comprising an IEM M, or a datum of an IEM M, via the electronic communications network 2 or an aspect device or source 6-24 communicatively coupled with or comprised within the electronic communications network 2.

Figure 3:
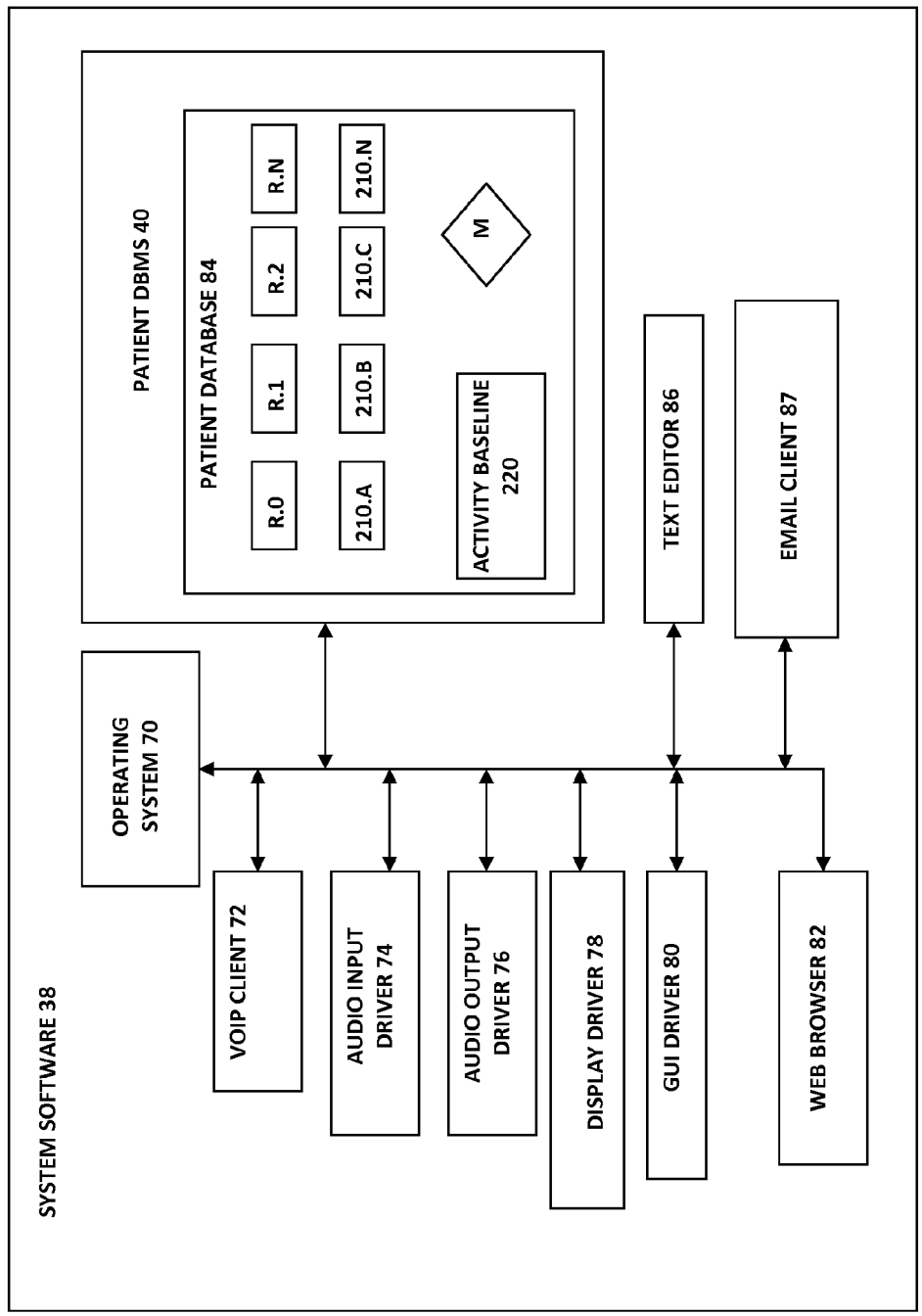
FIG. 3 is a schematic diagram of a system software of the patient management data system of FIGS. 1 and 2.

FIG. 3 is an illustration of the system software 38 of the PMDS 10 of FIGS. 1 and 2. An operating system 70 enables a VoIP client software module 72 to provide voice data to the network 2 by directing the audio input driver 74 to digitize acoustic signals detected by the audio input device 58 to form a digitized voice record and transmit the digitized voice record to the patient transceiver 8 and or the patient input device 18 via the network 2. It is understood that the first network transceiver 12 and/or the second network transceiver 16 may facilitate the transmission of voice communications between the PMDS 10 and the patient transceiver 8 and/or the patient input device 18. An audio output driver 76 processes digitized acoustic signals received from the network 2 and directs the audio output interface 60 and the audio output device 62 to derive and broadcast acoustic signals from the received digitized acoustic signals for hearing by the clinician.

A display driver 78 directs the video interface 52 and the video screen 54 to visually present information received from, or derived from inputs derived from the network 2, the patient transceiver 8, the patient input device 18, the first network transceiver 12, the second network transceiver 16, a graphical user interface driver 80 of the PMDS 10, the audio input device 58 and/or the input device 56. A web browser 82 may enable the PMDS 10 to visually display information received from the Internet 2B. The user record R.0 and a plurality of user records R.1-R.N are stored in a patient database 84 of the DBMS 40.

A text editor 86 and an email client 87 separately or in combination enable the clinician to, for example, prepare text messages, and/or to include reminder messages for medication ingestion, for transmission via the network 2 and to the patient transceiver 8 and or the patient input device 18. It is understood that the first network transceiver 12 and/or the second network transceiver 16 may facilitate the transmission of text messages between the PMDS 10 and the patient transceiver 8 and/or the patient input device 18.

It is understood that the additional elements 8 and 12-16 of the network 2 may include one, several or all of the software aspects 70-86 of the PMDS 10.

Figure 4A:
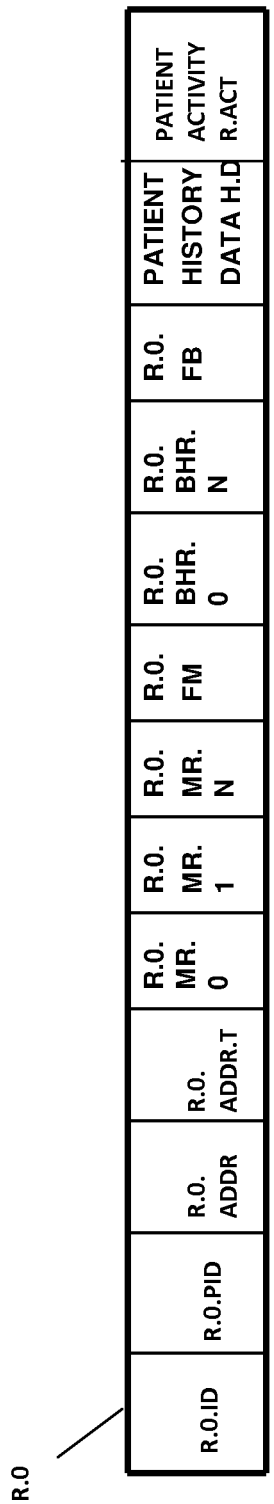
FIG. 4A is an illustration of a representative first patient record as stored in the patient management data system or elsewhere in the network of FIG. 1.

Referring now generally to the Figures and particularly to FIG. 4A, FIG. 4A is an illustration of the representative first patient record R.0 the format of which may be followed in whole or in part by one or more of the remaining patient records R.1-R.N. A first record identifier R.0.ID uniquely identifies the first record R.0 within the PMDS 10 and a patient identifier R.0.PID identifies the patient associated with the first record R.0. A network patient address R.0.ADDR identifies a network address of the patient transceiver 8 and/or the patient input device 18 to which electronic messages, for example, email messages, may be sent. A patient telephone number R.0.ADDR.T identifies a telephone number used to establish a telephonic communications session during which a text message or a voice communication maybe accomplished. One or more medication records R.0.MR.0-R.0.MR.N specify one or more medicines prescribed to the patient. A medication reminder flag R.0.FM indicates whether the patient is to be reminded by the PMDS 10 to ingest or otherwise apply a medication. One or more behavior records R.0.BHR.0-R.0.BHR.N specify one or more behaviors prescribed to the patient. A behavior remind flag R.0.FB indicates whether the patient is to be reminded by the PMDS 10 to engage in (or to avoid) a specified behavior. A patient history data retains information associated with the patient and may include records of receipt of attestations from the patient and receipt of ingestible event data IEM M. A patient activity data R.ACT retains information describing expected types of patient activities and expected times of the patients may be engaging in each expected activities.

Figure 4B:
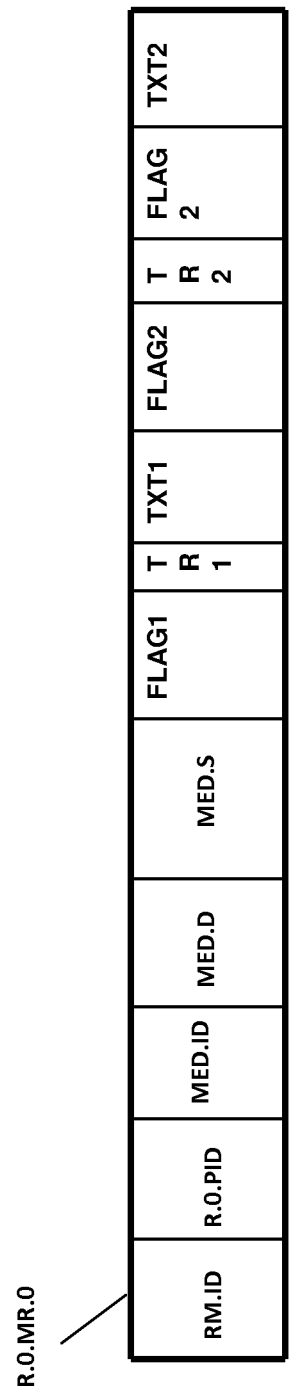
FIG. 4B is an illustration of a representative first medication record as stored in the patient management data system or elsewhere in the network of FIG. 1.

Referring now generally to the Figures and particularly to FIG. 4B, FIG. 4B is an illustration of the representative first medication record R.0.MR.0. A first medication record identifier RM.ID uniquely identifies the first medication record R.0.MR.0 within the PMDS 10, and the patient identifier R.0.PID identifies the patient associated with the first medication record R.0.MR.0. A medication identifier MED.ID identifies the medication and dosage thereof associated with the first medication record R.0.MR.0. A dosage data MED.D indicates what dosage of the identified medication is to be ingested or applied.

An application schedule MED.S indicates when the associated medication is prescribed to be ingested or otherwise applied. A first remind flag FLAG1 indicates if the patient shall be reminded to apply or ingest the associated medication before the next prescribed time, wherein the reminder may be sent at approximately a first remind time period TR1 before the next prescribed time. A first remind medication text TXT1 (hereinafter, "first remind text" TR1) is a prerecorded text message that may be sent prior to the scheduled time of ingestion or application as a reminder message to the patient to encourage ingesting or applying the associated medication.

A second remind flag FLAG2 indicates if the patient shall be reminded to ingest the medication associated with the first medication record R.0.MR.0 in the event that an ingestion event datum IEM M has not been received by the network 2 within a second remind TR2 time after a prescribed ingestion time has passed. A second remind text TXT2 is a prerecorded text message that may be sent after a scheduled time as a reminder message to the patient to encourage ingesting or applying the associated medication identified by the medication identifier MED.0.

Figure 4C:
FIG. 4C is an illustration of a representative first behavior recommendation record as stored in the patient management data system or elsewhere in the network of FIG. 1.

Referring now generally to the Figures and particularly to FIG. 4C, FIG. 4C is an illustration of the representative first behavior record R.0.BHR.0. A first behavior record identifier R.BHR.ID uniquely identifies the first behavior record R.0.BHR.0 within the PMDS 10, and the patient identifier R.0.PID identifies the patient associated with the first behavior record R.0.BHR.0. A behavior identifier BHR.ID identifies the behavior associated with the first behavior record R.0.BHR.0. A behavior description text BHR.D includes a textual description of a behavior recommended to be engaged in or avoided. A behavior application schedule BHR.S indicates when the associated behavior is prescribed to be ingested or otherwise applied. A first behavior remind flag BFLG1 indicates if the patient shall be reminded to perform or avoid the associated behavior before the next prescribed time, wherein the reminder may be sent at approximately a TRB1 time period before the next prescribed time. A first behavior text TXT1B is a prerecorded text message that may be sent prior to the scheduled time of ingestion or application as a reminder message to the patient to encourage performing, or alternatively avoided, the behavior identified by the behavior identifier BHR.ID.

A second behavior remind flag BFLG2 indicates if the patient shall be reminded to perform, or alternatively avoid, the behavior associated with the first behavior record R.0.BHR.0 if an attestation by the patient has not been received by the network 2 within a time after a prescribed time of performance has passed. A second behavior text TXT2B is a prerecorded text message that may be sent, for example, after a scheduled time of behavior performance, or alternatively, a behavior avoidance, as a reminder message to the patient to encourage performing, or alternatively avoid performing, the associated behavior identified by the behavior identifier BHR.ID.

Figure 4D:
FIG. 4D is an illustration of a representative patient history data of the first patient record of FIG. 4A.

Referring now generally to the Figures and particularly to FIG. 4D, FIG. 4D is an illustration of the representative patient history data H.D of the first record R.0. The patient history data H.D includes, for example, (a.) a plurality of marker record H.M0-H.MN of previously received ingestion markers IEM M, (b.) a plurality of attestation records H.PA0-H.PAN containing notations of attestations received from the patient, and (c.) a plurality of text message records H.T0-H.TN of previously transmitted text messages sent to the patient transceiver 8 and/or the patient input device 18. The received patient attestation records H.PA0-H.PAN may include, for example, notations of attestations of performed behaviors, attestations of applications or ingestions of medicines, and/or attestations of avoided behaviors.

Figure 5:
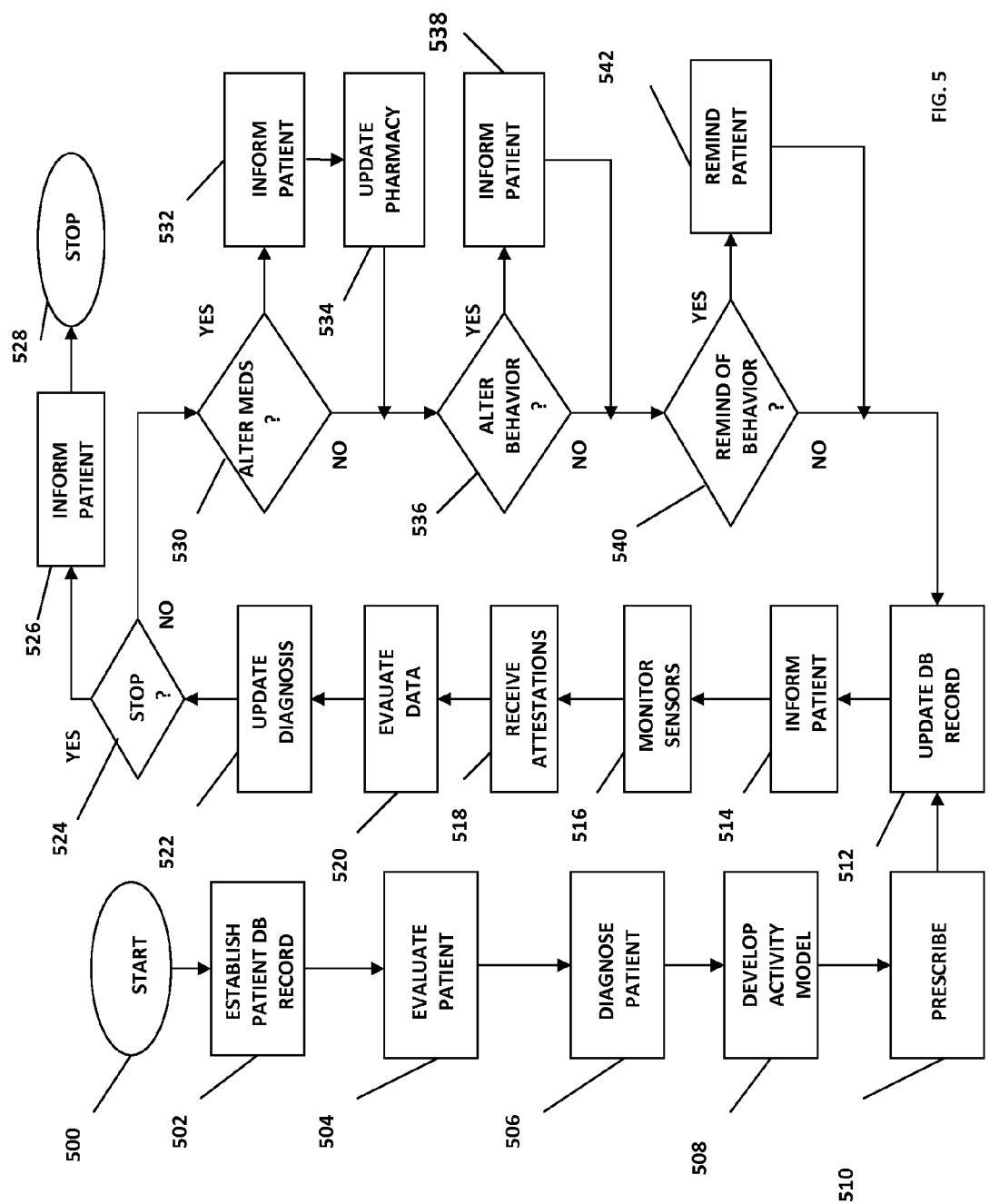
FIG. 5 is an illustration of additional aspects of the method of the present invention, wherein a patient is treated for a health condition by means of the electronic communications network, the IEMD, the patient management data system and one or more vital parameter sensors of FIGS. 1 and 2.

Referring now generally to the Figures and particularly to FIG. 5, FIG. 5 is an illustration of additional aspects of the method of the present invention, wherein a patient is treated for a health condition. In step 502 a database record R.0 is initiated in the PMDS 10 identifying the patient. The patient is evaluated in step 504 and diagnosed in step 506. A patient activity model is generated in step 508 wherein the daily activity of the patient is included in a software-encoded portion of the database record R.0. Medications and behaviors are prescribed in step 510 and the prescribed medications and behaviors are stored in the database record R.0.

The patient is counseled and advised of the prescribed medications and behaviors as stored in the database record R in step 514.

The receipt of ingestion markers IEM M transmitted from one or more IEMD's 4 and measurements and transmissions of the sensors 20, 22, 23 and 24 are received by the patient transceiver 8 and transmitted to the PMDS 10 via the network 2 and the patient record R.0 is updated with the received parametric data in step 516. Attestations by the patient, for example, of (a.) changes in patient activity varying from the activity model of step 508; (b.) adherence and non-adherence to prescribed medication ingestion schedule by the patient; and (c.) performance and non-performance of prescribed patient behaviors are received via the patient input device 18 and by the PMDS 10 via the network 2 in step 518.

The information received in steps 516 and 518 are evaluated by a clinician or an expert information technology system (not shown) in step 520 in view of other information included in the patient record R.0. The clinician or the expert information technology system may update the patient diagnosis in step 522, and may further determine in step 524 whether to cease treatment of the patient. When the clinician or expert system determines in step 824 that the current treatment cycle of the patient shall cease, the patient is informed of the cessation of treatment, and the database record R.0 is updated with a notice of treatment termination, in step 526. The treatment is ended in step 528.

When the clinician or expert system determines in step 524 that the current treatment cycle of the patient shall continue, the clinician or expert system determines by analysis of the patient record R.0, or one or more additional patient records R.0-R.N and optionally in consultation with the patient, determines in step 530 whether to increase or decrease medication dosage or frequency. When the clinician or expert system determines in step 530 to increase or decrease medication dosage or frequency, the patient is informed of the prescription change and the pharmacy is updated in step 534.

The clinician or expert system determines by analysis of the patient record R.0, and optionally in consultation with the patient determines in step 536 whether to alter prescribed or recommended behaviors. The patient is informed in step 538 of any alterations or additions of prescribed or recommended behaviors.

The PMDS 10 determines by analysis of the patient record R.0, in step 542 whether to remind the patient to, for example, ingest or apply a medication, or engage in a prescribed or recommended behavior, and the patient is reminded in step 542 to, for example, ingest or apply a medicine, or engage in a prescribed or recommended behavior.

Figure 6:
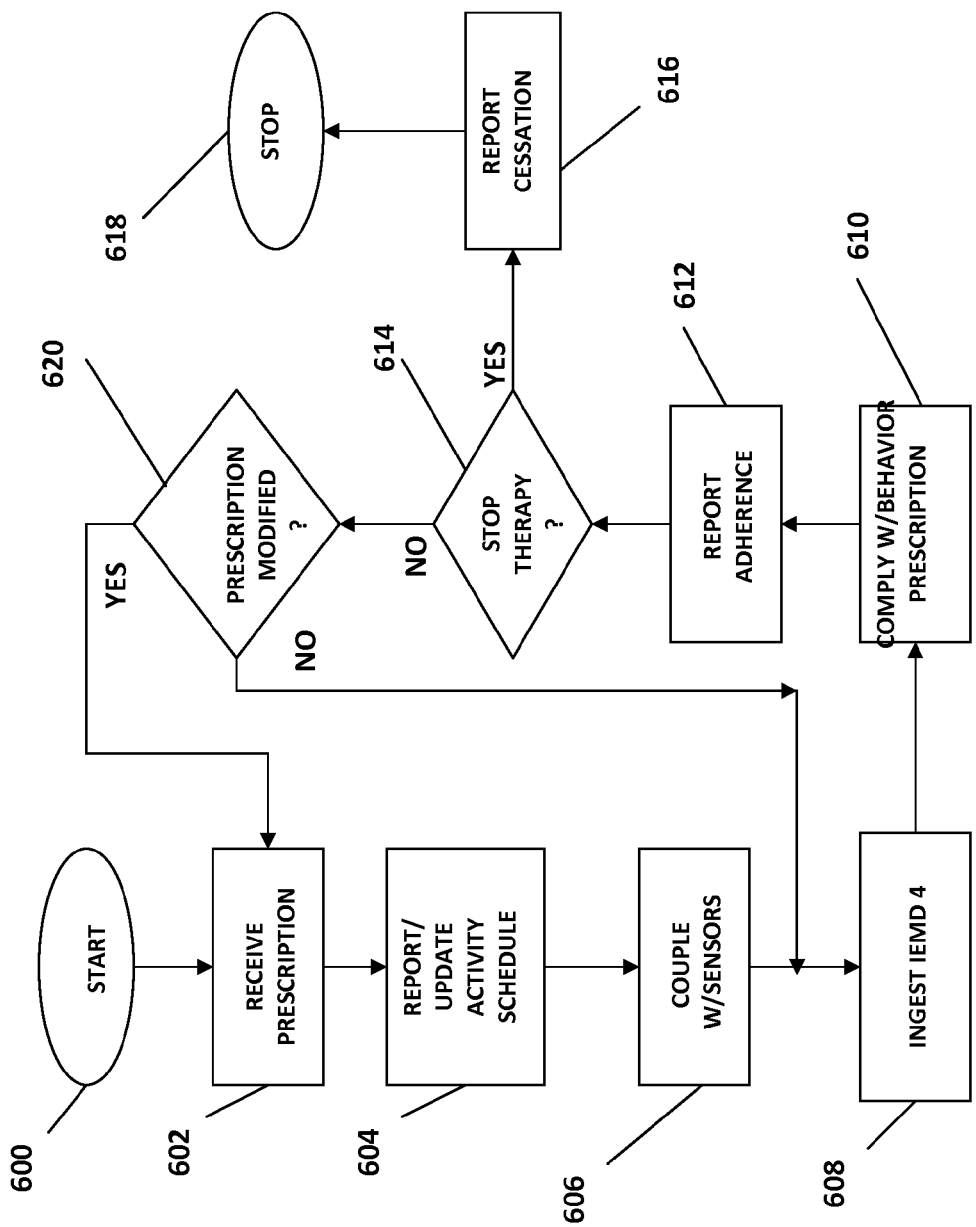
FIG. 6 is an illustration of other aspects of the method of the present invention, wherein certain behaviors of the patient and interaction of the patient with the patient management data system of FIGS. 1 and 2 is denoted.

Referring now generally to the Figures and particularly to FIG. 6, FIG. 6 is an illustration of other aspects of the method of the present invention, wherein certain behavior of the patient is denoted. In step 602 the patient receives a prescription of medications and behaviors. It is understood that a prescription of medication may include both the medication to be ingested and a schedule for ingesting the prescribed medications. The patient reports a schedule of expected activities via the patient input device 18 to the PMDS 10 in step 604. The schedule of expected activities, for example, may include work sessions, such as manual labor, expense report authoring, staff meetings, customer interaction periods, negotiations sessions, employee review meetings, sales forecast development, and presentations. The expected activities reported by the patient in step 604 are integrated into a patient record R.0 of the patient database 84 by means of the patient input device 18 and the network 2. The patient positions one or more sensors 20, 22, 23 and 24 in step 606 to enable the sensors 20, 22, 23 and 24 to detect one or more vital parameters of the patient. The patient ingests an IEMD 4 wherein the IEMD 4 transmits an ingestion report with a marker datum IEM M in step 608. The patient may further adhere to behaviors in step 612 as suggested in the prescription received in step 602, and report adherence in step 612 with suggested behaviors, to include one or more ingestions of an IEMD 4.

The patient may elect to cease following medical advice in step 614, and for example, to cease ingesting IEMD's 4, may proceed on to report cessation of adherence to the PMDS 10 by means of the patient input device 18 and the network 2 in step 616. The patient may cease implementing the prescriptive behaviors in step 618. Alternatively, the patient may determine to proceed from step 614 to step 620 and to query the PMDS 10 to determine whether the prescription assigned by the PMDS 10 has been modified. When the patient determines in step 620 that the assigned prescription has not been modified, the patient proceeds from step 620 back to step 608. When the patient determines in step 620 that the assigned prescription has been modified, the patient proceeds from step 620 back to step 602 to receive and review the modified assigned prescription.

Figure 7:
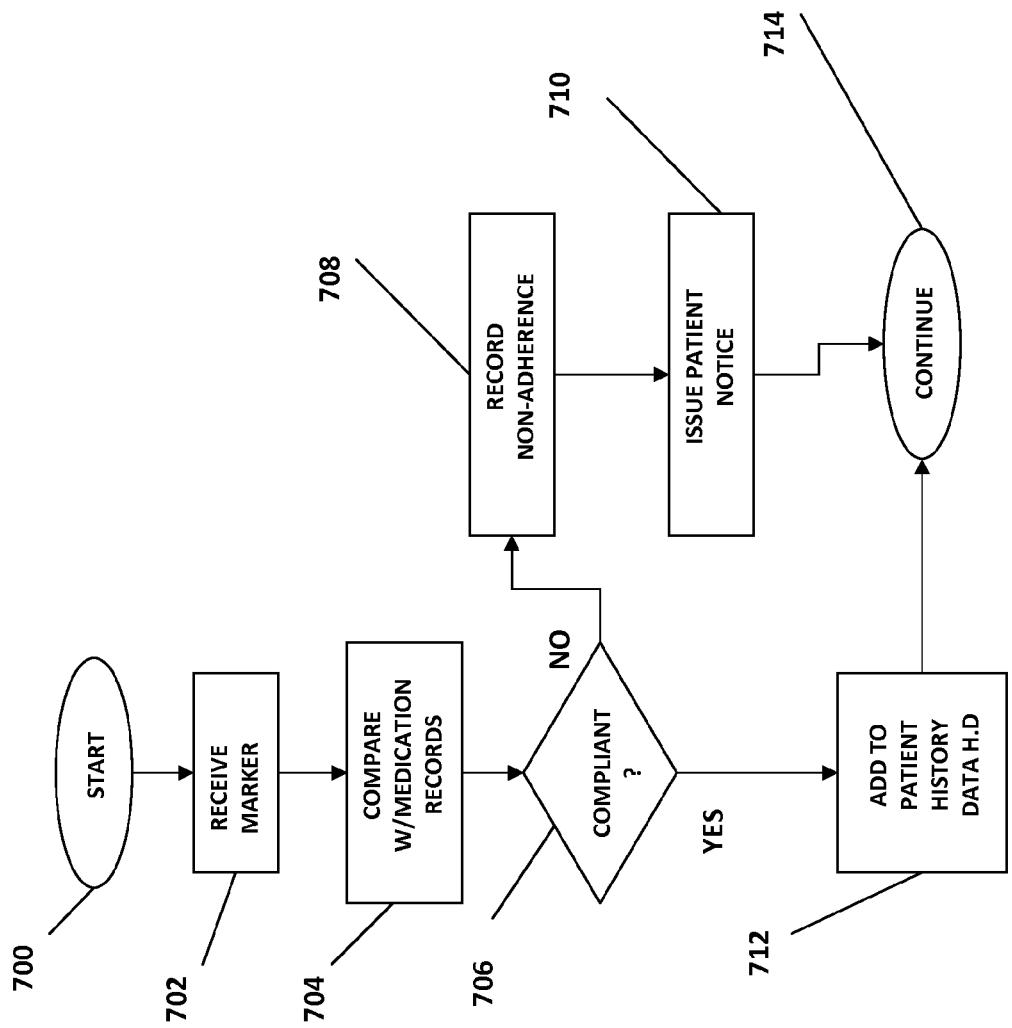
FIG. 7 is an illustration of a process implemented by the patient management data system of FIGS. 1, 2 and 3 in communication with the network, IEMD and sensors of FIG. 1.

Referring now generally to the Figures and particularly to FIG. 7, FIG. 7 describes a process implemented by the PMDS 10 in communication with the network 2, the sensors 20, 22, 23 and 24 and the IEMD 4. In step 702, the PMDS 10 receives a marker datum IEM M of an ingestion report transmitted from the IEMD 4. In step 704, the PMDS 10 compares the medicine identified by the marker datum IEM M and the time of receipt of the marker datum IEM M with the medication records R.0.MR.0-R.0.MR.N. The PMDS 10 determines in step 7.06 whether the marker datum IEM M received step 7.02 is compliant with a medication record R.0.MR.0-R.0.MR.N. When the PMDS 10 determines in step 7.06 that receipt of the marker datum IEM M of step 7.02 is noncompliant with a medication record R.0.MR.0-R.0.MR.N, the PMDS 10 records the instant receipt of the marker datum IEM M in the patient history data H.D as a noncompliant event and issues and transmits a patient notice of nonadherence in step 710 to the patient transceiver 8 and/or the patient input device 18. When the PMDS 10 determines in step 7.06 that receipt of the marker datum IEM M of step 7.02 is compliant with a medication record R.0.MR.0-R.0.MR.N, the PMDS 10 updates patient history data H.D in step 712 with a notation of adherence. The PMDS 10 proceeds from either step 710 or 712 to step 714 and to perform alternate computational operations.

Figure 8:
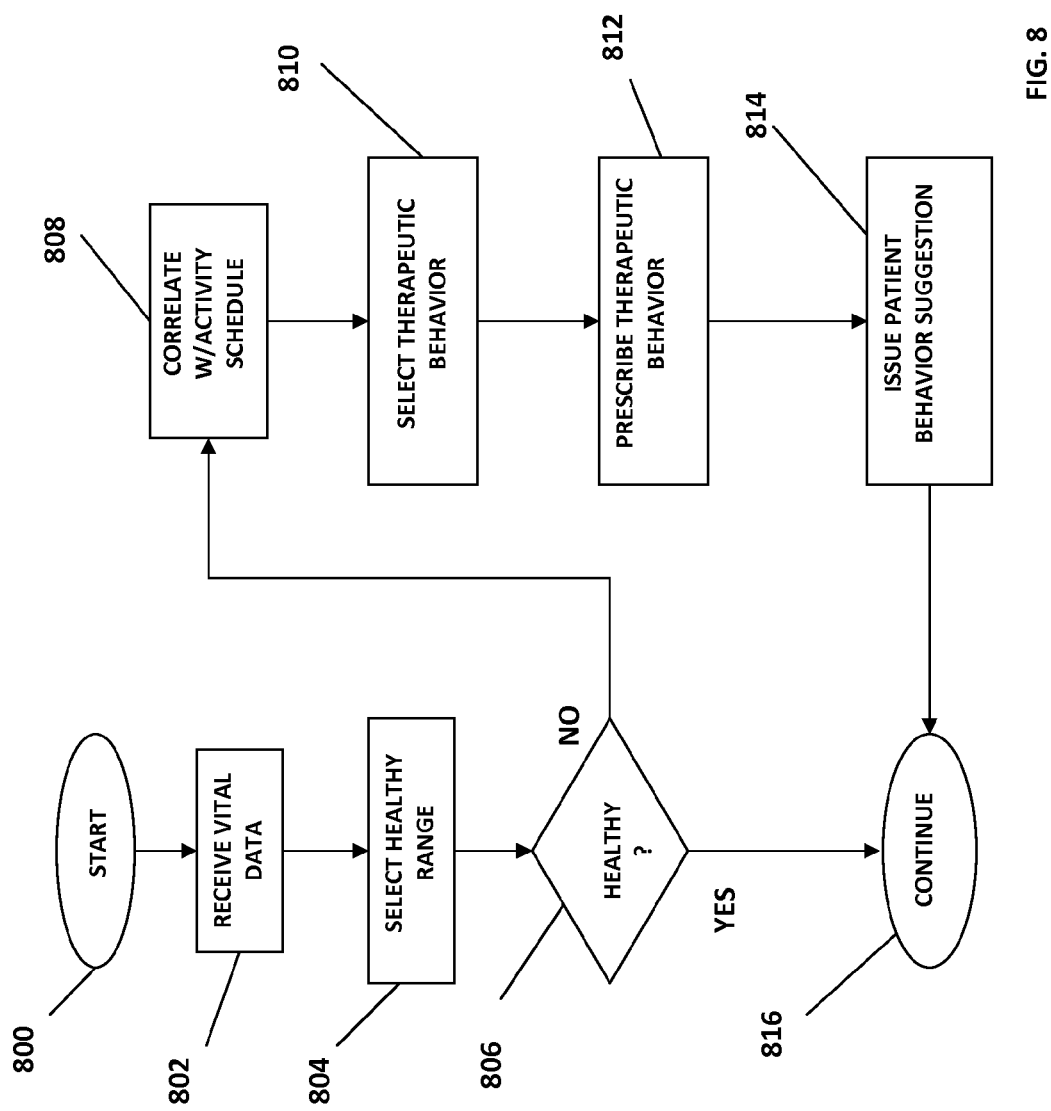
FIG. 8 is a process chart of a method in which a clinician or an expert system monitors a vital parameter of the patient and suggest via the network of FIG. 1 a therapeutic behavior intended to improve the health of the patient.

Referring now generally to the Figures and particularly to FIG. 8, FIG. 8 is a process chart of a method in which a clinician or an expert system monitors a vital parameter of the patient and suggest via the network 2 a therapeutic behavior intended to improve the health of the patient. In step 802 the PMDS 10 receives vital parameter data from one or more sensors 20, 22, 23 and 24. In step 804 the PMDS 10 compares the vital parameter data received in step 802 with a range of healthy values of the instant vital parameter, for example, heart rate, blood pressure, respiration rate, respiration intensity, and electrical skin conductivity. The PMDS 10 determines in step 806 whether the vital data received in step 802 falls within the healthy range of the instant vital parameter as stored in the PMDS 10 or elsewhere in the network 2. When the PMDS 10 determines in step 806 that the vital data received in step 802 does not falls within the healthy range of the instant vital parameter, the PMDS 10 proceeds from step 806 to step 808 and correlates the time of the receipt of the vital parameter data with the activity schedule of patient activity data R.ACT of one or more patient records R.0-R.N associated with the patient. In step 810 the PMDS 10 selects a therapeutic behavior intended to encourage the patient to maintain the vital parameter referenced in step 802 within the healthy range selected in step 802. The therapeutic behavior selected in step 810 may be provided by a clinician by input to the PMDS 10 or by means of the patient-messaging module 14. When the vital parameter referenced in step 802 is hypertension of the cardiovascular system, the selected therapeutic behavior may be or include, for example, listening to calming music, performing meditation, and/or physical exercise. In step 812 the therapeutic behavior is prescribed to the patient in view of a patient activity associated in the patient activity data R.ACT with the time of the receipt of the vital parameter data received in step 802. A patient behavior suggestion is transmitted from the PMDS 10 and/or the patient messaging module 14 in step 814, wherein the suggestion advises the patient to engage in the therapeutic behaviors selected in step 810 at times correlated with patient behavior correlated in step 808 and reported in the patient activity data R.ACT. The PMDS 10 proceeds from step 816 and to perform alternate or additional computational operations.

Figure 9:
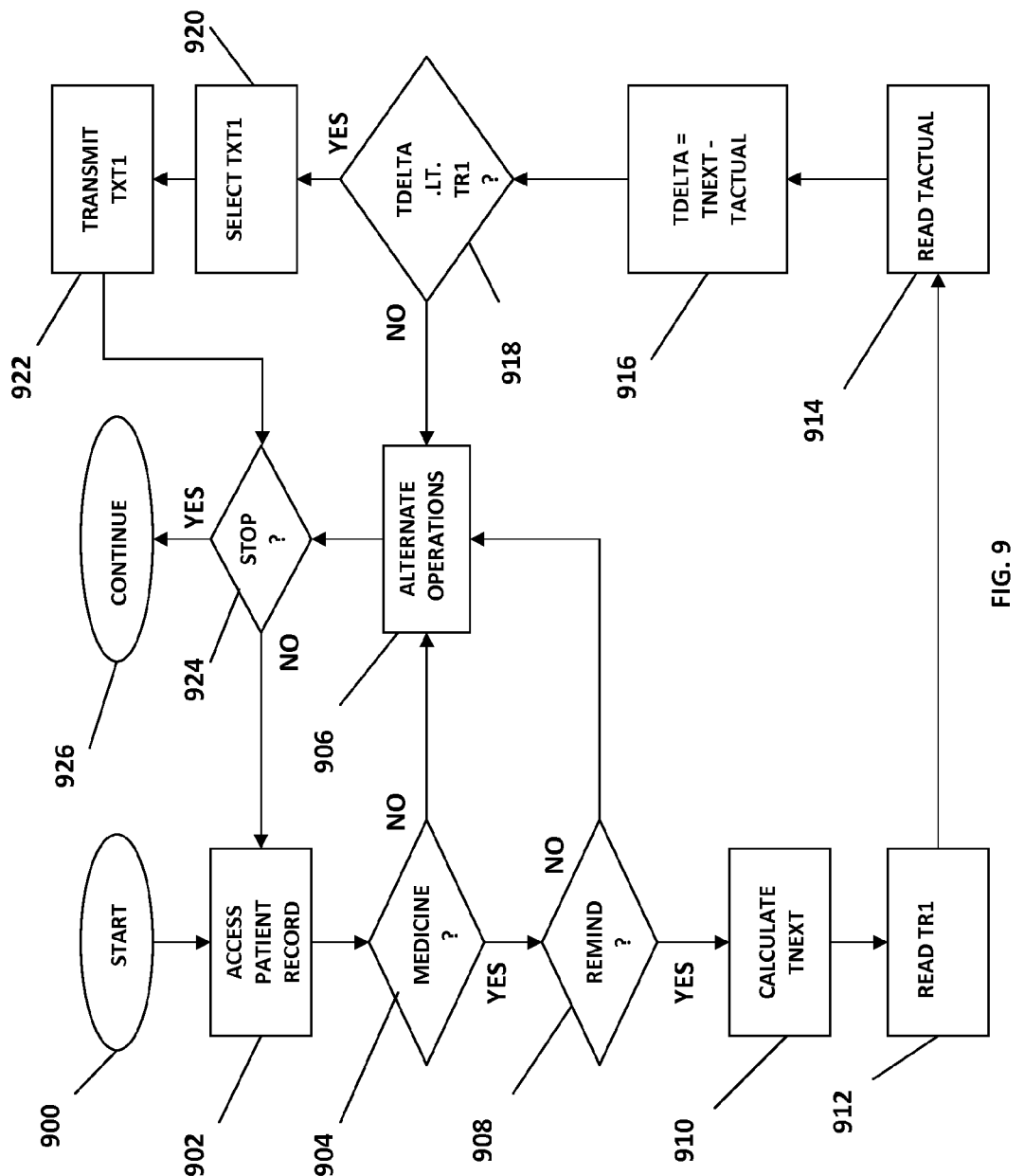
FIG. 9 is a process chart of a method of the patient management data system to determine if and when to send a text or audio message to the patient transceiver and/or the patient input device of FIG. 1.

Referring now generally to the Figures and particularly to FIG. 9, FIG. 9 is a process chart of a method of the PMDS 10 to determine if and when to send a text or audio message to the patient transceiver 8 and/or the patient input device 18. In step 902 the PMDS accesses one or more patient records R.0-R.N. The PMDS 10 determines in step 904 whether an ingestion of a medicine has been prescribed to the patient. When the PMDS determines in step 904 that the patient has not been prescribed to ingest a medication, the PMDS 10 proceeds on from step 904 to step 906 and to perform alternate or additional computational operations.

When the PMDS determines in step 904 that the patient has been prescribed in a medication record R.0.MR.0-R.0.MR.N of a patient record R.0-R.N to ingest an IEMD 4 containing a medication, the PMDS 10 proceeds on from step 904 to step 908, and to examine the first remind flag FLAG1 of the instant medication record R.0.MR.0-R.0.MR.N. When the first remind flag FLAG1 indicates an instruction to remind the patient of a recommended medication ingestions. When the first remind flag FLAG1 indicates an instruction to remind the patient of prescribed medicine ingestion recommendations, the PMDS 10 proceeds from step 908 to step 910. The PMDS 10 calculates the next scheduled time for an IEMD 4 ingestion in step 910 by analyzing information of the application schedule MED.S and calculates the next scheduled ingestion time TNEXT. The PMDS 10 reads the first remind time period TR1 from the medication record R.0.MR.0-R.0.MR.N accessed in step 908. The PMDS 10 accesses the real time clock 27 determines the current real time TACTUAL in step 914, and calculates the time difference TDELTA between the current time TACTUAL and the next scheduled ingestion time TNEXT. The PMDS 10 determines in step 918 whether the time difference TDELTA is less than the first remind time period TR1. When the PMDS 10 determines in step 918 that the time difference TDELTA is not less than the first remind time period TR1, the PMDS 10 proceeds from step 918 to step 906. When the PMDS 10 determines in step 918 that the time difference TDELTA is less than the first remind time period TR1, the PMDS 10 proceeds from step 918 to step 920 and selects the first remind text TXT1 from the medication record R.0.MR.0-R.0.MR.N accessed in step 908, and transmits the first remind text TXT1 to the patient transceiver 8 and/or the patient input device 18 in step 922.

The PMDS 10 proceeds from either step 922 or step 906 to step 924 and to determine whether to cease monitoring for transmissions of markers IEM M from the IEMD 4 and the sensors 20, 22, 23 and 24. When the PMDS 10 determines to continue monitoring the sensors 20, 22, 23 and 24 and for transmissions of markers IEM M from the IEMD 4, the PMDS 10 proceeds from step 924 to step 902. When the PMDS 10 determines to cease monitoring the sensors 20, 22, 23 and 24 and for transmissions of markers IEM M from the IEMD 4, the PMDS 10 proceeds from step 924 to step 926 perform alternate or additional computational operations.

Figure 10:
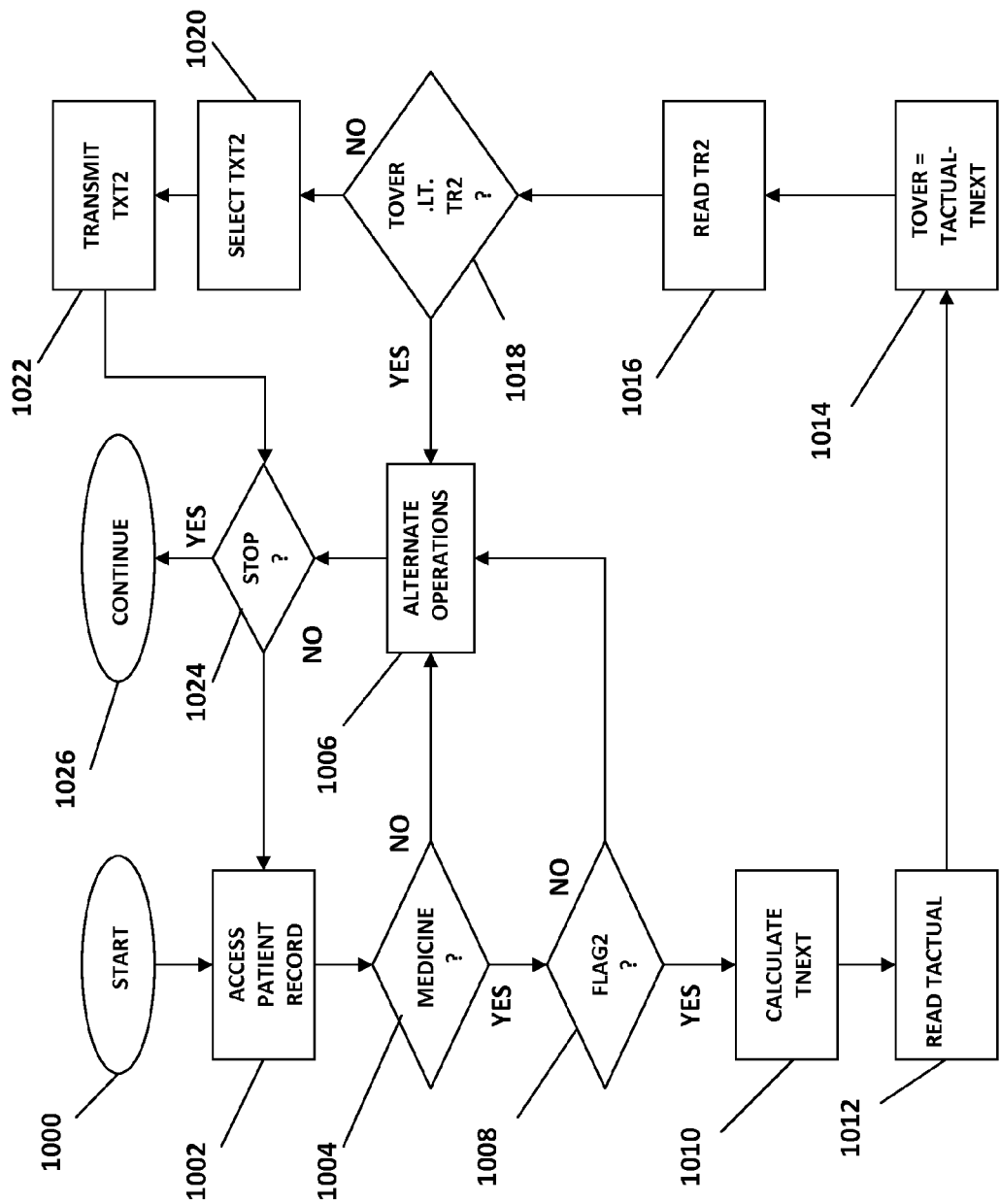
FIG. 10 is another process chart of a method of the patient management data system to determine if and when to send a text or audio message to the patient transceiver and/or the patient input device of FIG. 1.
Figure 11:
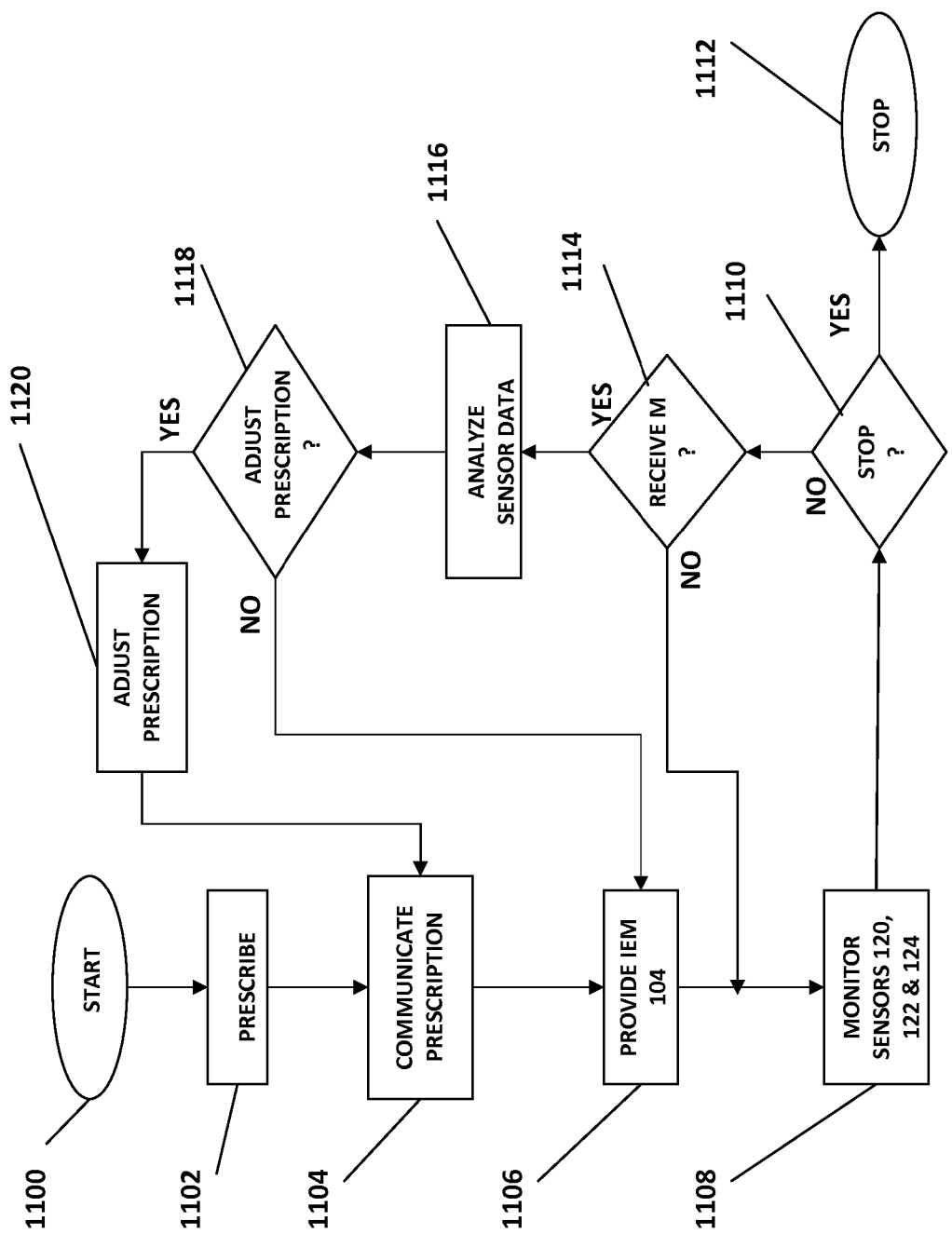
FIG. 11 shows an exemplary process flow.

Referring now generally to the Figures and particularly to FIG. 10, FIG. 10 is a process chart of a method of the PMDS 10 to determine if and when to send a text or audio message to the patient transceiver 8 and/or the patient input device 18 when an ingestion marker datum IEM M is not received approximately when a marker datum IEM M would be received when the IEMD 4 is ingested prescribed. In step 1002 the PMDS accesses one or more patient records R.0-R.N. The PMDS 10 determines in step 1004 whether an ingestion of a medicine has been prescribed to the patient. When the PMDS determines in step 1004 that the patient has not been prescribed to ingest a medication, the PMDS 10 proceeds on from step 1004 to step 1006 and to perform alternate or additional computational operations.

When the PMDS determines in step 1004 that the patient has been prescribed in a medication record R.0.MR.0-R.0.MR.N of a patient record R.0-R.N to ingest an IEMD 4 containing a medication, the PMDS 10 proceeds on from step 1004 to step 1008, and to examine the second remind flag FLAG2 of the instant medication record R.0.MR.0-R.0.MR.N. When the second remind flag FLAG2 indicates an instruction to remind the patient of a recommended medication ingestion when an ingestible event marker datum IEM M has not been received as would be when an IEMD 4 had been ingested as directed by the medication record R.0.MR.0-R.0.MR.N of step 1004. When the second remind flag FLAG2 indicates an instruction to remind the patient of a tardiness in following prescribed medicine ingestion as prescribed, the PMDS 10 proceeds from step 1008 to step 1010. The PMDS 10 calculates the next scheduled time for an IEMD 4 ingestion in step 1010 by analyzing information of the application schedule MED.S and calculates the next scheduled ingestion time TNEXT. The PMDS 10 accesses the real time clock 27 determines the current real time TACTUAL in step 1012, and calculates the time difference TOVER between the current time TACTUAL and the scheduled ingestion time TNEXT IN STEP 1014.

The PMDS 10 reads the second remind time period TR2 in step 1016 from the medication record R.0.MR.0-R.0.MR.N accessed in step 1008. The PMDS 10 determines in step 1018 whether the time difference TOVER calculated in step 1014 is less than the second remind time TR2 of step 1016. When the PMDS 10 determines in step 1018 that the time difference TOVER is less than the second remind time TR2, the PMDS 10 proceeds from step 1018 to step 1006. When the PMDS 10 determines in step 1018 that the time difference TDELTA is not less than the second remind time TR2, the PMDS 10 proceeds from step 1018 to step 1020 and selects the second remind text TXT2 from the medication record R.0.MR.0-R.0.MR.N accessed in step 1008, and transmits the second remind text TXT2 to the patient transceiver 8 and/or the patient input device 18 in step 1022.

The PMDS 10 proceeds from either step 1022 or step 1006 to step 1024 and to determine whether to cease monitoring for transmissions of markers M from the IEMD 4 and the sensors 20, 22, 23 and 24. When the PMDS 10 determines to continue monitoring the sensors 20, 22, 23 and 24 and for transmissions of markers M from the IEMD 4, the PMDS 10 proceeds from step 1024 to step 1002. When the PMDS 10 determines to cease monitoring the sensors 20, 22, 23 and 24 and for transmissions of markers M from the IEMD 4, the PMDS 10 proceeds from step 1024 to step 1026 perform alternate or additional computational operations.

Referring now generally to the Figures and particularly to FIGS. 2, 4A, 4B, 4C, and 4D, the audio/text converter module 64 is configured to convert digitized audio data received from the patient transceiver 8, the patient input device 18, the patient messaging module 14, the first network transceiver 12 and/or the second network transceiver 16 into textual data for storage in a patient record R.0, for example in the patient history data H.D, the patient activity data R.ACT, the first remind text TXT1, the second remind text TXT2, the first behavior remind text TXT1B and the second behavior remind text TXT2B, and/or the behavior description text BHR.D.

The audio/text converter module 64 is further configured to convert text data into digitized audio data representative of vocalizations of the source text data from the PMDS 10 and/or the patient messaging module 14 and for transmission of the digitized audio data representations to the patient transceiver 8 and/or the patient input module 18. The text data and the digitized audio data may be received via the bus 34 and from the system memory 28 or the network 102, or generated by the CPU 26.

Figure 12:
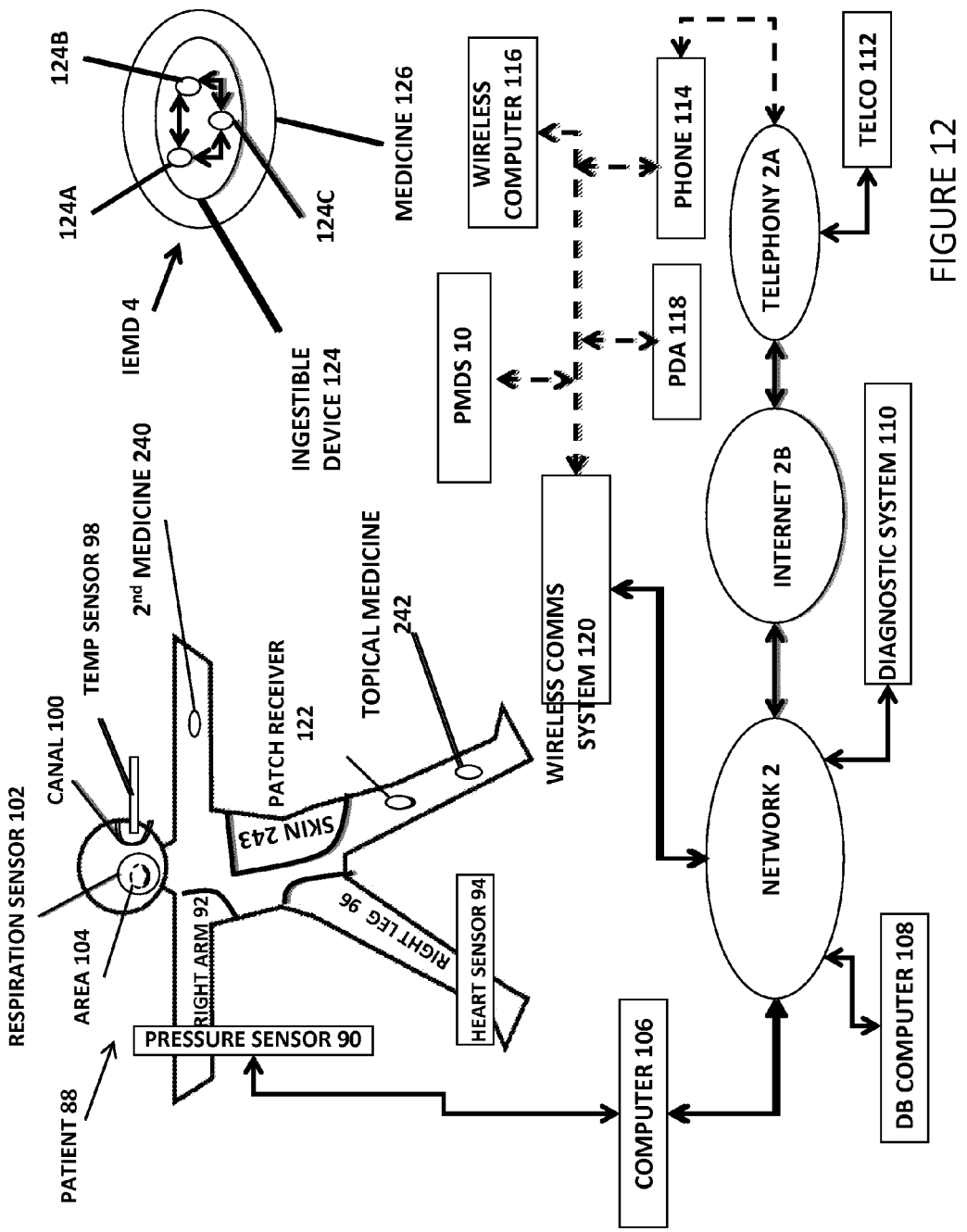
FIG. 12 is a schematic of a patient coupled with a plurality of biometric sensors and in communication with a cellular telephone, other mobile computational devices and information technology networks.

Referring now generally to the Figures and particularly to FIG. 12, FIG. 12 is a schematic of a patient coupled with a plurality of biometric sensors and in communication with a cellular telephone, other mobile computational devices and information technology networks. In one example, it is a schematic of a patient 88 with a blood pressure sensor 90 wrapped around a right arm 92, a wireless heart rate sensor 94 in contact with a right leg 96, a wireless body temperature sensor 98 positioned within a left ear canal 100, and a respiration monitor 102 positioned at a patient's mouth and nose area 104. These sensors are bi-directionally communicatively coupled to a first network computer 106. To illustrate, biometric data may include body related data, e.g., temperature, ph factor, pulse rate, and ingestion data may include event and/or medication related data, e.g., nature, type of medication, dosage, time at which ingestion took place, adherence to prescription, level of adherence to prescription, etc., communicated to a wireless communications device or receiver, e.g., computer, patch receiver, etc. The biometric data may include, for example, a unique identifier which may be compared to various data, e.g., genetic profile data, emotional data, and other data. Such data may be associated with one or more of a variety of devices, e.g., cellular phone, wireless computer, PDA, and wireless comms system or receiver for validation purposes.

A database computer 108, or "DB computer" 108, and a medical diagnostic computational system 110 (hereinafter, "diagnostic system" 110) are bi-directionally communicatively coupled with the network 2. A software-encoded database may be associated with the database computer 108 and may include current and historical data pertaining to the patient 88. The historical data includes, for example, medical record(s), health record(s), or medical chart(s) which are systematic documentation of a patient's medical history and care. The term "medical record" is used both for the physical information for the patient and for the body of information which comprises the total of each patient's health history. The network 2 is bi-directionally and communicatively coupled with a telephonic network, represented by telephony network 2A and with other forms of telecommunication devices, e.g., fax etc, represented by, telecommunications network 112 (hereinafter "TELCO" 112).

Communication devices, for example, a digital cellular telephone 114, a wireless enabled network computer 116 and a wireless enabled personal digital assistant (PDA) 118 are further bi-directionally communicatively coupled with the network 2 via a wireless communications system 120 (hereinafter "wireless comms system" 120). It is understood that the definition of the term "computer" as used in the present disclosures includes, for example, digital cellular telephones, personal digital assistants, network computer, computer workstations, automated database systems, servers, and web servers.

In another aspect, one or more sensors 20, 22, 23, 24, 94, 98, and/or 102 may be conductively or communicatively coupled to a patch receiver 122, positioned on the skin or subcutaneously or as a wristband or any such wearable device. The patch receiver 122 in turn may be communicatively coupled to the first network computer 106. The first network computer 106 is bi-directionally communicatively coupled to electronics communications network 2. The network 2 may further facilitate a two-way communication with the Internet 2B.

An IEMD 4 optionally includes a medicine 126. The IEMD 4 is an in-body device as disclosed herein. Examples of in-body devices include, but are not limited to: implantable devices, e.g., implantable therapeutic devices, such as but not limited to stents, drug delivery devices, orthopedic implants, implantable diagnostic devices, e.g., sensors, biomarker recorders, etc.; ingestible devices such as the IEMD 4 described in the preceding references; etc.

In various aspects, the biometric data may be communicated to and/or from one or more receiving devices (not shown), for example, a biometric data receiver such as the computer 106, etc. The biometric receiver 106, 114, 116, 118 and 120 may be embodied in various ways, for example, as the cellular telephone 114, the wireless computer 116, the personal digital assistant 118, and/or a personal receiver such as an implantable receiver, a semi-implantable receiver, and an externally applied device such as the personal signal patch receiver 122. The patch receiver is a personal receiver that may be removably affixed to the person's person, apparel, or personal equipment, for example, by an adhesive, a clip, a fabric, or other suitable attachment means known in the art.

To illustrate one exemplary application of the method of the present invention, a patient 88 may ingest the IEMD 4 integrated with medicine 126. The IEMD 4 may communicate data that includes biometric data and ingestion data. The biometric data may include body related data, for example, temperature, pH factor, pulse rate, and ingestion data may include event and/or medication related data, for example, nature, type of medication, dosage, time at which ingestion took place, adherence to prescription, level of adherence to prescription, etc., communicated to a wireless communications device 114, 116, 118, and 120, or receiver, for example, computer 106, patch receiver, etc. The biometric data may include, for example, a unique identifier which may be compared to various data, for example, genetic profile data, emotional data, and other data. Such data may be associated with one or more of a variety of devices, for example, the cellular phone 114, the wireless computer 116, PDA 118, and the wireless comms system 120 or receiver for validation purposes.

The biometric data reception may be affected or effected by one or more receiving devices, for example, personal signal receivers such as patch receivers that are removably attachable externally to the patient 88 or a non-human body; or comprised within a subcutaneous device, an implantable devices, and/or various external devices, for example, devices which are or are not designed for attachment or other permanent or semi-permanent contact with the body, for example, the cellular telephone 114. An ingestible event marker system is described in the Patent Application PCT/US2008/52845 and includes an IEMD 4 and a personal patch signal receiver 122. The patch receiver 122 includes, for example, devices capable of at least receiving data and/or signals, etc. Patch receivers 122 may be attachable, for example, permanently or removably attachable externally to a human body or a non-human body. For example, the patch receiver 122 may include the receiver and an adhesive layer to provide for attachment to and removal from the patient 88. Alternatively, the patch receiver 122 may be implantable or semi-implantable, for example, subcutaneous implantation.

The wireless communications system 120, the cellular telephone 114, the wireless computer 116, and/or the personal digital assistant 118, may include systems, subsystems, devices, and/or components that receive, transmit, and/or relay the biometric data. In various aspects, the wireless communications system 120 communicably interoperates with a receiver 37 such as the patch receiver 120 and a communications network 2 such as the Internet 2B. Examples of wireless comms systems 120 are computers, for example, servers, personal computers, desktop computers, laptop computers, intelligent devices/appliances, etc., as heretofore discussed.

In various aspects, the wireless communications system 120 may be embodied as an integrated unit or as distributed components, for example, a desktop computer and a mobile telephone in communication with one another and in communication with a patch receiver and the Internet 2B.

Further, various aspects of the network include combinations of devices. For example, one such combination is a receiver 122 such as the patch receiver 122 in communication with the portable digital assistant 118 or the mobile telephone 114. Thus, for example, the patch receiver 122 wirelessly transmits biometric data received from the IEMD 4 to the cellular telephone 114 having a receiver and a software agent available thereon. The cellular telephone 114 receives the biometric data transmitted by the IEMD 4. In one scenario, the patient 88 ingests prescription medication 126 in conjunction with an IEMD 4. The IEMD 4 identifies various information, for example, the medication type and dosage and transmits this information in a biometric data transmission via, for example, a conductive transmission to the patch receiver 120, which may be removably attached to the patient 88. The patch receiver 122 transmits the biometric data to, for example, the cellular telephone 114, the wireless computer 116, the personal digital assistant 118, and/or the wireless comms device 120 as the case may be.

For ease of description, the in-body devices of the invention will now be further described in terms of configurations having current path extender capabilities such as those provided by a skirt (not shown) where the skirt is part of the IEMD 4, for example, the wireless IEMD 4. One or more IEMD 4 may be or comprise a composition that includes in certain configurations a vehicle, where the vehicle may or may not include an active agent such as the medicine 126.

IEMDs 4 of interest include those described in PCT Application No. PCT/US2006/016370 filed on Apr. 28, 2006 titled "Pharma-Informatics System"; PCT Application No. PCT/US2007/022257 filed on Oct. 17, 2007 titled "In-vivo Low Voltage Oscillator for Medical Devices"; PCT Application No. PCT/US2007/82563 filed on Oct. 25, 2007 titled "Controlled Activation Ingestible Identifier"; U.S. patent application Ser. No. 11/776,480 filed Jul. 11, 2007 titled "Acoustic Pharma Informatics System"; PCT/US2008/52845 filed on Feb. 1, 2008 titled "Ingestible Event Marker Systems"; Patent Application No. PCT/US08/53999 filed Feb. 14, 2008 titled "In-Body Power Source Having High Surface Area Electrode"; U.S. patent application Ser. No. 12/238,345 filed Sep. 25, 2008 titled "In-Body Device With Virtual Dipole Signal Amplification, the disclosures of which applications are herein incorporated by reference.

The IEMD 4 communicates, e.g., generates, alters, produces, emits, etc., a communication upon contact of the IEMD 4 with a target physiological location (or locations) depending on the particular configuration of the IEMD 4. The IEMD 4 of the present compositions may vary depending on the particular configuration and intended application of the composition.

As such, variations of IEMDs 4 may communicate, for example, communicate a unique identifier, when activated at a target site, for example, when the instant IEMD 4 contacts a target surface or area within the patient's body 6, for example, a physiological, site and/or alters a current when in contact with a conducting fluid, for example, gastric acid in the stomach. Depending on the configuration, the target physiological site or location may vary, where representative target physiological sites of interest include, for example, but are not limited to: a location in the alimentary system, such as the mouth, esophagus, stomach, small intestine, large intestine, etc.

In certain configurations, the IEMD 4 is configured to be activated upon contact with fluid at the target site, for example, stomach fluid, regardless of the particular composition of the target site. In some configurations, the IEMD 4 is configured to be activated by interrogation, following contact of the composition with a target physiological site. In some configurations, the IEMD 4 is configured to be activated at a target site, wherein the target site is reached after a specified period of time.

Depending on the needs of a particular application, the communication of an ingestible event marker datum IEM M associated with the event marker IEMD 4, for example, altered current, an RFID signal, etc., may be generic such as a communication that merely identifies that the composition has contacted the target site, or may be unique, for example, a communication which in some way uniquely identifies that a particular event marker datum IEM M from a group or plurality of different markers M in a batch has contacted a target physiological site.

As such, the IEMD 4 may be one that, when employed with a batch of unit dosages, for example, a batch of tablets, is associated with a communication which cannot be distinguished from the signal emitted by the IEMD 4 of any other unit dosage member of the batch. In yet other configurations, each member of the batch has an IEMD 4 that is associated with a unique communication, at least with respect to all the other ingestible event markers of the members of the batch. For example, each wireless ingestible device IEMD 4 of the batch emits a signal that uniquely identifies that particular wireless ingestible device in the batch, at least relative to all the other ingestible event markers M of the batch and/or relative to a universe of ingestible event markers M. In one configuration, the communication may either directly convey information about a given event, or provide an identifying code, which may be used to retrieve information about the event from a database, for example, a database linking identifying codes with compositions.

The IEMD 4 may generate a variety of different types of signals as a marker datum IEM M, including, for example, but not limited to: RF signals, magnetic signals, conductive (near field) signals, acoustic signals, etc. Of interest in certain configurations are the specific signals described in the PCT application serial no. PCT/US2006/16370 filed on Apr. 28, 2006; the disclosures of various types of signals in this application being specifically incorporated herein by reference. The transmission time of the IEMD 4 may vary, where in certain configurations the transmission time may range from about 0.1 microsecond to about 48 hours or longer, for example, from about 0.1 microsecond to about 24 hours or longer, for example from about 0.1 microsecond to about 4 hours or longer, for example from about 1 sec to about 4 hours, including from about 1 minute to about 10 minutes. Depending on the given configuration, the IEMD 4 may transmit a given signal once. Alternatively, the IEMD 4 may be configured to transmit a signal with the same information, for example, identical signals, two or more times, where the collection of discrete identical signals may be collectively referred to as a redundant signal.

Various configurations of elements are possible, e.g., dissimilar materials 124A, 124B. When in contact with a conducting fluid, a current is generated. A control device 124C may alter the current. The altered current may be detectable, for example, by a receiving device, etc., and associated with a communication providing a unique IEM, etc., as previously discussed. The dissimilar materials making up the electrodes can be made of any two materials appropriate to the environment in which the identifier will be operating. The dissimilar materials are any pair of materials with different electrochemical potentials. For example, in some configurations where the ionic solution comprises stomach acids, electrodes may be made of a noble metal, e.g., gold, silver, platinum, palladium or the like, so that they do not corrode prematurely. Alternatively, for example, the electrodes can be fabricated of aluminum or any other conductive material whose survival time in the applicable ionic solution is long enough to allow the identifier to perform its intended function. Suitable materials are not restricted to metals, and in certain configurations the paired materials are chosen from metals and non-metals, for example, a pair made up of a metal (such as Mg) and a salt. With respect to the active electrode materials, any pairing of substances, for example, metals, salts, or intercalation compounds, that have suitably different electrochemical potentials (voltage) and low interfacial resistance are suitable.

Various other configurations may include other communication-related components, for example, an RFID signal generator, etc.

In various aspects, the IEMD 4 communicates an ingestion alert when the medicine 126 is dissolved within a gastrointestinal pathway of the patient 88. The IEMD 4 is configured to transmit the ingestion alert as a wireless transmission that is detectable by, for example, the cellular telephone 114, the wireless enabled network computer 116, the wireless enabled personal digital assistant 118, and/or the wireless comms system 120. In addition, the wireless heart rate sensor 94, the wireless body temperature sensor 98, and/or the respiration monitor 16 are optionally configured to transmit biometric measurements in a wireless transmission that is detectable by, for example, the cellular telephone 114, the wireless enabled network computer 116, the wireless enabled personal digital assistant 118 and/or the wireless comms system 120. The wireless transmissions, for example, of the IEMD 4, the wireless heart rate sensor 94, the wireless body temperature sensor 98, and/or the respiration monitor 102 alternately or additionally are or comprise radio frequency wave or pulse transmissions and/or light wave or pulse transmissions.

Information regarding alternate configurations of the pharmaceutical composition 40 and the IEMD 4 are disclosed in United States Patent Application Publication No. 20080284599, published on Nov. 20, 2008 titled "Pharma-Informatics System", which is incorporated by reference in its entirety and for all purposes in this document.

Figure 13:
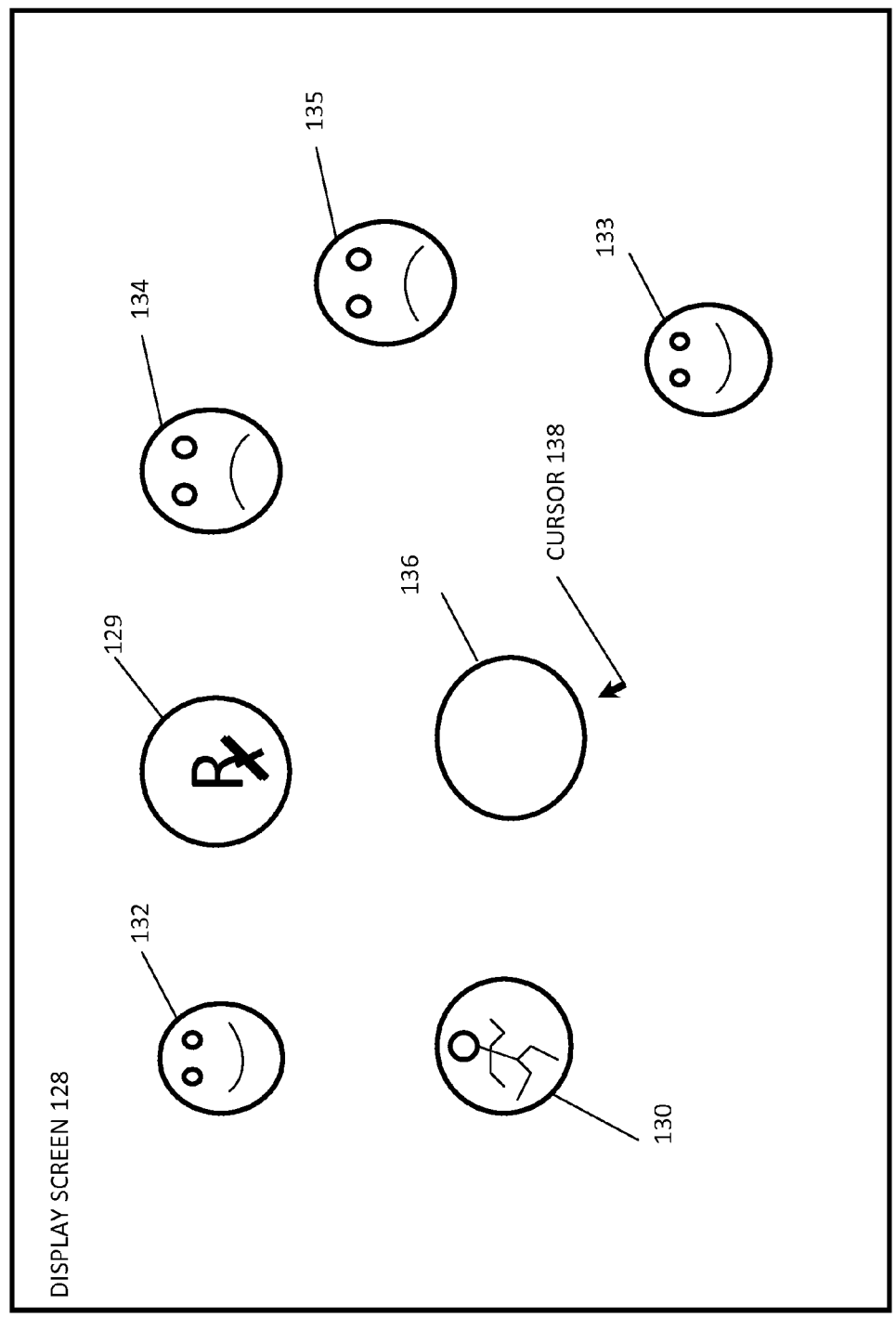
FIG. 13 is an illustration of a display screen of the cellular telephone of FIG. 12 displaying icons.

Referring now generally to the Figures and particularly to FIG. 13, FIG. 13 is an illustration of a display screen 128 of the cellular telephone 114, the wireless enabled network computer 116 and/or the wireless enabled personal digital assistant 118 wherein a plurality of icons 129-136 are available for user selection. In one configuration, the display screen 128 is a touch screen and the icons 129-136 are selected by the application of the patient 88 of finger pressure or body heat. In other configurations, alternately or additionally the patient 88 may select one or more icon by positioning a cursor 138 over an icon 129-136 and selecting the icon 129-136 over which the cursor 138 is positioned by means of an input device 140 of, for example, the cellular telephone 114, the wireless enabled network computer 116 and/or the wireless enabled personal digital assistant 118. The medicine cursor 138 is selected by the patient 88 to indicate a taking of the medicine 126, for example by an oral or nasal ingestion of one or more pharmaceutical compositions 122, a topical application of the medicine 126, or injection or other introduction of the medicine 126 to the patient 88. Accomplishment icon 130 is selected by the patient 88 to indicate an achievement or an engagement in an activity, for example an athletic session, exercise or event, a hobby, a meditation session, a therapeutic practice or exercise, a leisure activity, a recreational activity, a rehabilitative activity, a period of sleep, a meal consumption, a liquid ingestion, an erotic thought, erotic act, or an occurrence of an aspect of menstruation.

Each emotion icon 129-136 is selected by the patient 88 to indicate a perception of an associated emotion or a psychological state by the user, for example an emotion or psychological state of happiness, appreciation, kindness, love, joy, fondness, bliss, anger, fear, dread, loathing, anxiety, jealousy, envy, contempt, resentment, perceived pain, perceived pleasure, confidence, insecurity, optimism, pessimism, patience, impatience, attraction, repulsion, clarity, confusion, encouragement, discouragement, a romantic sensation, a sexual arousal, or an erotic sensation. Each sad icon 134-135 is selected by the patient 88 to report an occurrence of an undesirable event or condition, for example nausea, diarrhea, anxiety, physical pain, bleeding, or a loss of balance. An external icon 136 may be selected by the patient 88 to indicate a perception of an event or condition external to the patient 88, for example an inbound phone call or a visit from a friend. It is understood that each icon 129-136 may be individually associated with a single emotion, perception, event, process or condition.

Figure 14:
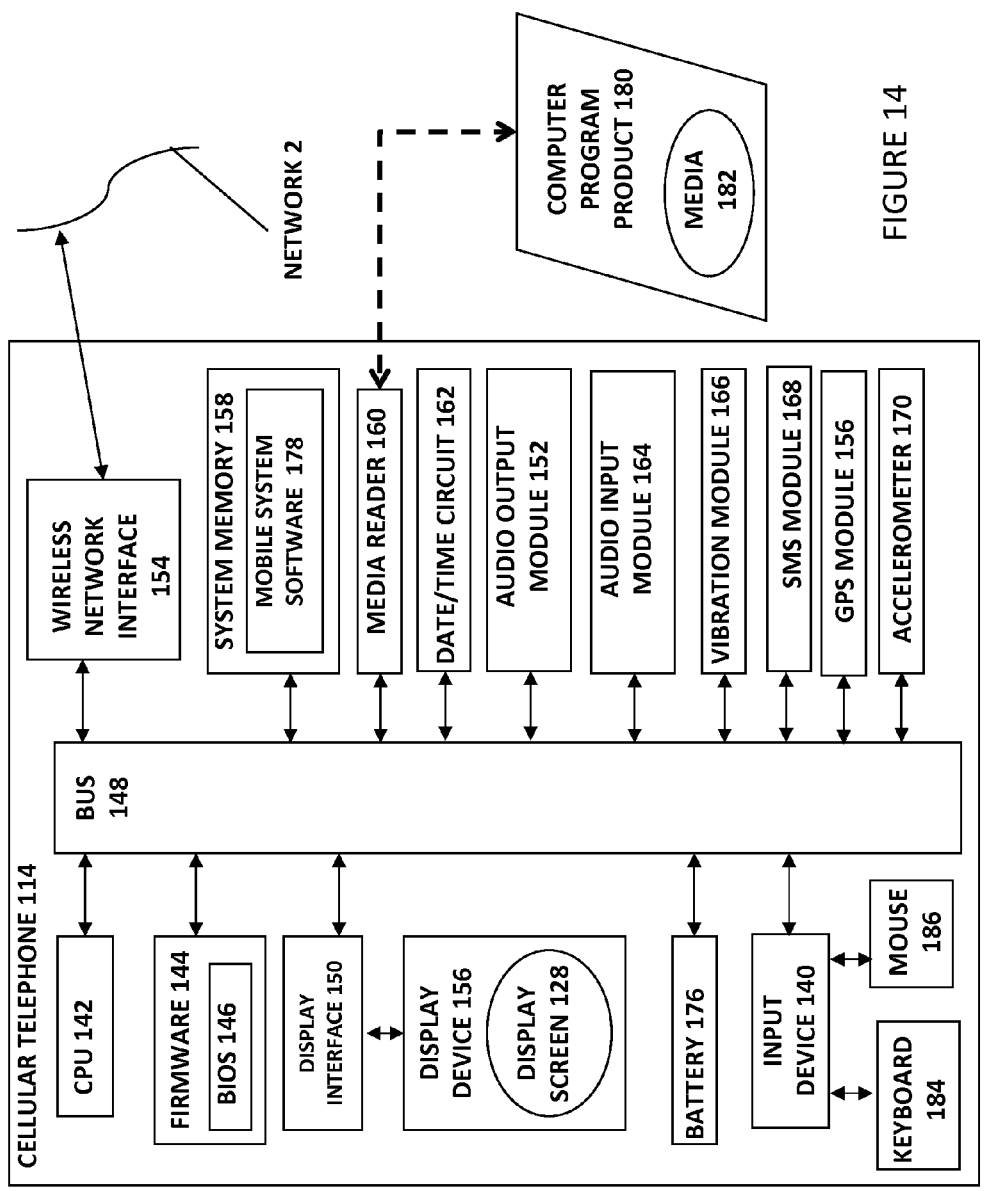
FIG. 14 is a schematic diagram of the cellular telephone of FIGS. 12 and 13.

Referring now generally to the Figures and particularly to FIG. 14, FIG. 14 is a schematic diagram of the cellular telephone 114. It is understood that the network computer 106, the wireless enabled network computer 116, the wireless enabled personal digital assistant 118 and the wireless comms system 120 may comprise one or all of the elements of the cellular telephone 114.

The cellular telephone 114 includes a central processing unit 142, or "CPU" 142 and a firmware 144. The firmware 144 further includes a set of software-encoded instructions comprising a mobile basic input output system 146 used to boot-up the cellular telephone 114. A power and communications bus 148 (or "mobile bus" 148) bi-directionally communicatively couples the CPU 142, the firmware 144, a display device interface 150, the input device 140, a telephone audio output module 152, a wireless network interface 154, a global positioning system module 156, a telephone system memory 158, a telephone media writer/reader 160, a date time circuit stamp 162, a telephone audio input module 164, a telephone mechanical vibration module 166, a small message service module 168, and an accelerometer 170.

The display interface 150 bi-directionally communicatively couples a display module 172 comprising a telephone display screen 174 with the communications bus 148. The telephone audio output module 152 accepts digitized information from the bus 148 and derives and generates an audible sound wave output therefrom.

An electrical power battery 176 provides energy to the elements 142-174 of the cellular telephone 114 via the mobile bus 148.

The wireless network interface 154 bi-directionally communicatively couples the electronics communications bus 146 and the network 2. The system memory 158 is a random only access memory wherein a mobile telephone system software 178 is maintained and optionally edited or modified by deletion, addition or update of software-encoded instructions.

The global positioning system module GPS (hereinafter "GPS module" 156) is a communications device that communicates with a global positioning system that comprises earth-orbiting satellites and allows the GPS module 156 to determine coordinates of the location of the GPS module 156 on the earth's surface.

The date/time circuit 162 is bi-directionally communicatively coupled with the communications bus 148 and provides a digitized date time stamp data when polled by the telephone CPU 142. The date/time circuit 162 further generates time pulses and synchronizing signals that the telephone CPU 142 and the cellular telephone 114 generally, apply to measure the passage of time, time period durations, and to schedule alarms and alerts.

The telephone media writer/reader 160 is configured to read, and optionally write, machine readable, computer executable software encoded instructions from a computer program product 180. The telephone media writer/reader 160 and the associated computer program product 180 are selected and configured to provide non-volatile storage for the cellular telephone 114. Although the description of computer program product 180 contained herein refers to a mass storage device, for example a hard disk or CD-ROM drive, it should be appreciated by those skilled in the art that computer program product 160 can be any available media that can be accessed by the digital telephone 114.

By way of example, and not limitation, computer program product 180 may be or comprise computer operable storage medium 182 and communication media. Computer operable storage media 182 include, for example, volatile and non-volatile, removable and non-removable media implemented in any method or technology for storage of information such as computer-readable instructions, data structures, program modules or other data. Computer operable storage media include, for example, but are not limited to, RAM, ROM, EPROM, EEPROM, flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the cellular telephone 144.

The computer program product 180 may comprise machine-readable instructions within a computer operable storage medium which when executed by the computer to cause the computer to perform one or more steps as described in the Figures and enabled by the present disclosure, and/or generate, update, maintain and apply one or more data structures.

The input device 140 may be or comprise a character input keypad 184 and/or a mouse 186, or other point and click selection or data input device known in the art.

Figure 15:
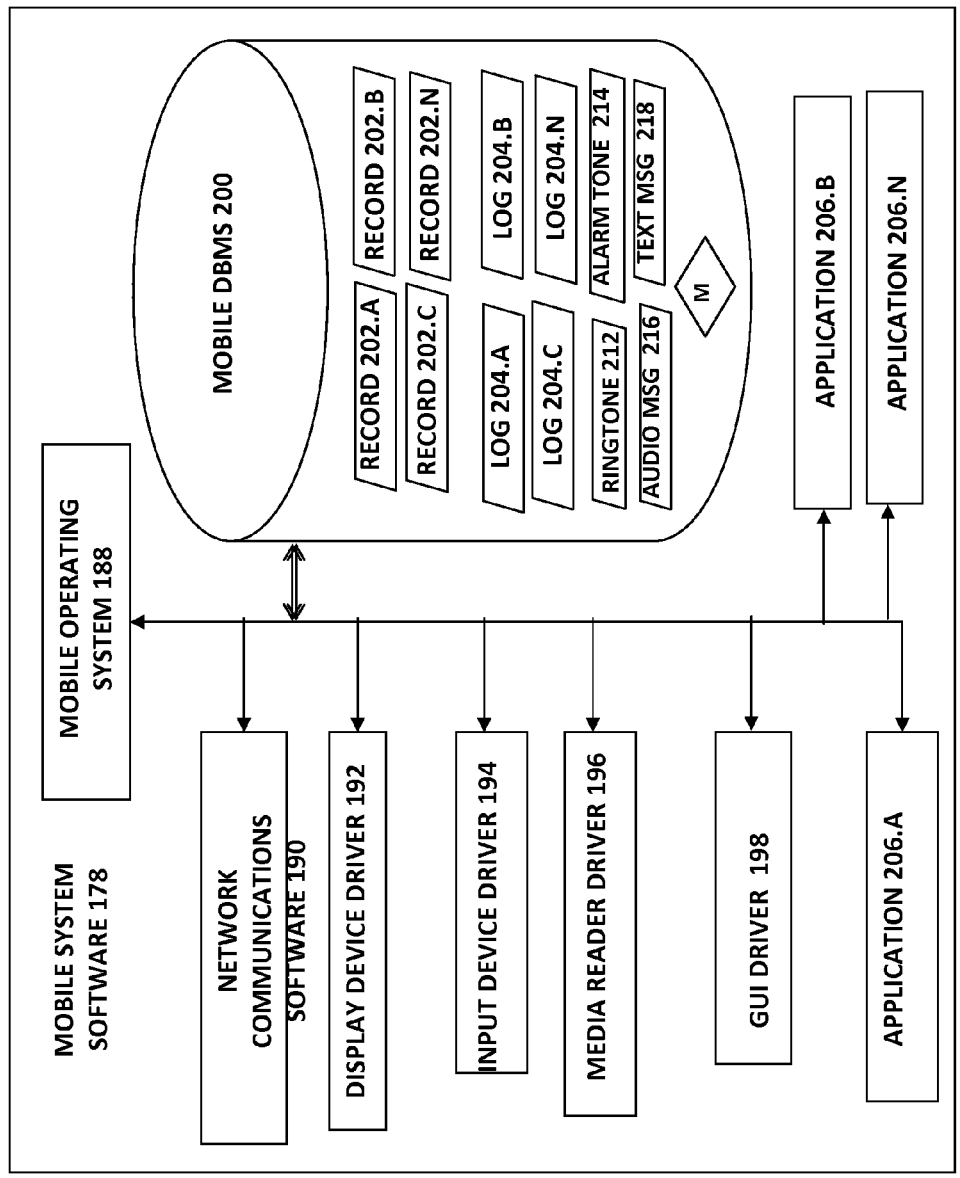
FIG. 15 is a schematic diagram of a mobile phone system software of the cellular telephone of FIGS. 12, 13 and 14.

Referring now generally to the Figures and particularly to FIG. 15, FIG. 15 is a schematic diagram of the mobile telephone system software 178 of the cellular telephone 114. A mobile device operating system 188 acts as a control layer between the hardware elements 142-186 of the cellular telephone 114 and the mobile system software 178 of the cellular telephone 114. A network communications software 190 enables the wireless network interface 154 to bi-directionally couple the network 2 with internal communications bus 148 and the CPU 142. A mobile display device driver 192 enables the CPU 142 to direct the state of the telephone display screen 128 to include the rendering of the icons 129-136. A mobile input device driver 194 enables the CPU 142 to accept, execute and interpret commands, instructions, data and selections from the input device 140. A mobile reader driver 196 enables the CPU 140 to accept, execute and interpret software encoded programs, commands, instructions, data and selections from the computer program product 180. A graphical user interface driver 198, or "mobile GUI" 198, enables the cellular telephone 114 to visually render data, for example, to render the icons 129-136.

The mobile telephone system software 178 further includes a data base management system 98 (hereinafter, "mobile DBMS" 200) storing a plurality of records 202.A-202.N. and a plurality of logged event data 204.A-204.N (hereinafter, "log" 204.A-205.N). The system software 178 further comprises a plurality of software applications 206.A-206.N.

Figure 16:
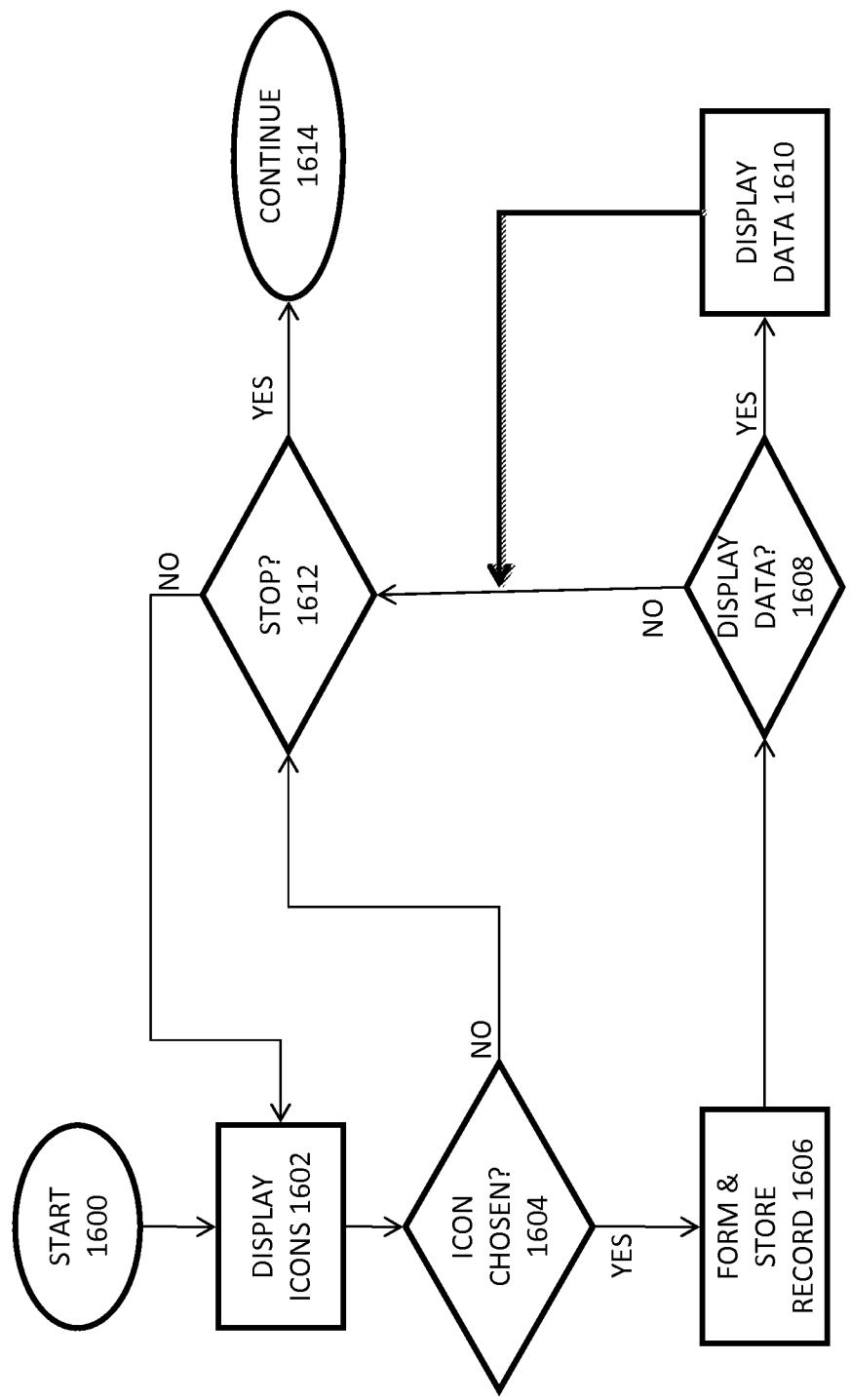
FIG. 16 illustrates a first disclosed exemplary additional or alternate process, wherein the cellular telephone of FIG. 12-15 displays one or more icons of FIG. 13.

Referring now generally to the Figures and particularly to FIG. 16, FIG. 16 illustrates a first aspect of a method wherein an exemplary process is represented. In the process of FIG. 16, the cellular telephone 114 powers up in step 1600 and displays one or more icons 129-136 in step 1602. The computer determines in step 1604 whether the patient 88 has selected an icon 129-136. When the cellular telephone 114 determines in step 1604 that the patient 88 has selected an icon 129-136, the cellular telephone 114 proceeds on to step 1606 to form an exemplary record 202.A and store the record 202.A in the DBMS 188, wherein the record 202.A includes an icon identifier and a date/time stamp data generated by the date time circuit 162 and related to the time of selection of the icon 129-136.

The cellular telephone 114 determines in step 1608 whether or not to display the information contained or associated with the exemplary record 202.A in a graphical representation on the display screen 128. The cellular telephone 114 renders information of the record 202.A in a visually presented temporal relationship with information contained within or associated with the plurality of logged event data 204.A-204.N. The cellular telephone 114 alternately displays the graphical representation, such as an exemplary graph 181 of FIG. 18, in step 1610, or proceeds on to step 1612. The cellular telephone 114 determines in step 1612 to return or continue to display the icons 129-136 in step 1602, or to proceed on to step 1614 and cease displaying the icons 129-136 in step 1612 and to continue on to perform alternate computational processes.

Figure 17A:
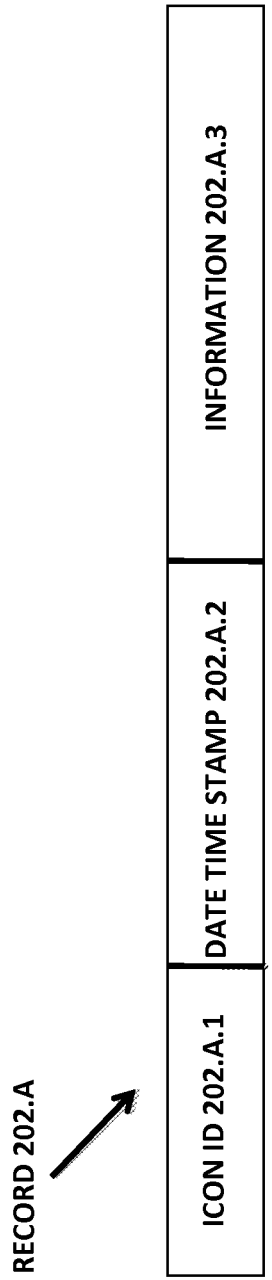
FIG. 17A is an illustration of an exemplary record that includes an icon identifier relating to an icon of FIG. 13.
Figure 17B:
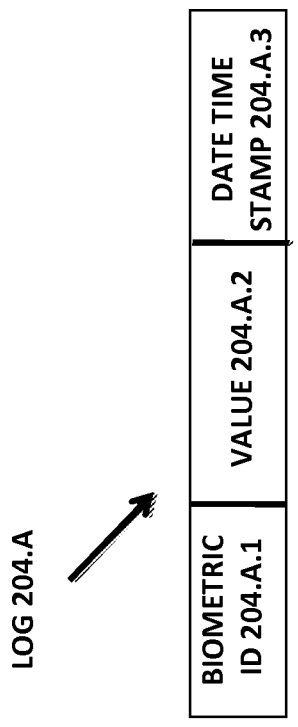
FIG. 17B is an illustration of log event data that contain biometric information generated and transmitted by a biometric sensor of FIG. 12.

Referring now generally to the Figures and particularly to FIGS. 17A and 17B, FIG. 17A is an illustration of the exemplary record 202.A that includes an icon identifier 202.A.1. The date time stamp 202.A.2 is generated by the date time circuit 162. The icon identifier 202.A.1 associates the exemplary record 202.A with an icon 29-36. FIG. 17B is an illustration of the exemplary log event data 204.A that includes a biometric identifier 204.A.1, a measured biometric value 204.A.2 and an event date time stamp 204.A.3 related to the time of recordation of the event biometric value 204.A.2. In certain exemplary methods, the biometric identifier 204.A.1 may associate the exemplary log data 204.A. with a measurement, for example, of a heart rate, a blood pressure, a body temperature, and/or a respiration, wherein the measured biometric value 204.A.2 may be a numeric value of the biometric parameter identified by the biometric identifier 204.A.1 of the exemplary log data 204.A. An optional record information 202.A.3 includes additional information provided by the patient 88 via the input module 140, by uploading from a computer program product 180 and/or by downloading from the network 2. The record information 202.A.3 may include textual information entered from a computer keyboard 184 or mouse 186. According to even other additional or alternate methods, the record information 202.A.3 may optionally be input to the cellular telephone 114 via an audio input module 164 that accepts sound waves and generates digitized recordings therefrom, wherein the digitized recordings may be stored as audio data in the record information 202.A.3. In addition, the audio input and/or a textual interpretation of sound waves received by the audio input module 122 and thereupon stored as text data in the record information 202.A.1.

When the icon identifier 202.A.1 indicates that the identified icon 132-136 specifies an accomplishment, or the record information 202.A.3 indicates that that the comprising exemplary record 202.A identifies an accomplishment, the exemplary record 202.A is defined as an accomplishment record 202.A, and the exemplary record information 202.A.3 is defined as an accomplishment information 202.A.3.

Figure 18:
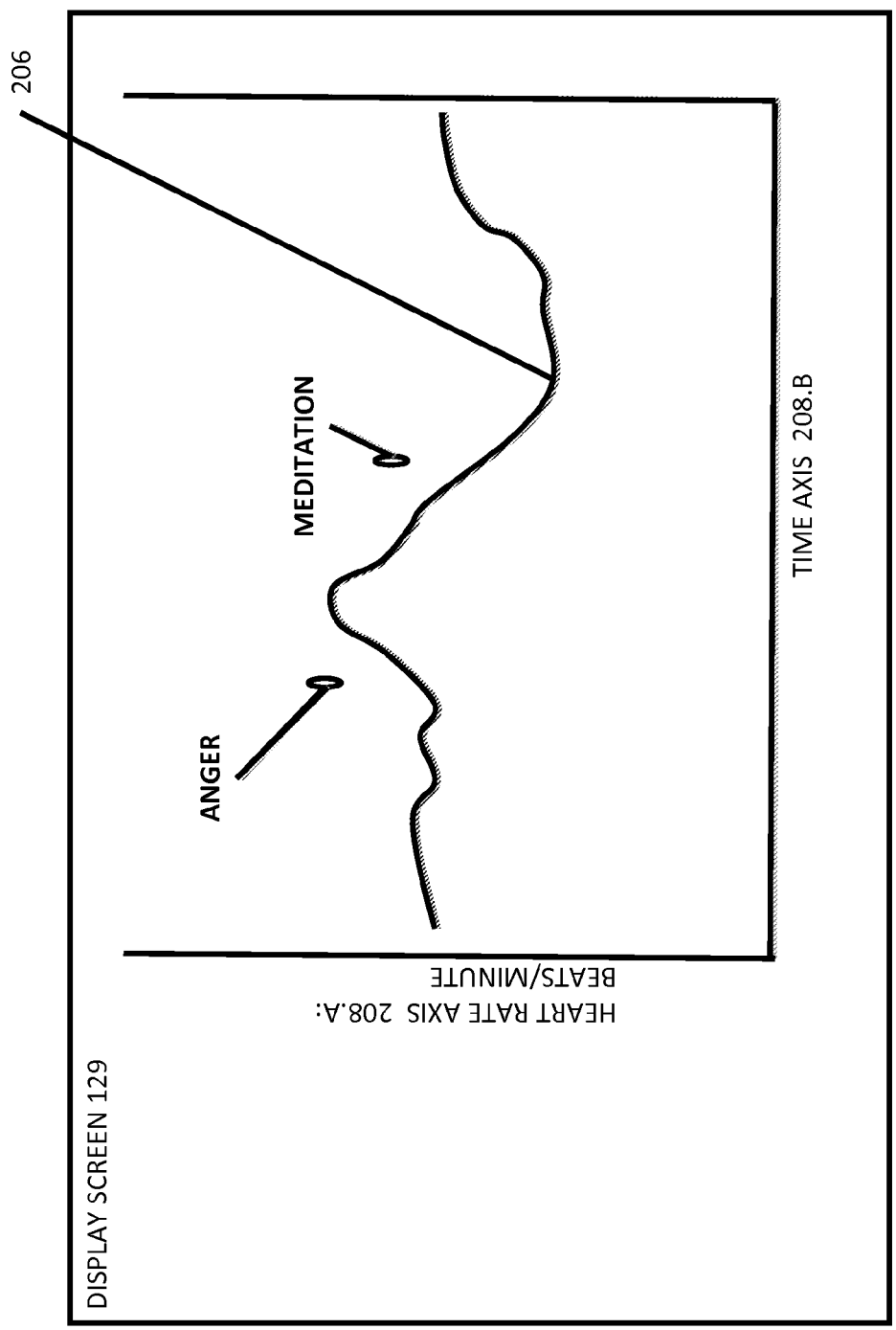
FIG. 18 illustrates a graph 114 wherein a plurality of event log data of FIG. 6A and a plurality of biometric data of FIG. 17B are displayed on a display screen of FIGS. 12, 13 and 14.

Referring now generally to the Figures and particularly to FIG. 18, FIG. 18 illustrates a graph 206 wherein a plurality of event log data 204.A-204.N that each datum includes a beats per minute measurement value as the biometric value 204.A.2-204.N.2. Each biometric value 204.A.2-204.N.2 is plotted within the graph 206 according to its value along a heart rate axis 208.A and the value of the date time stamp 204.A.3-204.N.3 of the same event log data 204.A-204.N along a time axis 208.B. In addition, one or more records 202.A-202.N are plotted as events along the same time axis 208.B, wherein the quality associated with each displayed record 202.A-202-N is presented along the time axis 208.B. The patient 88 may thus review the graph 206 and observe the temporal relationship between each event documented by a record 202.A-202.N and the biometric data measurement values 204.A.2-204.N.2 contained in the plurality of event log data 204.A-204.N.

Figure 19:
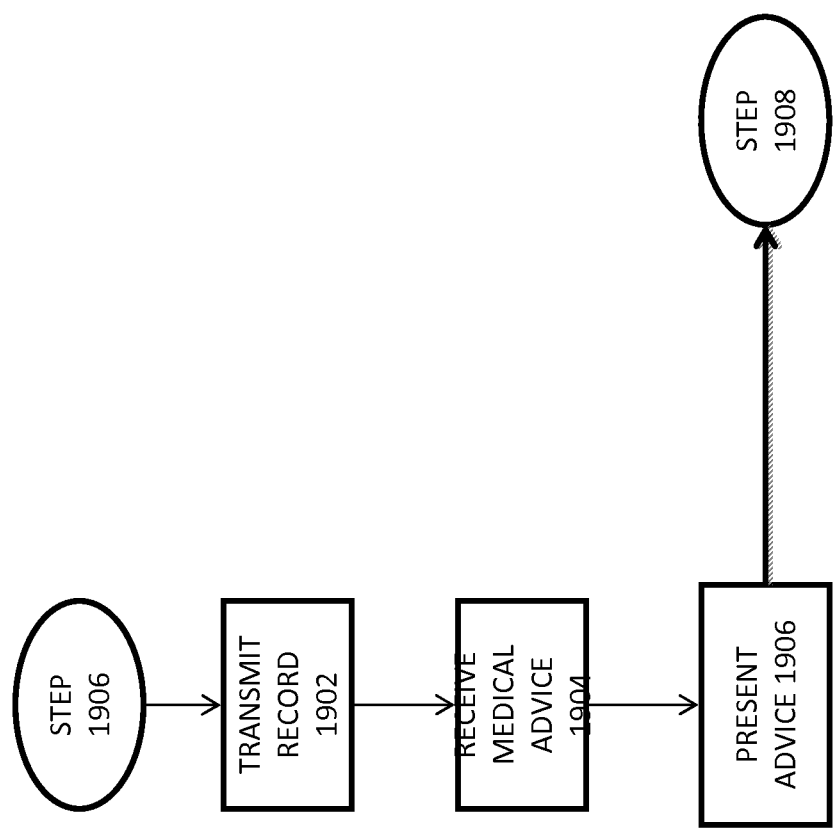
FIG. 19 is an illustration of an additional or alternate method wherein the cellular telephone of FIGS. 12-15 transmits information via the network to the data base system and/or the diagnostic system of FIG. 12.

Referring now generally to the Figures and particularly to FIG. 19, FIG. 19 is an illustration of an additional or alternate method, wherein the cellular telephone 114 transmits in step 1902 the exemplary record 202.A via the network 2 to the data base system 108 and/or the diagnostic system 110. In step 1904 the cellular telephone 114 receives a digitized message that includes a medical advice content via the network 2. The cellular telephone 114 displays the medical guidance content in the display screen 128 in step 1906. In a yet other aspect of the method of the FIG. 19, the medical guidance content is rendered as an audible signal output through the audio output module 152.

Figure 20:
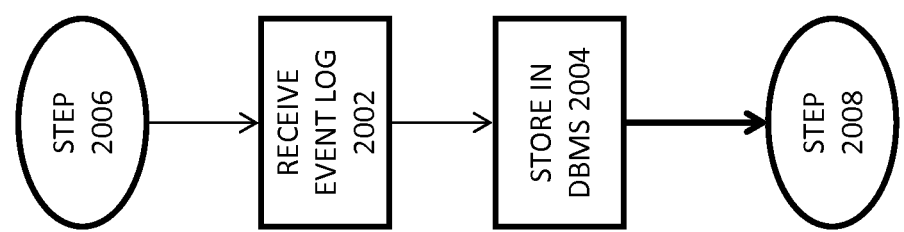
FIG. 20 is an illustration of an additional or alternate method, wherein the cellular telephone of FIGS. 12-15 receives information via the network from the data base system and/or the diagnostic system of FIG. 12.

Referring now generally to the Figures and particularly to FIG. 20, FIG. 20 is an illustration of a still additional or alternate aspect of the method of the of FIG. 20 wherein the cellular telephone 114 receives one or more event logs 204.A-204.N in step 2002 via the network 2. The cellular telephone 114 then stores the one or more event logs 204.A-204.N in the mobile DBMS 200 in step 2004. The one or more event logs 204.A-204.N received in step 2002 will then be included in the next calculation of the graph 206 in the next execution of step 1610. It is understood that the one or more event logs 204.A-204.N received in step 2002 may include biometric measurement values 204.A.2-204.N.2 that are measures, for example, of heart rate, blood pressure, respiration or body temperature.

Figure 21:
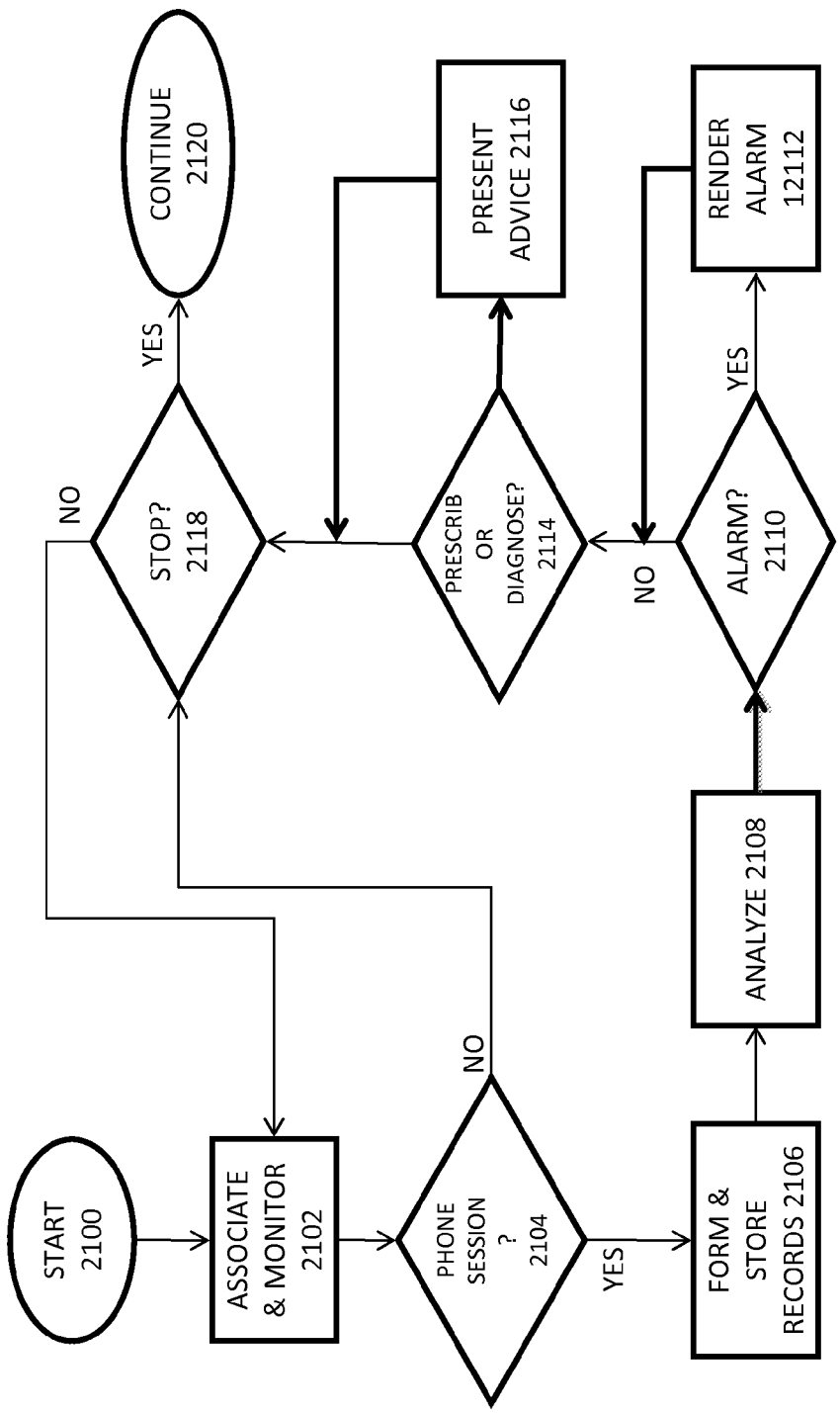
FIG. 21 illustrates a still other additional or alternate method, wherein global positioning data (hereinafter "GPS data") collected from the cellular telephone of FIGS. 12-15 of the patient of FIG. 12 are used to determine the current and relative level of social interaction in which the patient is engaging.

Referring now generally to the Figures and particularly to FIGS. 3 and 21, FIG. 21 illustrates a still other additional or alternate method, wherein GPS data collected from the cellular telephone 114 of the patient 88 are used to determine the current and relative level of social interaction in which the patient 88 is engaging. In step 2102 the cellular telephone 114 is associated with the patient 88. In step 2104 the communications traffic of the cellular telephone 114 is monitored and each phone call is recorded in a session record 210.A-210.N of the patient database 40 of the PMDS 10. The monitoring of the use of the cellular phone 114 may be accomplished by a telecommunications carrier from whom the patient 88 receives a communications enabling service and/or by monitoring by the wireless comms system 120. The session records 210.A-210.N and the patient database are transmitted to, stored in, and made accessible for review to a diagnostician at the diagnostic system 110 and/or the data base computer 108 in step 2106. The diagnostician determines in step 2108 that the level of social interaction indicates an increased risk of degradation in the state of mental health of the patient 88, the diagnostician then determines in step 2110 whether or not to issue an alarm to alert the patient 88 or third parties of a potential decline in mental health. An alarm is transmitted to and rendered in step 2112 by the cellular telephone 114 in optional step 1012. Additionally or alternatively, the diagnostician may in step 2114 generate a therapeutic recommendation, e.g., a diagnosis of, study of, analysis of, determination of or a prescription regarding, one or more health issues of the patient 88 in step 2114, and optionally the medical advice generated in step 2114 is transmitted to and rendered by the cellular telephone 114 in step 2116. It is understood that either or both the alarm transmitted and rendered in step 2112 and the advice transmitted and rendered in step 2116 may optionally, alternatively or additionally be sent to and rendered by the cellular telephone 114, the first network computer 106, the wireless-communications enabled network computer 116 and/or the wireless-communication enabled personal digital assistant 118 in whole or in part.

Referring to FIGS. 14, 15 and 21, it is understood that the cellular telephone 114 may have a plurality of pre-recorded ringtone records 212. The alarm of step 2112 may be rendered by the cellular telephone 114 generating a sound energy as derived from a digitized alarm tone record 214, wherein the sound generated is distinctive to the patient 88 from the sounds generated by the cellular telephone by rendering from one of the ringtones records 212. Alternatively or additionally, the alarm of step 2112 may direct the cellular telephone 114 to energize the vibration module 166 with the aim to attract the attention of the patient 88.

The medical advice transmitted and received by the cellular telephone 114 in step 2116 may be included in whole or in part in an audio message 216 that may be rendered by audible output module 152 for the patient 88 to listen to, and/or by a textual message 218 that the patient 88 may read from the display screen 128.

Additionally or alternatively, the textual message 218, some or all of the therapeutic advice of step 2116, and/or the alarm 2112 may be transmitted to the cellular telephone 114 by means of a text messaging service or a small message service as received and rendered by the SMS module 168 of the cellular telephone 114 and enabled via the TELCO 112 by a telephone services provider, for example, AT&T™ text messaging service or small message service provider.

Figure 22:
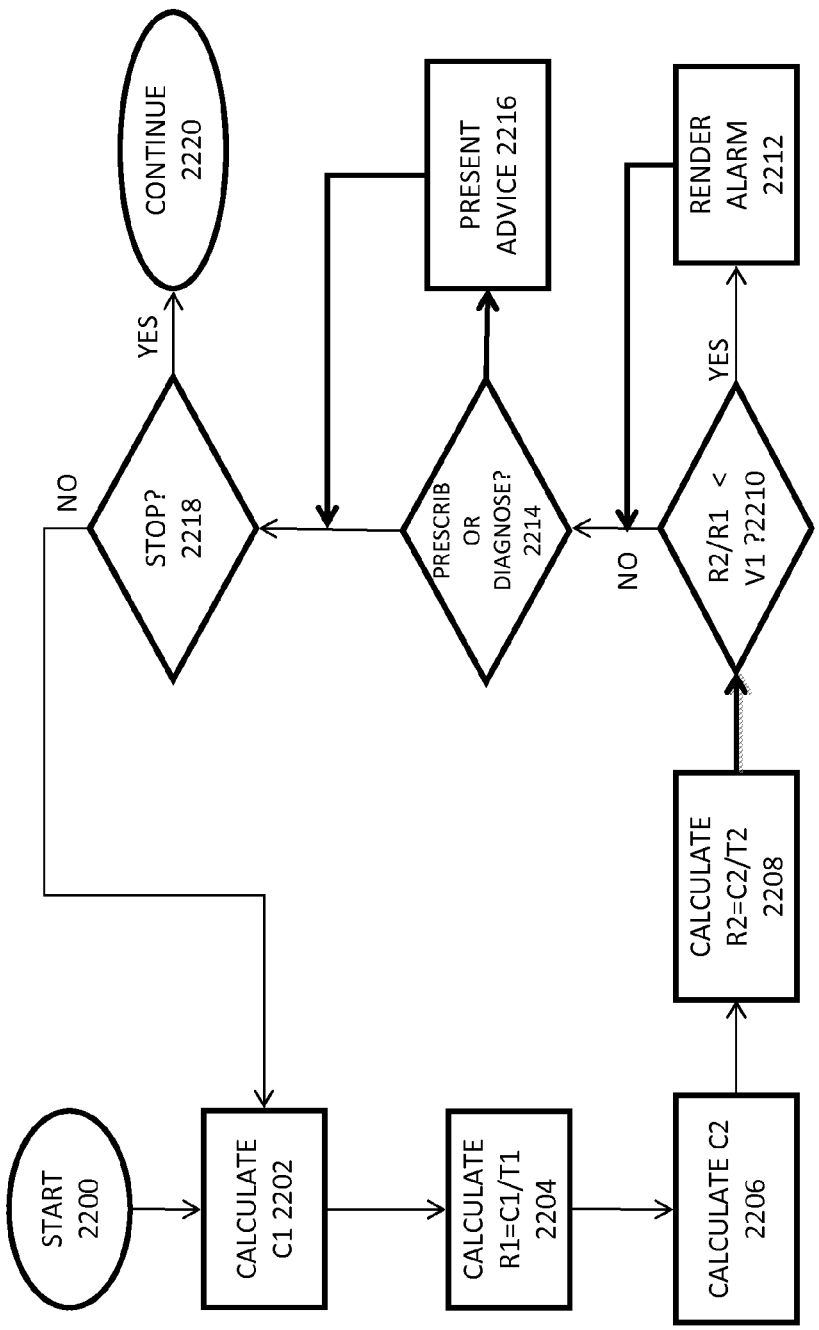
FIG. 22 illustrates yet another additional or alternate method, wherein a diagnostician applies an activity monitor logic of the diagnostic system of FIG. 12.

Referring now generally to the Figures and particularly to the FIGS. 3 and 22, in yet another alternate or additional method, the diagnostician applies in the process of FIG. 22 an activity monitor process of the diagnostic system 110 to generate a communications activity baseline 220 of telephone communications and compares the baseline with a calculation of recent telephone communications to generate a current communications frequency to determine if the current telephone use of the patient 88 is indicative of an increased risk of the patient entering into a declining state of mental health, for example, in certain circumstances, decreased sociability may be an early indicator of declining mental state or other conditions. In step 2202 the diagnostic system 110 counts the number of phone calls C1 placed by the patient 88 over a first length of time T1, for example, over the preceding three months. In step 2204 the diagnostic system 110 calculates a baseline ratio R1 of placed phone calls C1 as divided the first length of time T1. The baseline ratio R1 is thus one instantiation of the communications activity baseline 220.

In step 2206 the diagnostic system 110 determines the number of telephone calls C2 placed by the patient 88 over a shorter and more recent second period of time T2, for example, over the most recent five-day period. In step 2208 the diagnostic system then calculates a current ratio R2 equal to the number of more recently placed phone calls C1 as divided the second length of time T2.

In step 2210 the diagnostic system 110 divides the current ratio R2 by the baseline ratio R1 and determines whether the result of this division is less than a first indicator value V1 of, for example, 0.70. In one exemplary application of the process of FIG. 22, the first indicator value V1 is 0.70, the first ratio R1 indicates the number of telephone calls placed by the patient 88 via the cellular telephone 114 per unit time during the most recent three months, and the second ratio R2 indicates the number of telephone calls placed by the patient 88 via the cellular telephone 114 per unit time during the most recent five day period, whereby if the frequency of phone call placed by the patient 88 dips below 70% of the frequency of telephone calls exhibited by the patient 88 in the most recent three month period, the diagnostic system 110 issues an alert to patient 88 in step 2212 as described above in the process of FIG. 21. It is understood that the alert of step 2212 may be issued by either direction of the diagnostician or by an automatic activity monitor logic 223 of the diagnostic system 110. It is further understood that the activity monitor logic 223 may calculate C1 and/or C2 by calculated number of telephone calls placed from the cellular telephone 114 summed with the number of telephone calls received through the cellular telephone 114. It is further understood that the activity monitor logic 223 may calculate C1 and/or C2 by including the number of attempted telephone calls placed from the cellular telephone 114. It is further understood that the activity monitor logic 223 may calculate C1 and/or C2 by additionally or alternately by counting the number of text messages sent to and/or from the cellular telephone 114.

It is further understood that the diagnostician may provide therapeutic guidance to the patient 88 as an element of the transmitted alarm of step 2212 in steps 2210 through 2216, as per steps 2112 through 2116 of FIG. 21.

Figure 23:
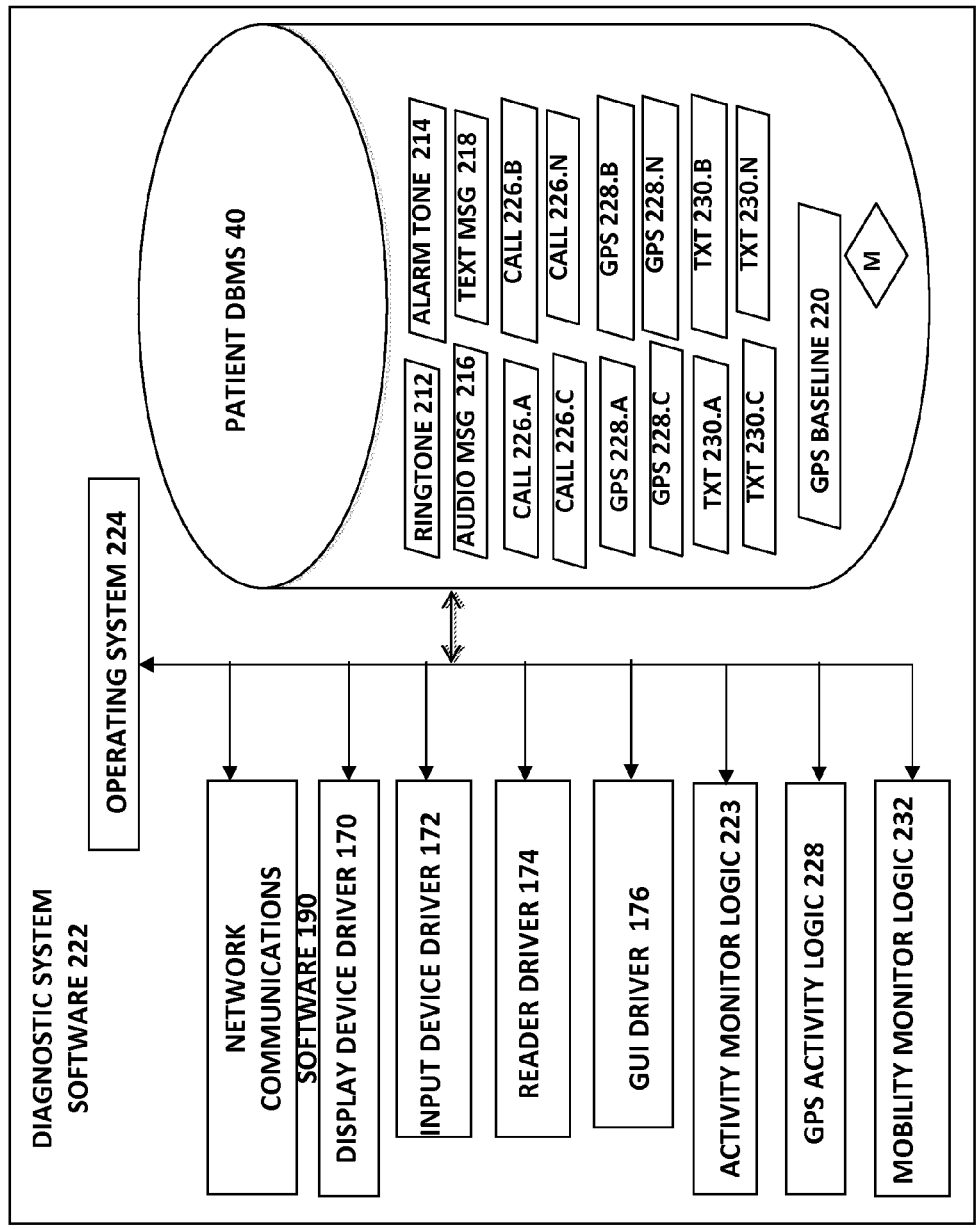
FIG. 23 is a schematic of a diagnostic system software of the diagnostic system of FIG. 12.

Referring now generally to the Figures and particularly to FIG. 23, FIG. 23 is a schematic of a diagnostic system software 222 of the diagnostic system 110. The diagnostic system software 222 includes a diagnostic system operating system 224 and the patient DBMS 40 that stores a plurality digitized software encoded records of one or more ringtones records 212, alarm tone records 214, audio message records 216, and/or text messages 218 that may be transmitted via the network 2 to the cellular telephone 114. The patient DBMS 40 may include a plurality of call records 226.A-226.N, a plurality of GPS records 228.A-228.N, a plurality of text messages records 230.A-230.N and the GPS baseline data 220. The plurality of call records 226.A-226.N, plurality of GPS records 228.A-228.N and plurality of text message records 218 may be provided to the diagnostic system 110 via the network 2 by the TELCO 112 and/or the telecommunications network services provider.

Figure 24A:
FIGS. 24A, 24B and 24C are schematics of information stored in the diagnostic system of FIGS. 12 and 23.
Figure 24B:
Figure 24C:

Referring now generally to the Figures and particularly to FIGS. 24A, 24B and 24C, FIG. 24A is a schematic diagram of an exemplary first phone call record 224.A selected from the plurality of call records 226.A-226.N provided by or the via the TELCO 112 by the telephone services provider. Each phone call record 226.A-226.N contains information related to an individual communication session that is enabled by the network 2. It is understood that a communication session may be enabled by the Internet 2B by voice over Internet Protocol technology and/or by the telephony network 2B. The information contained within the plurality of phone call records 226.A-226.N may be provided by or via the TELCO 112 by the telephone services provider in whole or in part.

The exemplary first call record 226.A relates to a first communications session, for example, an "instant communications session". A phone identifier 226.A.1 identifies the cellular telephone 114. The phone identifier 226.A.1 may be, for example, a telephone number or a network address, or may be another telephone (not shown) or a network address of a computer 106, 116. A second phone identifier 226.A.2 identifies a second telephone (not shown) or a computer 106 or 116. It is understood that the second phone identifier 226.A.2 may be a telephone number or a network address, or may be a reference number to the second telephone or a computer 106 or 116 that is issued to protect the privacy of another party. An origin flag 226.A.3 indicates whether the instant communications session was initiated by the means of either (a.) the cellular telephone 114, or (b.) the computer 106 or other computer 116. A call start data 226.A.4 identifies the start time of the instant communications session. A call duration data 226.A.5 documents the length of time of the instant communications session. A GPS data 226.A.6 includes a global position system data that indicates the location of the cellular telephone 114 at the start time of the instant communications session or at a moment during the duration of the instant communications session. The GPS data 226.A.6 may be generated by the GPS module 156 of the cellular telephone 114 in concert with information received from a global positioning system.

Referring now generally to the Figures and particularly to FIG. 24B, FIG. 24B is a schematic diagram of an exemplary first GPS record 228.A. A phone identifier 228.A.1 identifies the cellular telephone 114. A GPS sampling data 228.A.2 includes a global position system data that indicates the location of the cellular telephone 114. A GPS time data 228.A.3 indicates a time and date that the GPS sampling data 228.A.2 was acquired by the cellular telephone 114.

Referring now generally to the Figures and particularly to FIG. 24C, FIG. 24C is a schematic diagram of an exemplary first text message record 228.A selected from the plurality of text session records 230.A-230.N. Each text record 230.A-230.N contains information related to an individual texting session that is enabled by the network 2. It is understood that a communications session may be enabled by the Internet 2B by various technologies, for example, Voice Over Internet Protocol (VoIP) technology, the telephony network 2A, etc. The information contained within the plurality of text records 230.A-230.N may be provided by or via the TELCO 112 by the telephone services provider in whole or in part.

The exemplary text session record 230.A relates to a first text session, i.e., an "instant text session". A phone identifier 230.A.1 identifies the cellular telephone 114. A second phone identifier 230.A.2 identifies a second telephone (not shown) or a computer 106 or 116 that participated in the instant text message. A text time data 230.A.3 identifies a time of initiation or completion of the instant text message session. An origin flag 230.A.4 indicates whether the instant communications session was initiated by the means of either, for example, (a.) the cellular telephone 114, or (b.) the computer 106 or other computer 116.

Figure 25:
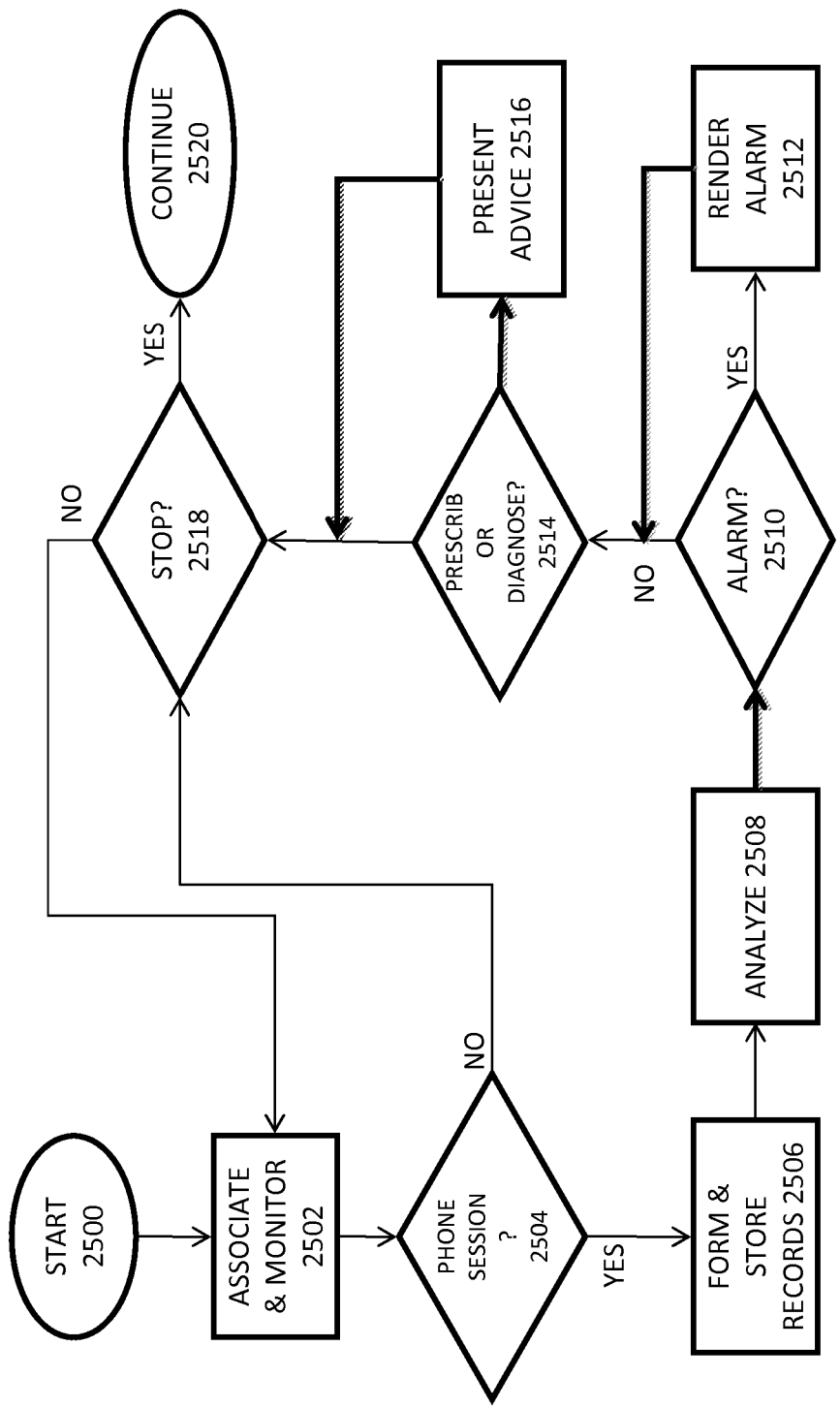
FIG. 25 illustrates a still other additional or alternate method, wherein GPS data collected from the cellular telephone of FIGS. 12-15 of the patient of FIG. 12 are used to determine the current and relative level of social interaction in which the patient is engaging.

Referring now generally to the Figures and particularly to FIG. 25, FIG. 25 illustrates a still other additional or alternate method, wherein GPS data collected from the cellular telephone 114 of the patient 88 is used to determine the current and relative level of social interaction in which the patient 88 is engaging. In step 2502 the cellular telephone 114 is associated with the patient 88 and monitored. The GPS module 156 of the cellular telephone 114 is periodically sampled and each sampled GPS datum is recorded in an individual GPS record 228.A-228.N of the patient DBMS 40. The monitoring of the use of the cellular phone 114 may be provided by or via the TELCO 112 by the telephone services provider in whole or in part, for example, in step 2504 during a phone session, from which the patient 88 receives a text enabling service and/or by monitoring by the wireless comms system 120, etc. The GPS records 228.A-228.N and the patient database 40 are transmitted to, stored in, and made accessible for review to a diagnostician at the diagnostic system 110 and/or the data base computer 108. The diagnostician determines in step 2508 that the level of social interaction indicates an increased risk of degradation in the state of mental health of the patient 88, the diagnostician then determines in step 2510 whether or not to issue an alarm to alert the patient 88 or third parties of a potential decline in mental health. An alarm is transmitted to and rendered in step 2512 by the cellular telephone 114 in optional step 2512. Additionally or alternatively, the diagnostician may in step 2514 generate a therapeutic recommendation, for example, a diagnosis of, or a prescription regarding, one or more health issues of the patient 88 in step 2514, and optionally the medical advice generated in step 2516 is transmitted to and rendered by the cellular telephone 114. It is understood that either or both the alarm transmitted and rendered in step 2512 and the advice transmitted and rendered in step 2516 may optionally, alternatively or additionally be sent to and rendered by the cellular telephone 114, the first network computer 106, the wireless-communications enabled network computer 116 and/or the wireless-communication enabled personal digital assistant 118 in whole or in part.

It is understood that the cellular telephone 114 may have a plurality of pre-recorded standard ringtones records 212. The alarm of step 2112 may be rendered by the cellular telephone 114 generating a sound energy as derived from an alarm tone record 212, wherein the sound generated is distinctive to the patient 88 from the sounds generated by the cellular telephone 114 by rendering from one of the ringtones records 214. Alternatively or additionally, the alarm of step 2512 may direct the cellular telephone 114 to energize the vibration module 166 with the aim to attract the attention of the patient 88.

The medical advice transmitted and received by the cellular telephone 114 in step 2516 may be included in whole or in part in an audio message record 216 that may be rendered by audible output module 152 for the patient 88 to listen to, and/or by a textual message record 230 that the patient 88 may read from the display screen 128.

Additionally or alternatively, the textual message 230, some or all of the therapeutic advice of step 2116, and/or the alarm 2112 may be transmitted to the cellular telephone 114 by means of a text messaging service or a small message service as received and rendered by an SMS module 168 of the cellular telephone 114 and may be provided in whole or in part by or via the TELCO 112 by the telephone services provider.

Figure 26:
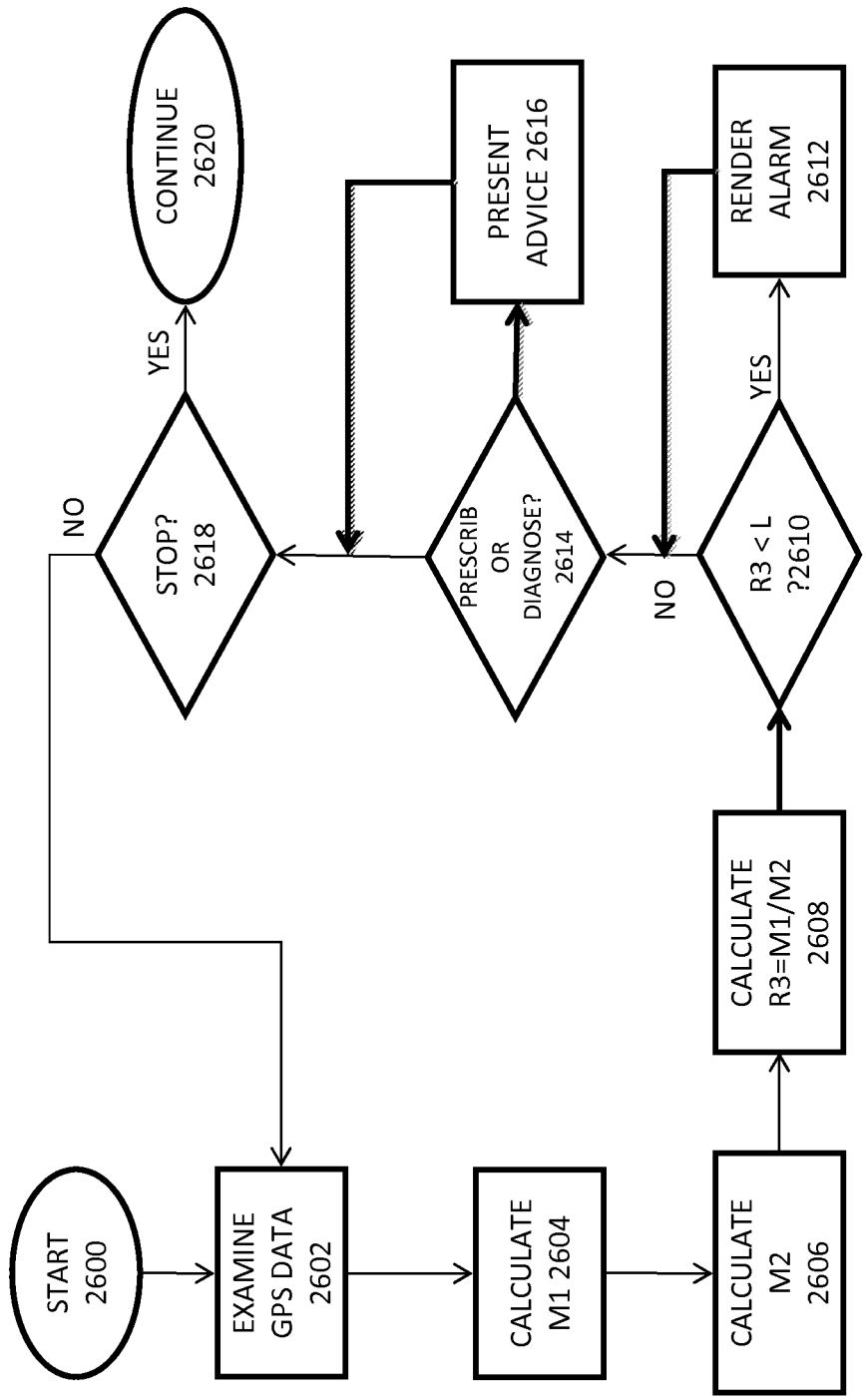
FIG. 26 is an illustration of yet another additional or alternate method, wherein a diagnostician applies a mobility monitor logic of the diagnostic system of FIGS. 12 and 23 to generate a GPS data baseline (hereinafter "GPS baseline").

Referring now generally to the Figures and particularly to the FIG. 26, in yet another additional or alternate method, the diagnostician applies a mobility monitor logic 232 of the diagnostic system 110 to generate the GPS baseline 220 derived from the telephone GPS information of the plurality of GPS records 226.A-226.N and compares the GPS baseline 220 with a more recent plurality of GPS readings to determine if the mobility of the patient 88 is indicative of an increased risk of the patient entering into a reduced state of mental health. In step 2602 the diagnostic system 110 examines the GPS records 228.A-228.N containing GPS information collected over an extended length of time T3, for example, over the preceding three months. In step 2604 the diagnostic system 110 calculates the GPS mobility baseline 220 indicative of the movement presented by the patient 88 during the extended time C3, for example, an extended mobility value M1.

In one alternate aspect of the method of FIG. 26, the mobility baseline 220 is automatically calculated by (a.) selecting a plurality of GPS records 228.A-228.N; (b.) ordering the GPS records 228.A-228.N in order of the GPS time data 228.A.3-228.N.3; (c.) calculating the distance between each ordered GPS records 228.A-228.N by straight line measurements between succeeding each ordered GPS location data 228.A.2-228.N.2; (d.) summing the distances measured in the previous step; and dividing the distance measurement by a length time measured between the earliest GPS time data 228.A.3-228.N.3 and the most recent GPS time data 228.A.3-228.N.3 of the selected plurality of GPS records 228.A-228.N.

In step 2604 the diagnostic system 110 examines the GPS records 228.A-228.N containing GPS information collected over a shorter and recent mobility period of time T4, for example, over the most recent five day period, and calculates a recent mobility value M1 in step 2604. In step 2606 the diagnostic system 110 examines the GPS records 228.A-228.N containing GPS information collected over a greater period of time and calculates an extended time period mobility value M2

In step 2608 the diagnostic system 110 calculates a current mobility ratio R3 equal to the recent mobility value M1 divided by the extended mobility value M2.

In step 2610 the diagnostic system 110 compares the current mobility ratio R3 to a level L. In one exemplary application of the measurement of the patient's recent mobility dips below 70% the patient's estimated mobility as expressed by the mobility baseline 220, the diagnostic system 110 issues an alert to patient 88 in step 2612 as described above in the process of FIG. 25. It is understood that the alert of step 2612 may be issued by either direction of the diagnostician or by the mobility monitor logic 232. It is further understood that the diagnostician may provide therapeutic guidance to the patient 88 as an element of the transmitted alarm of step 2612 in steps 2620 through 2216, and as per steps 2512 through 2520 of FIG. 25.

Figure 27:
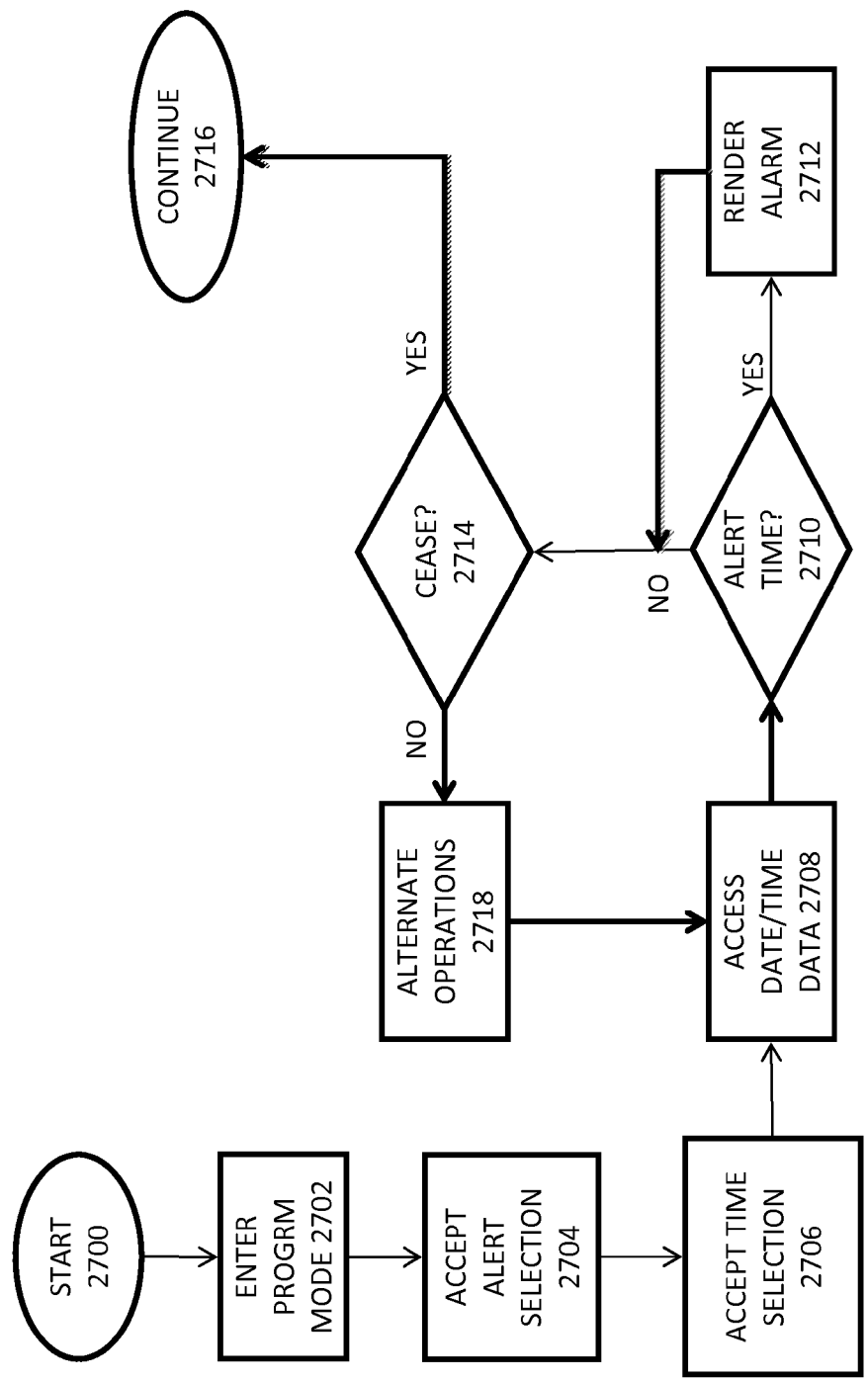
FIG. 27 is a process chart of an even other additional or alternate method, wherein the cellular telephone of FIGS. 12-15 is programmed to render a distinctive ringtone, alarm tone, audio message, and/or text message to alert the patient of FIG. 1 to take a medication, engage in a medically recommended behavior, or cease a behavior.

Referring now generally to the Figures and particularly to FIG. 27, FIG. 27 is a process chart of an even other additional or alternate method, wherein the cellular telephone 114 is programmed to render a distinctive ringtone record 212, alarm tone record 214, audio message record 216, and/or text message record 218 to alert the patient 88 to take a medication, engage in a medically recommended behavior, or cease a behavior. In step 2702 the cellular telephone 114 determines if a programmer, for example, the patient 88, the diagnostician, a health care provider, or other party, has input a command to place the cellular phone 114 into an alert programming mode. When the cellular telephone 114 determines in step 2702 that the programmer has input a programming command, the cellular telephone 114 proceeds to step 2704 and accepts a selection of an alert selection from the programmer, where the alert selection may be indicated from a group including for example, but not limited to, a distinctive ringtone record 212, alarm tone record 214, audio message record 216, and/or text message record 218. In step 2706 the cellular telephone 114 accepts an alert time from the programmer which indicates at which time the cellular telephone 114 is to render the selected alert. The cellular telephone 114 proceeds from step 2706 to step 2708 to access the date/time circuit 162 and in step 1610 to determine whether the alert time has passed. When the cellular telephone 114 determines in step 2710 that the alert time has occurred, the cellular telephone 114 proceeds on to step 712 and renders the selected alarm, wherein such rendering may include an excitation of, for example, the vibration module 166, a sound generated from ringtone record 212, alarm tone record 214, and/or audio message record 216 by means of the audio output module 152, and/or text message record 218 by means of the display device 156. The cellular telephone 114 proceeds from either step 2710 or step 2712 to determine whether to cease the alert cycle in step 2714. When the cellular telephone 114 determines in step 2714 to cease the alert cycle of steps 2708 and 2710, the cellular telephone 114 proceeds on to step 2716 and performs additional or alternate computational operations, which may include a return to step 2702 at a later time. When the cellular telephone 114 determines in step 2714 to continue to execute the alert cycle of steps 2708 through 2714, the cellular telephone 114 proceeds on to step 2718 and performs additional or alternate computational operations before performing another comparison of the programmed alert time of step 2710 with the real time as indicated by a current output of the date/time circuit 162 of step 2708.

It is understood that the alert rendered in step 2710 may encourage the patient to inhale a second medication 240 or to apply a topical medication 242 to a skin area 244 of the patient 88.

Figure 28:
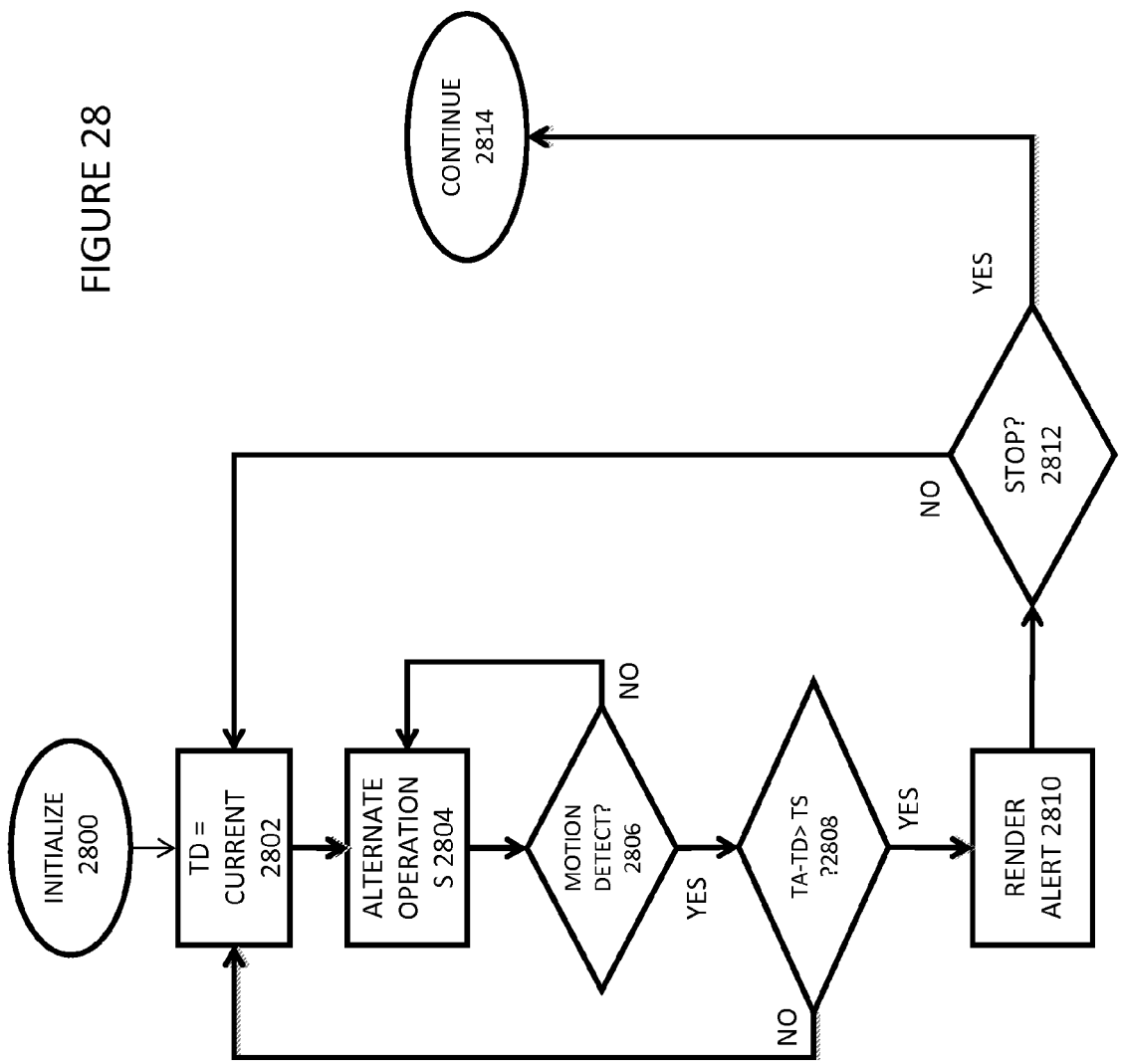
FIG. 28 illustrates a still further additional or alternate method, wherein the phone of FIGS. 12-15 is programmed to remind the patient of FIG. 12 to take, e.g., ingest, inhale, insert, or topically apply, one or more medications of FIG. 12.

Referring now generally to the Figures and particularly to FIG. 28, FIG. 28 illustrates a still further alternate additional or alternate method, wherein the cellular phone 114 is programmed to remind the patient 88 to take, for example, ingest, inhale, insert or topically apply, etc., one or more medications 126. The phone 114 initializes a resting time variable TD to a current date and time reading received from the date/time circuit 162 in step 2802. The phone 114 then proceeds to step 2804 to perform alternate computational operations, and periodically returns to step 2806 to determine whether to query the accelerometer 170 to determine whether the accelerometer 170 has detected motion since the most recent execution of step 2802. When the phone 114 determines in step 2806 that the accelerometer 170 indicates motion of the phone 114 since the most recent execution of step 2802, the phone 114 proceeds on to step 2808 to determine whether the time elapsed between the current value of the resting time variable TD and a newer and actual date and time reading TA received from the date/time circuit 162 is greater than a sleep time value TS, for example, wherein the sleep time value is a value preferably between the time durations of four hours and eight hours. When the phone 114 determines in step 2808 that the accelerometer 170 has not detected motion for a period of time greater than the sleep time value TS, the phone 114 proceeds on to step 2810 and to render an alert to encourage the patient 88 to take one or more medications, e.g., medicine 126, 240 and 242.

It is understood that the motion detector 23 of FIG. 1 may be, include, or be comprised within, an accelerometer 170, a GPS module 156, or a cellular telephone 114.

When the cellular telephone 114 determines in step 2808 that the alert time has occurred, the cellular telephone 114 proceeds on to step 2810 and renders the selected alarm, wherein such rendering may include, for example, an excitation of the vibration module 166, a sound generated from ringtone record 212, alarm tone record 214, and/or audio message record 216 by means of the audio output module 152, and/or text message record 218 by means of the display device 156.

The cellular telephone 114 proceeds from either step 2810 or step 2812 to determine whether to cease the alert cycle of steps 2800 through 2812. When the cellular telephone 114 determines in step 2812 to cease the alert cycle of steps 2800 through 2812, the cellular telephone 114 proceeds on to step 2814 and performs additional or alternate computational operations, which may include a return to step 2802 at a later time.

Figure 29:
FIG. 29 is a schematic of a first exemplary patient record selected from a plurality of patient records that are stored in the cellular telephone of FIGS. 12-15, the DB computer of FIG. 12, and/or the diagnostic system of FIGS. 12 and 23.

Referring now generally to the Figures and particularly FIG. 29, FIG. 29 is a schematic of a first exemplary patient record 232.A selected from a plurality of patient records 232.A.1-232.A.N that are stored in the patient DBMS 40 and/or the mobile DBMS 200 as stored in the cellular telephone 114, the DB computer 108, and/or the diagnostic system 110. The first exemplary patient record 232.A includes a patient identifier 232.A.1, a phone identifier 232.A.2, a biometric data field 232.A.3, an ingestion record 232.A.4, a patient reminder instructions data field 232.A.5, and a behavior data field 232.A.6. The patient identifier 232.A.1 uniquely identifies the patient 88 to the DBMS 178 and 206. The phone identifier 232.A.2 uniquely identifies the phone 114 to the DBMS 178 and 206. The biometric data field 232.A.3 includes biometric data received from the sensors 20-23 and 98-104 with associated time date stamps generated by the time/date circuit 162 wherein each date time stamp individually identifies the time of generation of an associated biometric datum. The ingestion record 232.A.4 includes data identifying medicines taken, for example, inhaled, applied, inserted, ingested, etc., with associated time date stamps generated by the time/date circuit 162 wherein each date time stamp individually identifies the time of generation of a comprising ingestion record. The patient reminder instructions data field 232.A.5 includes instructions directing the phone 114 to when and how to render an alert to encourage the patient 88 to perform a specified meditative practice, a relaxation practice, and/or a therapeutic behavior. The behavior data field 232.A.6 includes data noting a performance of a meditative practice, a relaxation practice, a therapeutic behavior, and/or other practice or behavior of the patient 88, with associated time date stamps generated by the time/date circuit 162 wherein each date time stamp individually identifies the time of the referenced performance or behavior.

Figure 30:
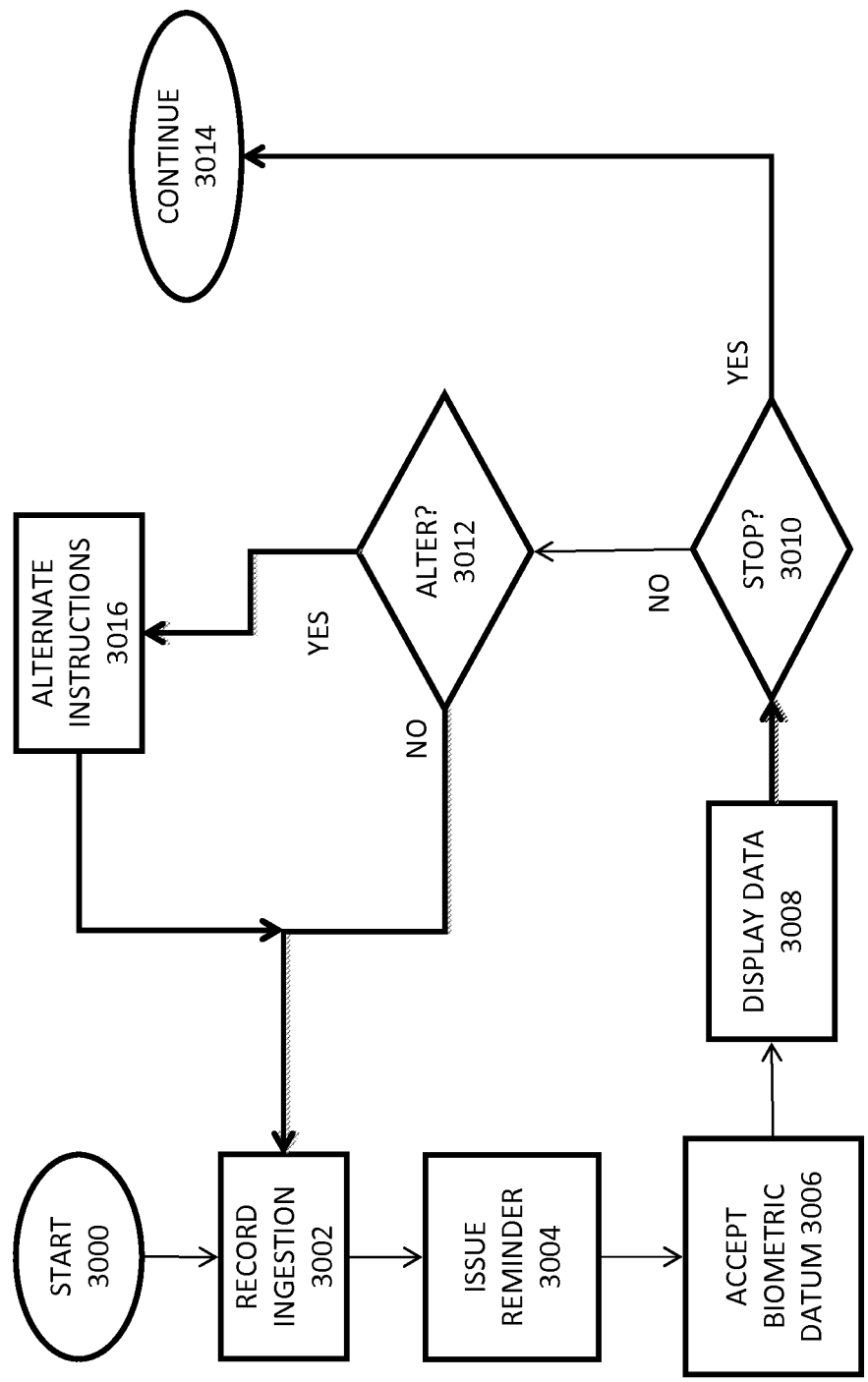
FIG. 30 illustrates an even other additional or alternate method, wherein a patient record is applied by the phone of FIGS. 12-15 to record biometric data received from one or more sensors of FIG. 1 and to send reminding alerts to encourage the patient of FIG. 1 to perform meditative exercises, relaxation exercises, or other therapeutic or prescribed behaviors.

Referring now generally to the Figures and particularly to FIG. 30, FIG. 30 illustrates an even additional or alternate method, wherein a patient record 232.A-232.N is applied by the phone 114 to record biometric data received from one or more sensors 20-23 and 98-104 and to send alerts to encourage the patient 88 to perform meditative exercises, relaxation exercises, or other therapeutic behaviors. In step 3002 the phone 114 receives notice of a taking of a medication, e.g., medicine 126, 240 or 242, and records the medicine application datum with an associated time date stamp in the ingestion records data field 232.A.4 of the exemplary first patient record 232.A. In step 3004 the phone 114 issues an alert to the patient in accordance with information stored in the reminder message instructions 232.A.5. In step 3006 the phone 114 receives a biometric datum received from one or more sensors 20-23 and 98-104, and records the received biometric datum with an associated time date stamp in the biometric data field 232.A.3. It is understood that the biometric datum might be (a.) a measure of blood pressure or hypertension generated by and received from the blood pressure sensor 90; (b.) a measure of heart rate generated by and received from the heart rate sensor 94; (c.) a measure of body temperature generated by and received from the temperature sensor 98; and/or (d.) a measure of respiration generated by and received from the respiration sensor 102.

In step 3008, the data stored in the exemplary first patient data record 232.A is visually presented to the patient 88 via the display screen 128 by the GUI driver 198 and optionally as described in reference to FIG. 18. This presentation of step 3008 is executed with the intent to provide feedback to the patient 88 of the effect that the behavior of the patient 88 is having on the physiological state of the patient 88, whereby the patient 88 is encouraged to follow the practices. e.g., making a pause, avoiding a situation, taking a pill, etc., to achieve a prescribed behavior, e.g., cool, calm, composed, etc., and behavior specified by the reminder message instructions 232.A.5.

The phone 114 determines in step 3010 whether to continue performing the cycle of steps 3000 through 3008, or to proceed on to alternate computational processes of step 3014. When the phone 114 determines in step 3010 to continue performing the cycle of steps 3000 through 3008, the phone proceeds on to step 3012 and to determine whether instructions to the patient 88 of a dosage of a medicine 126, 240 and 242, a schedule of taking a medicine 126, 240 and 242, or a recommended patient practice or behavior. When a therapeutic alteration is determined in step 3012, the phone 114 proceeds on to step 3016 and to alter information stored in the reminder message instructions 232.A.5. The phone 114 then proceeds from step 3016 on to step 3002.

It is understood that the biometric datum received in one or more executions of step 3006 may be received by (a.) wireless transmissions from the wireless comms system 120, and/or a wireless enabled sensor 20-23, 90, 94, 98 and 102; and/or (b.) a hardwired connection with the network 2. It is further understood that a notice of an ingestion of the composition device 122 may be received by the phone 114 as transmitted wirelessly from the IEMD 4 and/or the wireless comms system 120.

It is additionally understood that the alteration of information stored in the reminder message instructions 232.A.5 as performed in step 3016 may be directed and provided by a health care professional as input from the DB computer 108 and/or the diagnostic system 110.

Figure 31:
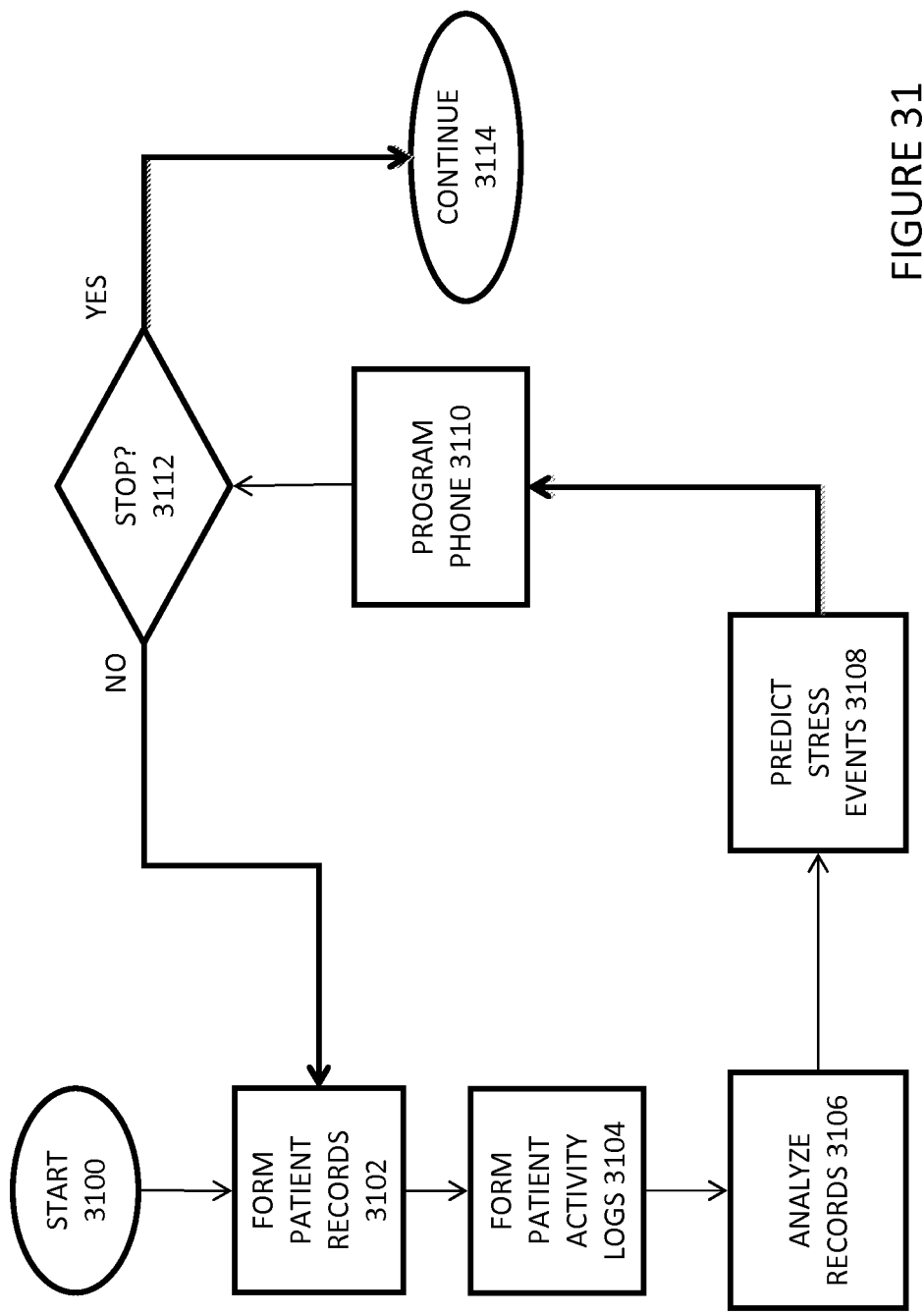
FIG. 31 describes another additional or alternate method, wherein high stress events that occur routinely in the routine life of the patient are identified and the phone of FIGS. 12-15 is programmed to encourage the patient of FIG. 12 to take therapeutic steps to reduce the harmful impact of the stress inducing events.
Figure 33:
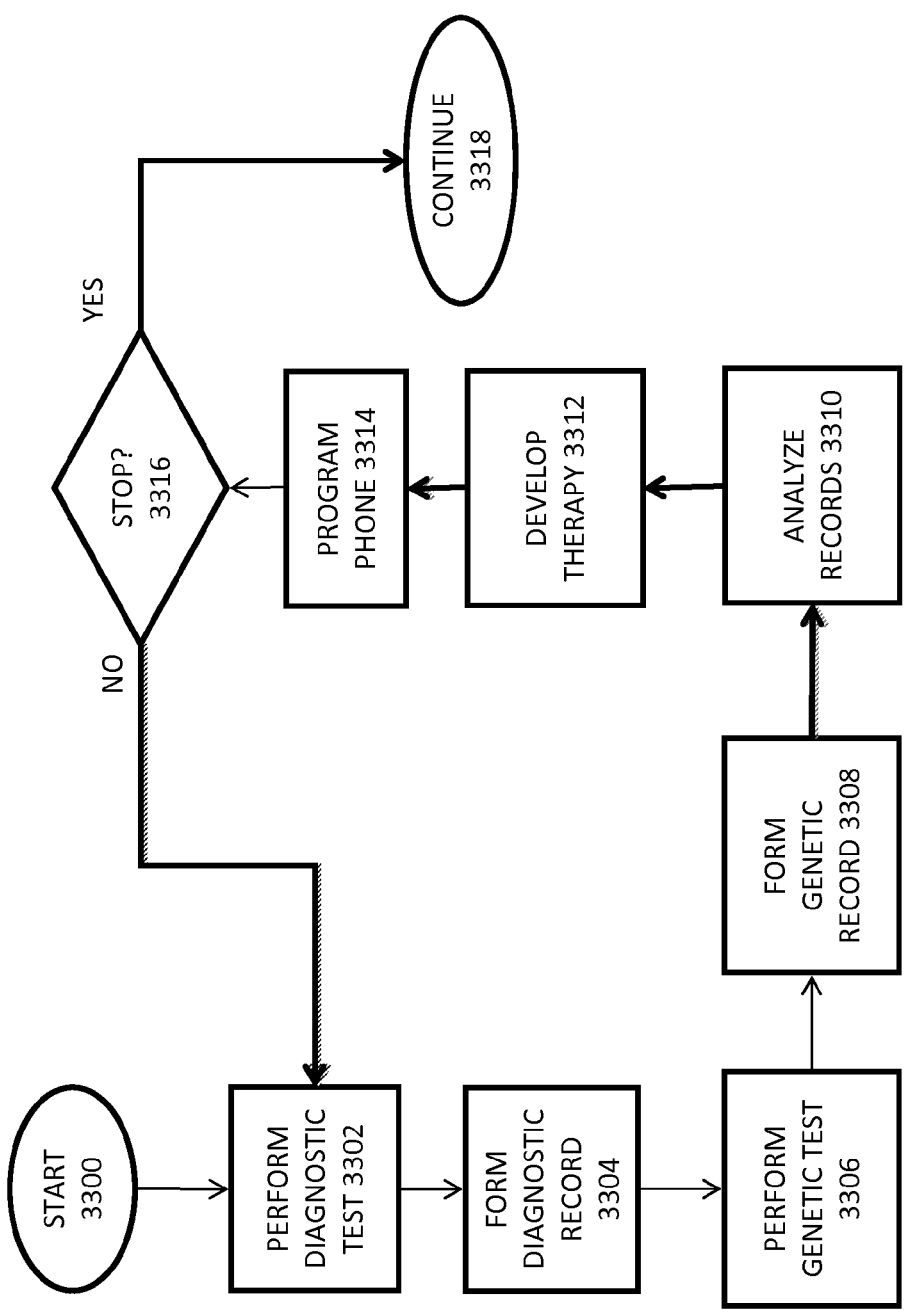
FIG. 33 describes a yet other alternate or additional method, wherein the diagnostician analyzes information about diagnostic test results, genetic test results, patient records, patient activity logs, and other information to develop and prescribe therapy.

Referring now generally to the Figures and particularly to FIG. 31, FIG. 31 describes another additional or alternate method, wherein high stress events that occur routinely in the life of the patient are identified and the phone 114 is programmed to encourage the patient 88 to follow or perform therapeutic or prescribed steps or instructions to reduce the harmful impact of the stress inducing events. In step 3102 a plurality of patient records 232.A-232.N are formed by observing and storing the readings of the sensors 20-23, 90, 94, 98 and 102. In step 3104 patient activity logs 168 are formed and populated with data, wherein the patient 88 records time and dates and descriptions of daily events experienced by the patient 88. The patient activity logs 168 may be populated from inputs by the patient 88 to the phone 114, the PDA 118, and/or the wireless computer 116. The diagnostician or other health care professional analyzes the plurality of patient logs 232A-232N in comparison with the patient records 232.A-232.N to isolate and find patterns between sensory indications of physiological stress experienced by the patient 88 and predictable events in the life of the patient, e.g., meetings with supervisors, subordinates, or family members. The diagnostician or health care professional then determines those events that can be anticipated and lead to high stress conditions for the patient 88 in step 3108. The diagnostician then programs the phone 114 to issue a message to the patient prior to one or more anticipated stress-inducing event. The diagnostician or health care professional programs the phone 114 in step 3110 via the diagnostic system 110 and the network 2. The diagnostician or health care professional determines in step 3112 whether to continue the loop of steps 3102 to 3112 or to proceed on to alternate processes of step 3114.

FIG. 29 is a schematic of an exemplary patient activity log 232A that includes the patient ID 232.A.1, the phone ID 232.A.2, and a plurality of activity notes 232A.1-232A.N. Each activity note 232A.1-232A.N contains a notation by the patient 88 of the date, time and nature of an activity experienced by the patient 88, e.g., arrival at work, commuting experiences, physical exercise, social interactions, and work related behavior.

Referring now generally to the Figures and particularly to FIG. 32, FIG. 32 describes a yet additional or alternate method, wherein the diagnostician analyzes information about diagnostic test results, genetic test results, patient records 232.A-232.N, patient activity logs 232A-232N, and other information to develop and prescribe therapy. One or more diagnostic tests are performed in step 3202. The results of these diagnostic tests are stored in the diagnostic system 110 in step 3204 in one or more diagnostic test records 236.A-236.N. One or more genetic tests are performed in step 3206. The results of these genetic tests are stored in the diagnostic system 110 in step 3208 in one or more genetic test records 252.A-252.N. The diagnostician then analyzes the diagnostic test records 236.A-236.N, the genetic test records 252.A-252.N, the patient records 232.A-232.N, the patient activity logs 232A-232N, and other information in step 3210 by means of the diagnostic system 110. The diagnostician then updates a therapeutic plan in step 3212, and programs the cell 114 to transmit alerts and alarms to the patient 88 in step 3314 that are designed to encourage the patient 88 to comply with the prescribed therapy of step 3312.

The diagnostician or health care professional determines in step 3316 whether to continue the loop of steps 3302 to 3316 or to proceed on to alternate processes of step 3318.

Figure 34:
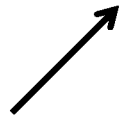
FIG. 34 is a schematic of an exemplary first diagnostic test record that includes a patient identifier, a phone identifier, and a plurality of diagnostic test notes.

FIG. 34 is a schematic of an exemplary first diagnostic test record 236.A that includes the patient ID 232.A.1, the phone ID 232.A.2, and a plurality of diagnostic test notes 236.A.1-236.A.N. Each diagnostic test note 236.A.1-236.A.N contains information identifying a diagnostic test, a time and date of the diagnostic test, and the results of the diagnostic test.

Figure 35:
FIG. 35 is a schematic of an exemplary first genetic test record that includes the patient identifier of FIG. 34, the phone identifier, and a plurality of genetic test notes.

FIG. 35 is a schematic of an exemplary first genetic test record 238.A that includes the patient ID 232.A.1, the phone ID 232.A.2, and a plurality of genetic test notes 238.A.1-238.A.N. Each genetic test note 238.A.1-238.N contains information identifying a genetic test, a time and date of a performance of the genetic test, and the results of the genetic test.

Figure 36:
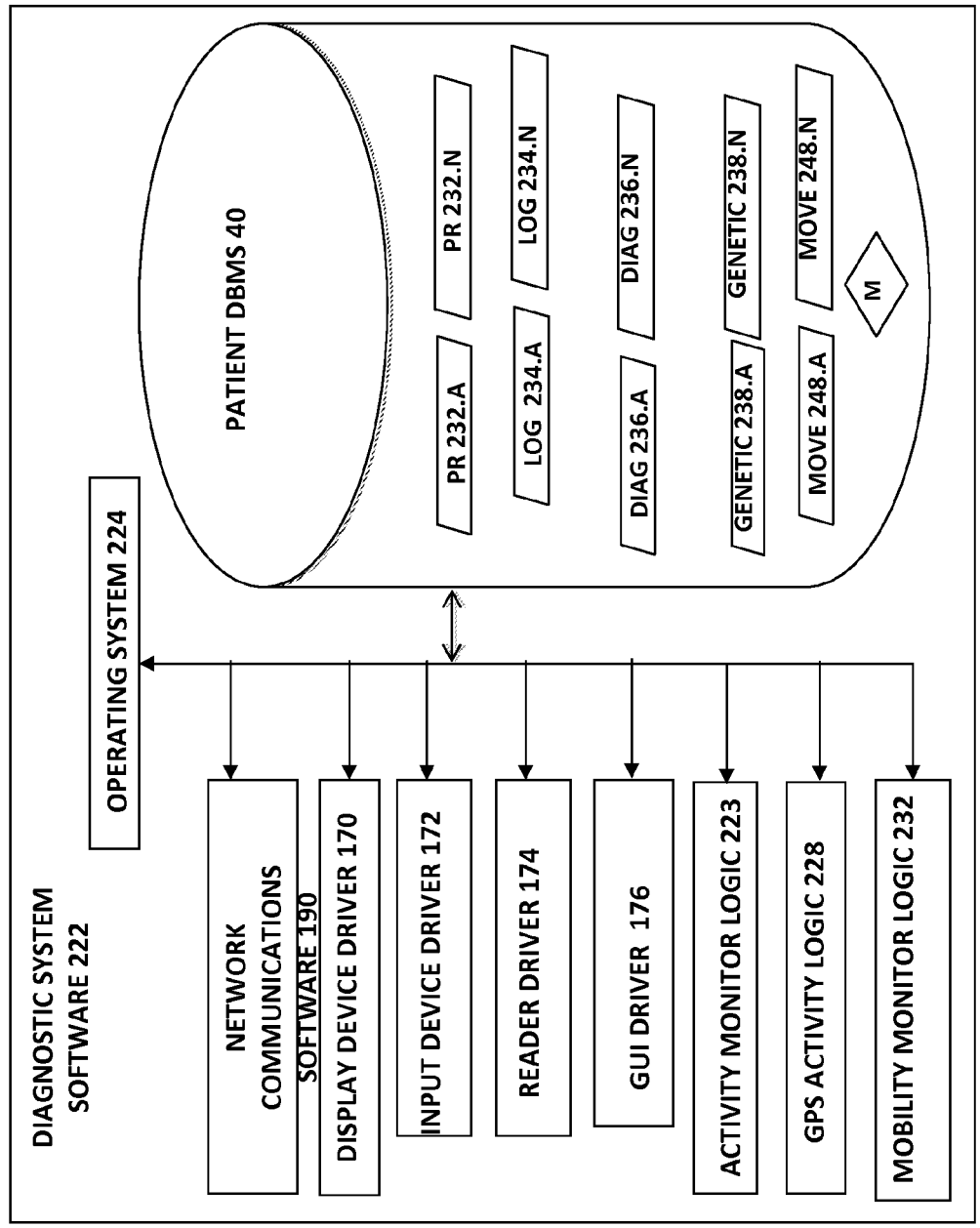
FIG. 36 is a schematic illustrating the diagnostic system software as containing patient records, diagnostic records and genetic records.

FIG. 36 is a schematic illustrating the diagnostic system software 222 as containing the patient records 232.A-232.N, the patient activity logs 234.A-234.N, the diagnostic records 236.A-236.N and the genetic records 238.A-238.N.

Figure 37:
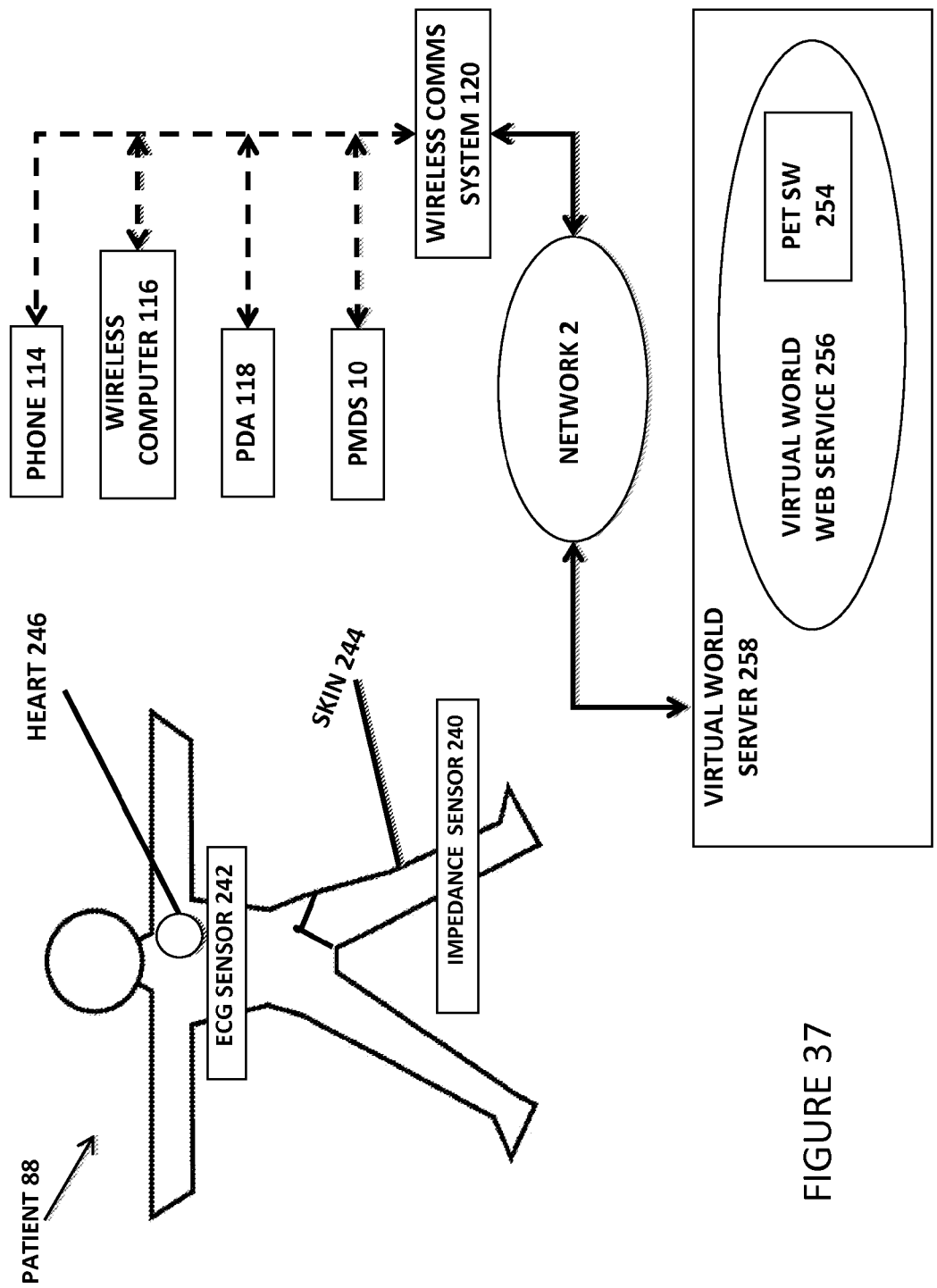
FIG. 37 is a schematic of the patient of FIG. 12 being monitored by additional sensors.

FIG. 37 is a schematic of the patient 88 being monitored by additional sensors 240 and 242. An impedance sensor 240 is in contact with a second skin area 244 of the patient. The impedance sensor 240 is configured and positioned to detect variations in dermal impedance of the patient 88 that are generally determined by sweat forming on the second skin area 244. An electrocardiograph sensor 242 (or "ECG sensor" 242) is configured and positioned relative to the patient 88 to measure the electrical activity of the heart 246 of the patient 88.

Figure 38:
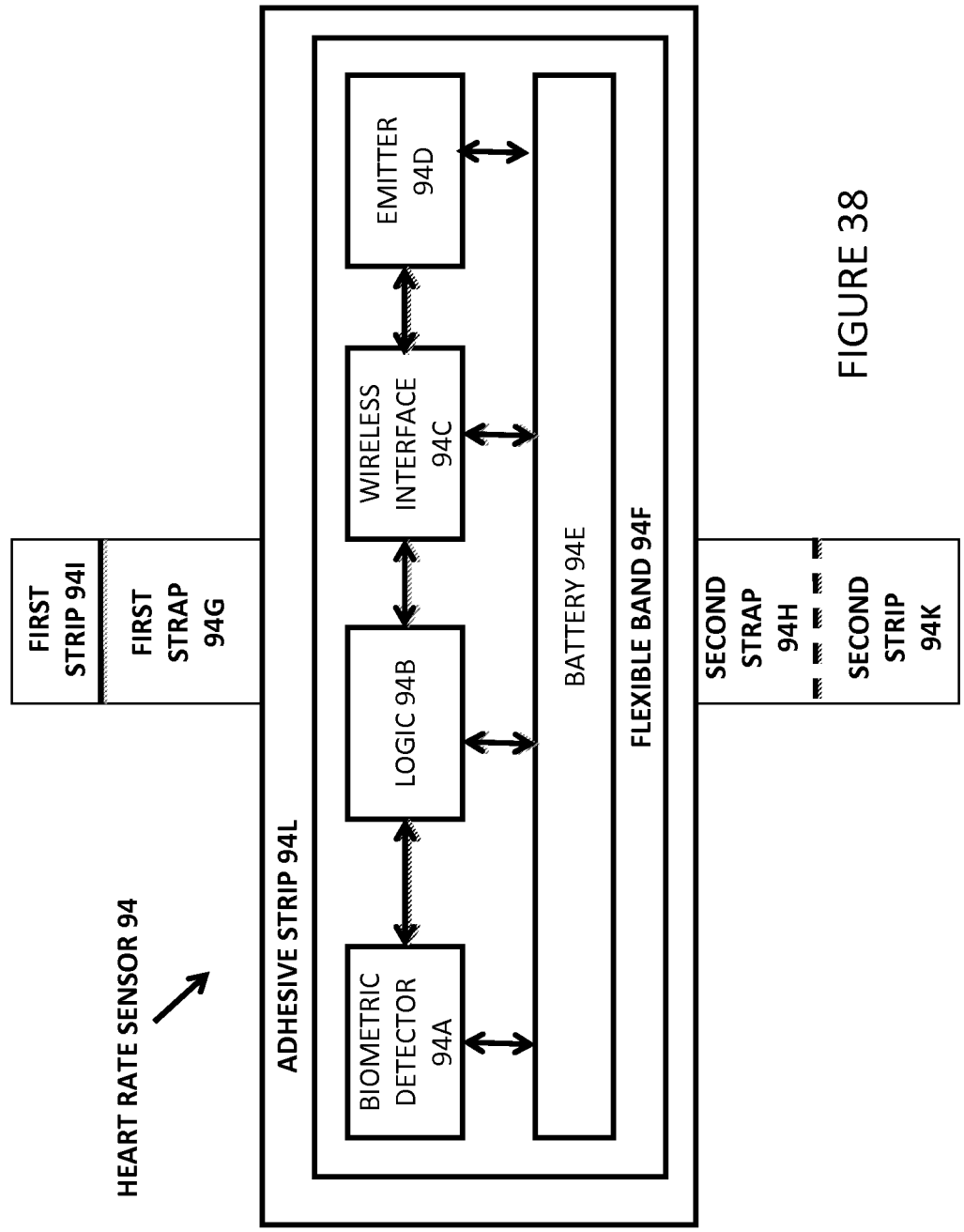
FIG. 38 is a schematic diagram of the exemplary heart rate sensor of FIG. 12.

FIG. 38 is a schematic diagram of the exemplary heart rate sensor 94. The heart rate sensor 94 includes a biometric detector 94A, a logic circuit 94B, a wireless interface 94C, a signal emitter 94D, and a battery 94E that are all mounted onto a flexible band 94F. The biometric sensor 94A monitors and measures the heart rate of the patient 88 and communicates the heart rate measurement to the logic circuit 94B. The logic circuit 94B formats and populates a biometric data message and directs the wireless interface 94C to transmit the biometric message in a wireless transmission via the emitter 94D. It is understood that the emitter 94D may be a radio wave antenna or a light pulse emitter. The emitter 94D is configured to transmit the biometric message for successful reception by the phone 114, the wireless computer 116, the PDA 118 and/or the wireless comms system 120. The battery 94E provides electrical power to the biometric detector 94A, the logic circuit 94B, the wireless interface 94C and the signal emitter 94D.

A first strap 94G and a second strap 94H are each separately coupled with the flexible band and enable the heart rate sensor to be detachably coupled to the patient 88. A first hook and loop fabric strip 941 and a second hook and loop fabric strip are positioned to detachably engage and hold the flexible band 94E against a skin area 163 and 176 of the patient 88. Alternatively or additionally an adhesive strip 94L of the flexible band 94F is configured and positioned to enable detachable placement of the flexible band against a skin area 163 and 164 of the patient 88.

It is understood that the illustration of the heart sensor 94 of FIG. 37 is exemplary and is descriptive in part of other sensors 20-23, 94, 98, 102, 240 and 242.

Figure 39:
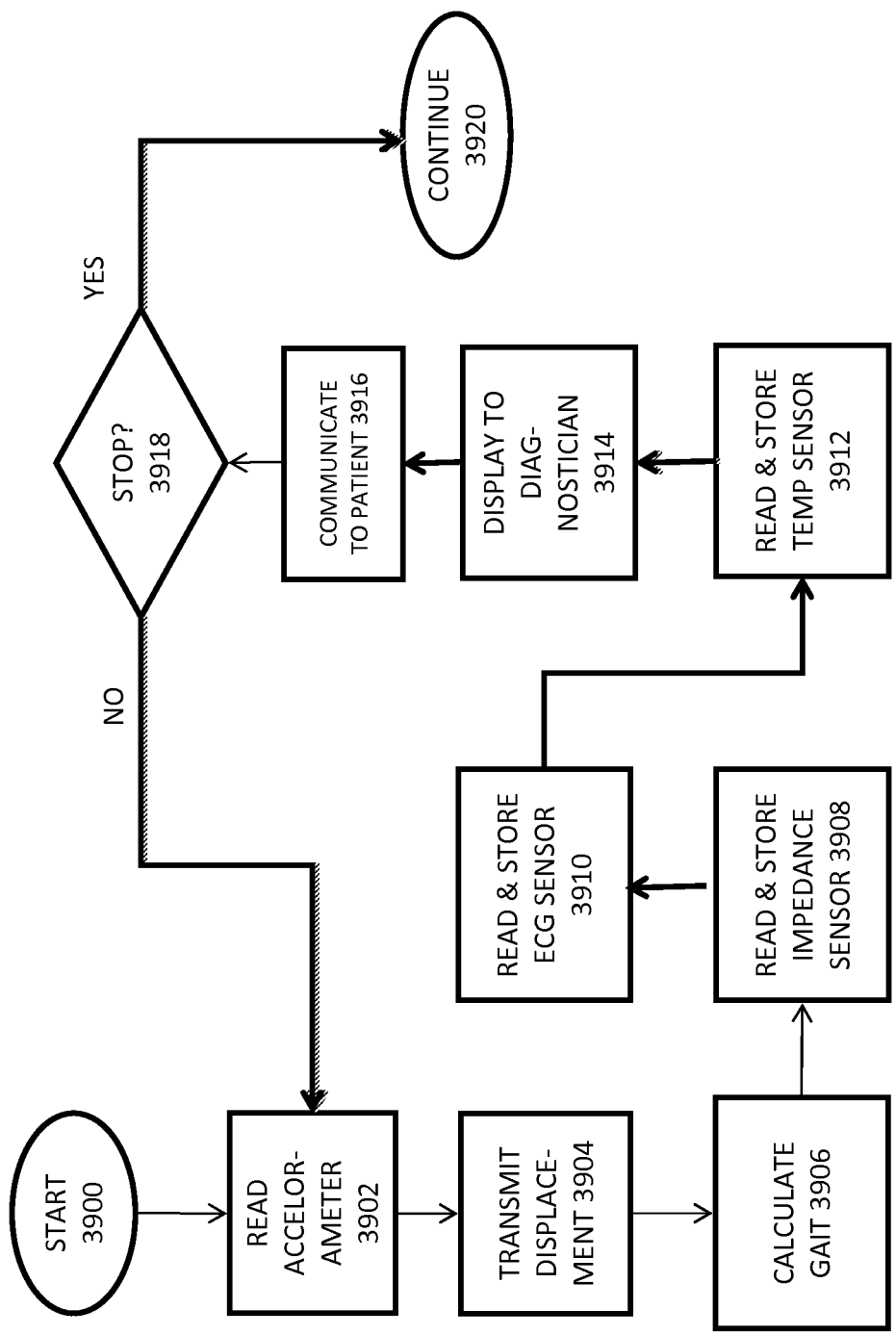
FIG. 39 illustrates another still additional or alternate method, wherein a diagnostician receives and analyzes information and advises the patient of FIGS. 12-15 and 37 with therapeutic guidance.

Referring now generally to the Figures and particularly to FIG. 39, FIG. 39 illustrates another still additional or alternate method, wherein the diagnostician receives and analyzes information and advises the patient 88 with therapeutic guidance. In step 3902 the phone 114 receives accelerometer data from the accelerometer 170. The phone 114 transmits the received accelerometer data to the diagnostic system 110 in step 3904, wherein the accelerometer data is stored in a movement record 248.A-248.N. The diagnostic system 110 calculates a walking gait of the patient 88 by analyzing a plurality of movement records 248.A-248.N and stores the gait calculation in step 3906. The phone 114 receives skin impedance data from the impedance sensor 240 and transmits the received impedance data to the diagnostic system 110 in step 3908. The phone 114 receives electrocardiograph data from the ECG sensor 242 and transmits the received electrocardiograph data to the diagnostic system 110 in step 3910. The phone 114 receives body temperature data from the temperature sensor 98 and transmits the received body temperature data to the diagnostic system 110 in step 3912.

The diagnostic system 110 displays the gait calculated and the data received in steps 3904, and 3908-3912 to the diagnostician in step 3914 on the display screen 128 as rendered by the GUI driver 176. The diagnostician analyzes the displayed information and communicates diagnostic information, prognostic information, and therapeutic guidance to the patient in step 3916 via the network 2.

The diagnostician determines in step 3918 whether to continue the loop of steps 3902 through 3918 or to proceed on to alternate activities of step 3920.

Figure 40:
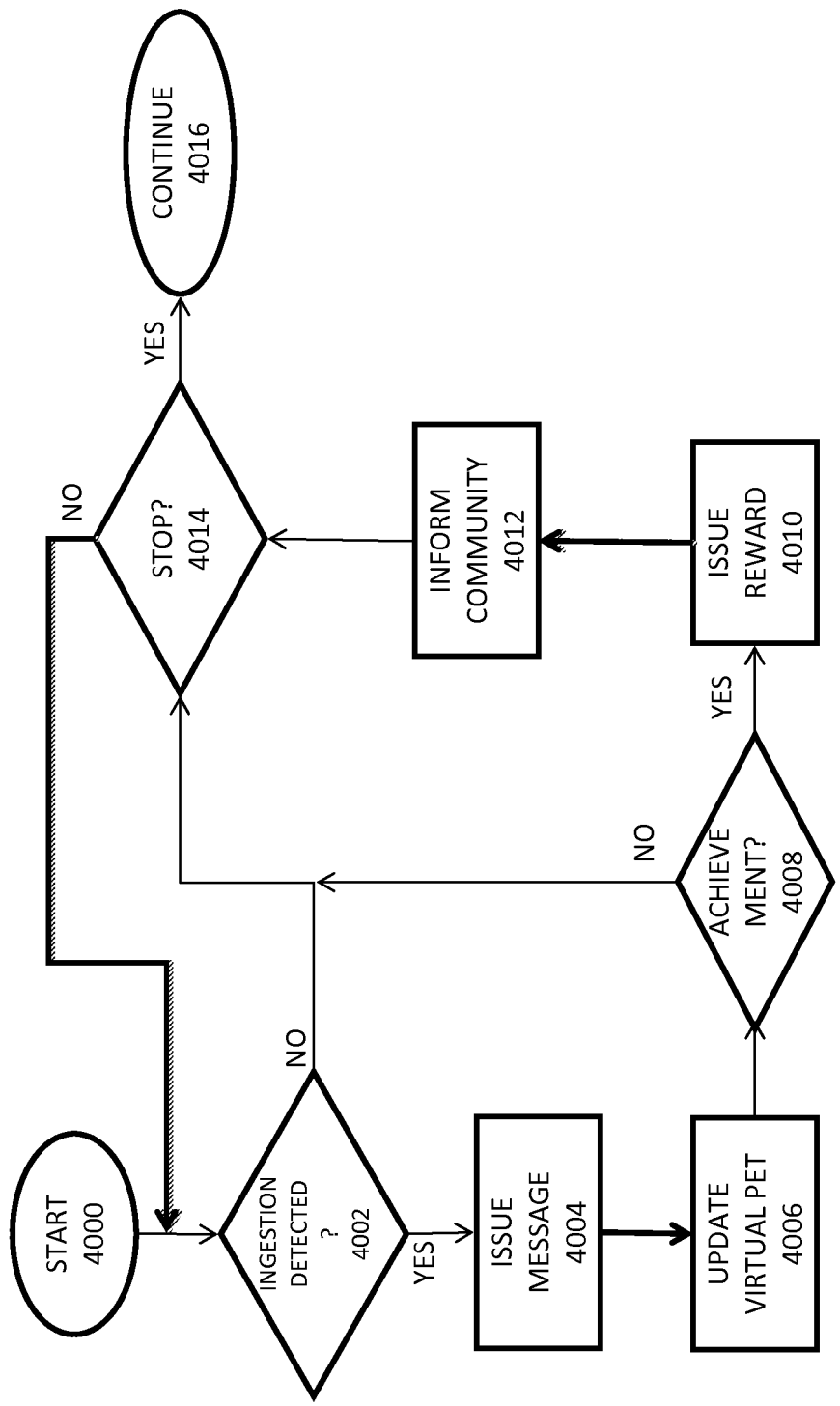
FIG. 40 illustrates another even additional or alternate method, wherein the patient of FIGS. 12 and 37 is encouraged by yet other engagement modalities to adhere to a prescribed ingestion of the medicine of FIG. 12.

Referring now generally to the Figures and particularly to FIGS. 22 and 40, FIG. 40 illustrates another even additional aspect of a method, wherein the patient is encouraged by yet other engagement modalities to adhere to a prescribed ingestion of the medicine 126. In step 4002 the phone 114 determines whether the IEMD 4 has emitted an ingestion signal. When the phone 114 determines in step 4002 that the IEMD 4 has emitted an ingestion signal, the phone 114 informs the DB computer 108 via the network 2 in step 4004 an ingestion signal has been received. The DB computer 108 then updates a virtual pet status in step 4006 in accordance with the information transmitted in step 4004. The virtual pet status is an aspect of a virtual pet personality software 254 is maintained by a virtual world web service 256 that is hosted on a virtual world services server 258. The virtual world services server 258 is accessible to the phone 114 through the network 2, and the virtual pet personality software 254 maintains status and conditions on the basis of instructions from the virtual world web service 256 and from the patient 88 and the DB computer 108 as delivered via the network 2 to the virtual world services server 256.

The DB computer 108 further determines in step 4008 whether with the information transmitted in step 4004 in combination with additional information related to the patient and stored in the patient data base 40 indicates that the patient 88 has earned a reward or achieved a new reward state or level. When the DB computer 108 determines in step 4008 that the patient 88 has earned a reward, the reward is issued in step 4010. The reward of step 4010 may be as modest as directing the phone 114 to vibrate, visually display a congratulations message, and/or render a pleasant audible tone or musical tune. The reward of step 4010 may also include making provisions for delivery of a physical coin, medallion, or crystal. The reward of step 4010 may alternatively or additionally include (a.) providing the patient 88 with a ringtone data or file; (b.) rewarding the patient 88 with a music download service at no extra charge; and/or (c.) a delivery of a hard copy note of congratulations. In various aspects, the rewards may be provided by, or otherwise associated with, one or more reward/incentive sources. Such sources may include, for example, proprietary reward systems, e.g., developed in conjunction with or for aspects of the invention, and existing reward systems, e.g., commercial incentive or reward systems such as point systems, coupon systems, etc., associated with one or more independent providers.

In optional step 4012 the DB computer 108 informs an online community of the achievement and/or status of the patient 88 via the network 2. The DB computer 108 in step 4014 whether to continue the loop of steps 4002 through 4014 or to proceed on to perform alternate computational activities of step 4016.

Figure 41:
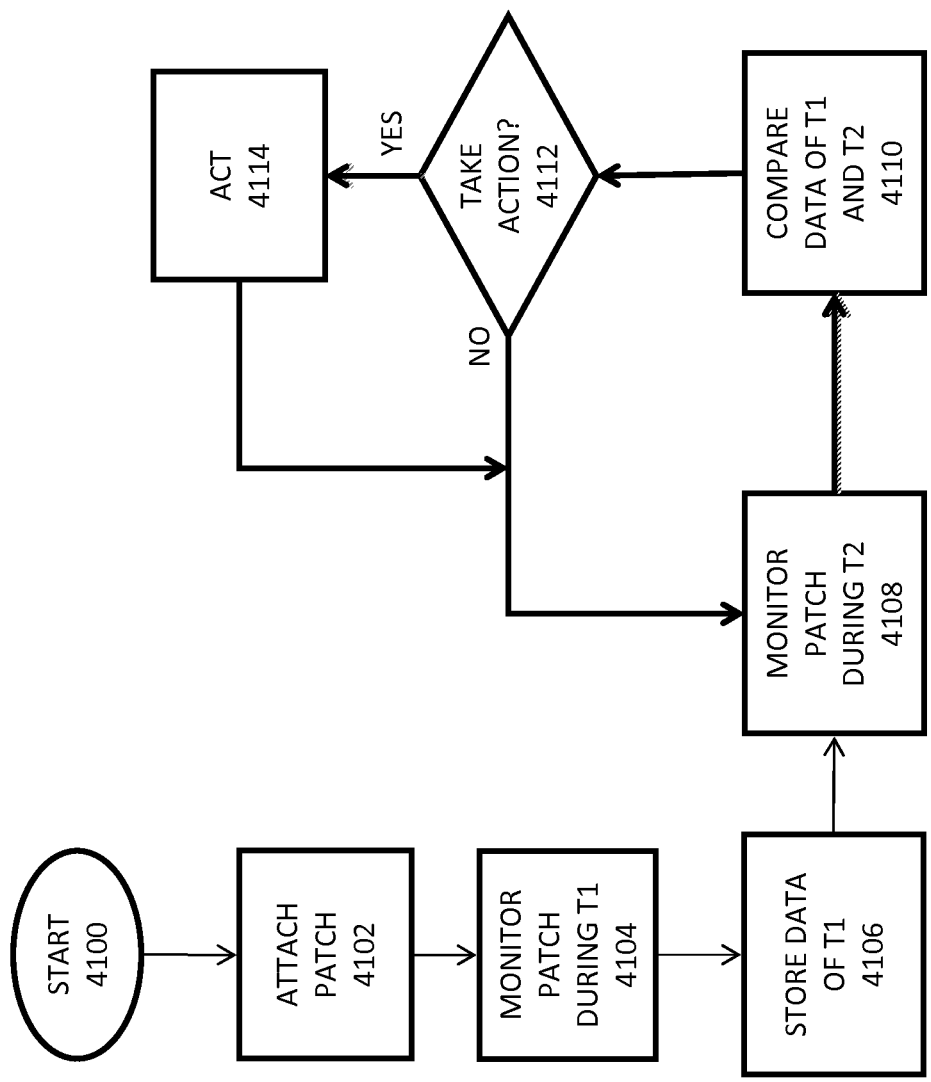
FIG. 41 illustrates another even additional process wherein the patch receiver of FIG. 12 is attached or coupled to the patient of FIG. 12 and monitored over two separate time periods.

Referring now generally to the Figures and particularly to FIG. 41, FIG. 41 illustrates another even additional process wherein the patch receiver 122 is attached or coupled to the patient 88, or clothing or personal equipment of the patient 88 in step 4102. The biometric data received by the patch receiver 122 is monitored during a first time period T1 in step 4104. The biometric data received in step 4104 is stored in the patient database 40 in step 4106. The biometric data received by the receiver patch 122 is then monitored during a second time period T2 in step 4108. In step 4110 the biometric data received by the path receiver 122 e.g., from the one or more IEMD 4, during the first time period T1 and second time period T2 is compared by a diagnostician and/or the activity monitor logic 223. The diagnostician and/or the activity monitor logic 223 then determines in step 4112 whether a predetermined action shall be taken at least partly on the basis of the comparison of step 4112 of the behavior of the one or more IEMD 4 that transmit an ingestible event marker datum IEM M during the first time period T1 and the second time period T2. The predetermined action, such as transmitting an alert to the patient 88 via the cellular telephone 114 or informing a healthcare provider of the state of the patient 88, is affected in step 4114.

Figure 42:
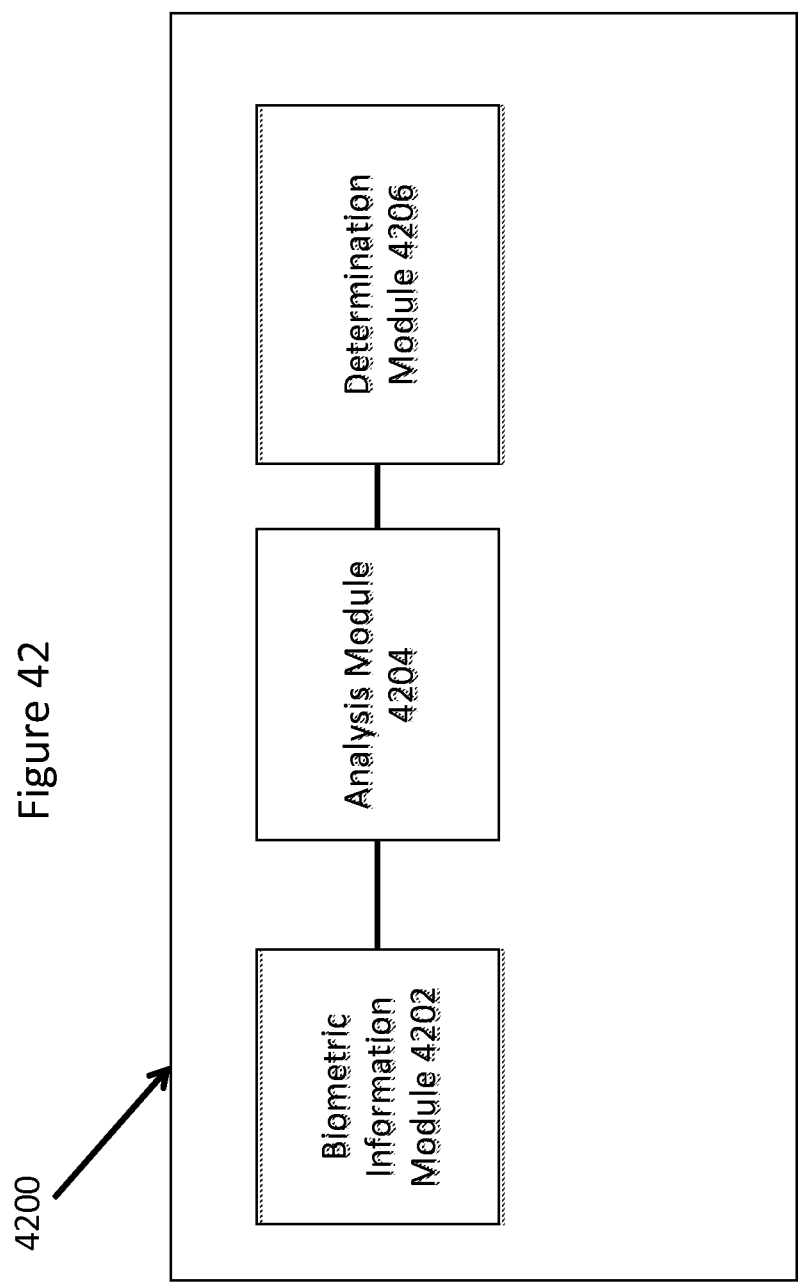
FIG. 42 illustrates a system to facilitate adherence to a treatment plan.

In various aspects, a system is provided, for example and as illustrated in FIG. 42, a system 4200 may include a biometric information module 4202 to receive biometric information associated with an ingestible event marker datum IEM M; an analysis module 4204 to analyze the biometric information; and a determination module 4206 to determine a therapeutic recommendation at least partly on the basis of the analysis. Biometric information includes any data and/or information associated with living being, e.g., physiologic information such as heart rate, blood pressure, etc.; subA skilled artisan will recognize that the modules may be standalone or integrated in various combinations. Further, one or more modules may be implemented as software modules, as hardware, as circuitry, etc.

Figure 43:
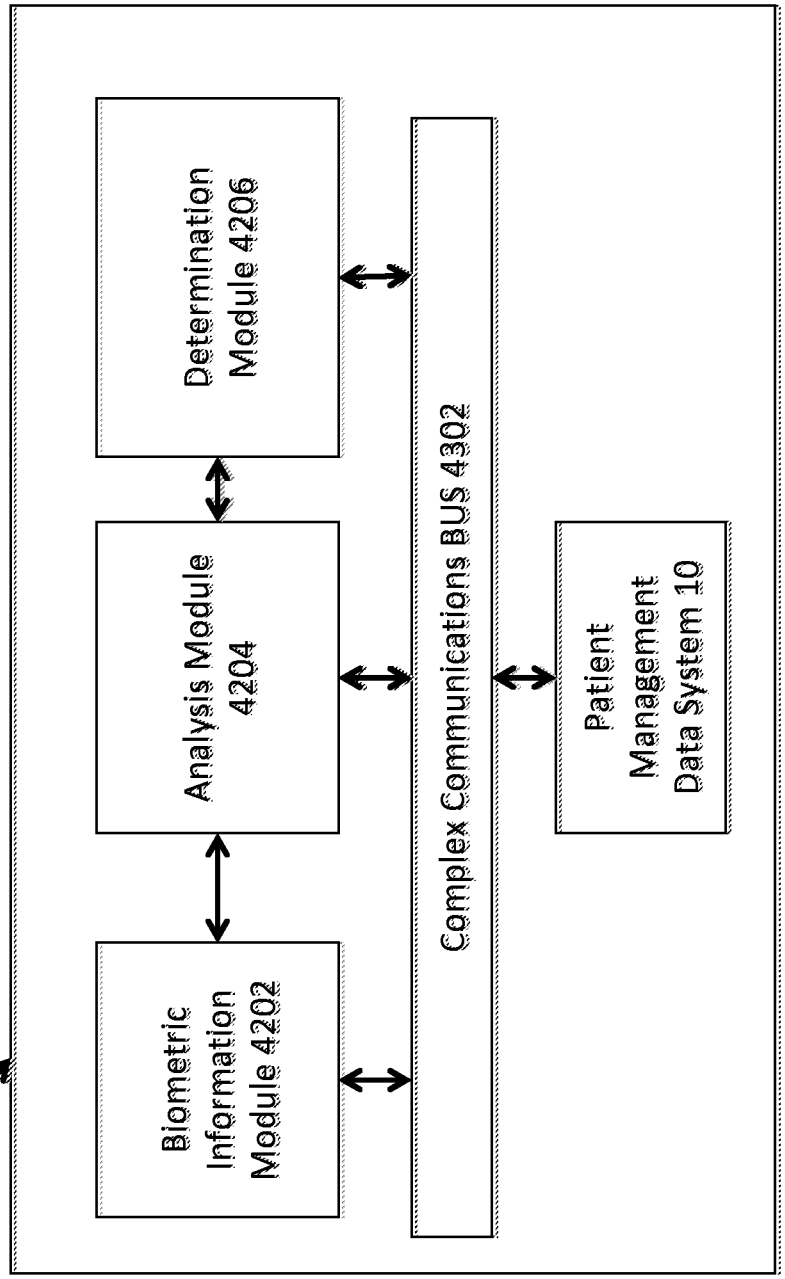
FIG. 43 illustrates a system to facilitate adherence to a treatment plan including a patient management system communicatively coupled with all other parts via a communications bus.

FIG. 43 illustrates a unified system 4300 to facilitate adherence to a treatment plan which may include a biometric information module 4202 to receive biometric information associated or contained within an ingestible event marker datum IEM M; an analysis module 4204 to analyze the biometric information; and the determination module 4206 to determine a therapeutic recommendation at least partly on the basis of the analysis. The patient management data system 10 is optionally comprised within the unified system 4300 and may be communicatively coupled with all other parts of the unified system 4300 via a communications bus 4302. Further, one or more modules 4202, 4204, 4206 and PMDS 10 may be implemented as software modules, as hardware, as circuitry, etc. Referring now to FIG. 2, in certain alternate configurations, the unified system 4300 may be, in whole or in part, comprised within the PMDS 10.

In addition, one or more modules may be associated with one or more devices. To illustrate, a receiver or computer may be associated with the biometric information module 4202 of the unified system 4300. One or more modules 4202, 4202, 4206 and PMDS 10 may be associated with a computer, a network, the internet 2B, the telephony network 2A, a database computer 108, a database 40, an ingestible event device IEMD 4, an ingestible event marker datum IEM M, a receiver, e.g., a receiver associated with an IEMD 4 or other device, a wireless computer 116; a temperature sensor, a respiration sensor, a pressure sensor, a heart sensor, and/or other devices and systems.

While the present invention has been described with reference to specific methods, devices and systems, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The foregoing disclosures and statements are illustrative only of the present invention, and are not intended to limit or define the scope of the present invention. The above description is intended to be illustrative, and not restrictive. Although the examples given include many specificities, they are intended as illustrative and not limiting. Those skilled in the art will appreciate that various adaptations and modifications of the just-described systems and methods can be configured without departing from the scope and spirit of the present invention. Therefore, it is to be understood that the present invention may be practiced other than as specifically described herein. The scope of the present invention as disclosed and claimed should, therefore, be determined with reference to the knowledge of one skilled in the art and in light of the disclosures presented above.

What is claimed is:

1. A system, comprising:
    an ingestible event marker (IEM) configured to generate ingestion information and to emit the ingestion information conductively via an in-body data transmission upon contact with bodily fluid at a target physiological site, the IEM comprising:
        first and second electrodes formed of dissimilar materials configured to generate a voltage to energize the IEM when the first and second electrodes contact the bodily fluid;
    a first sensor configured to be coupled to a body of a patient and to detect first vital parameter data from the body of the patient;
    a second sensor positionable remotely from the body of the patient, wherein the second sensor is configured to detect second vital parameter data by sensing environmental information associated with the body of the patient;
a receiver configured to be electrically coupled to an exterior surface of the body of the patient, wherein the receiver comprises a transceiver to receive the ingestion information conductively via the in-body data transmission from the IEM, the first vital parameter data from the first sensor, and the second vital parameter data from the second sensor; and
a patient management data system (PMDS) communicatively coupled to the transceiver, wherein the PMDS comprises:
a patient database, comprising:
a patient record associated with the patient, wherein the patient record indicates:
patient activity data, comprising:
expected activities reported by the patient, wherein each of the expected activities is associated with an expected time to engage in the respective expected activities; and
patient history data, comprising:
detected first vital parameter data received via the transceiver from the first sensor; and
detected second vital parameter data received via the transceiver from the second sensor; and
an analysis module, configured to:
compare at least one of:
the detected first vital parameter data to a first range of healthy values associated with the first vital parameter to identify an unhealthy first vital parameter value; or
the detected second vital parameter data to a second range of healthy values associated with the second vital parameter to identify an unhealthy second vital parameter value;
correlate at least one of an identified unhealthy first vital parameter value or an identified unhealthy second vital parameter value to an expected activity of the patient activity data; and
select a therapeutic recommendation to at least one of:
bring the identified unhealthy first vital parameter value within the first range of healthy values; or
bring the identified unhealthy second vital parameter value within the second range of healthy values;
wherein the PMDS is further configured to:
transmit the selected therapeutic recommendation to the patient, via the transceiver, at a prospective expected time associated with the correlated expected activity.

2. The system of claim 1, wherein the patient record further indicates prescription information including a medication prescribed to the patient, wherein the prescribed medication is associated with a medication schedule including prescribed times to administer the medication;
wherein the patient history data further comprises:
ingestion information received via the transceiver from one or more than one IEM ingested by the patient, wherein the one or more than one IEM ingested by the patient comprise the medication; and
attestation information reported by the patient, wherein the attestation information comprises an attestation associated with at least one administered medication; and wherein the analysis module is further configured to:
determine, based on at least one of the ingestion information or the attestation information, that the prescribed medication has not been administered at a prescribed time of the medication schedule that has passed; and
transmit to the transceiver, after a designated time period since the passed prescribed time, a message to remind the patient to administer the prescribed medication.

3. The system of claim 1, wherein the patient record further indicates prescription information including a behavior prescribed to the patient, wherein the prescribed behavior is associated with a behavior schedule including prescribed times to perform or to avoid the behavior;
wherein the patient history data further comprises:
attestation information reported by the patient, wherein the attestation information comprises an attestation associated with at least one of a behavior performed or a behavior avoided; and
wherein the analysis module is further configured to:
determine, based on the attestation information, that the prescribed behavior has not been attested to at a prescribed time of the behavior schedule that has passed; and
transmit to the transceiver, after a designated time period since the passed prescribed time, a message to remind the patient to perform or to avoid the prescribed behavior.

4. The system of claim 1, wherein the receiver comprises a communication device to communicate the selected therapeutic recommendation to the patient.

5. The system of claim 4, wherein the communication device is selected from the group consisting essentially of a telephone, a cellular telephone, a computer, a personal digital assistant, and a network appliance.

6. The system of claim 1, wherein the therapeutic recommendation is further selected based at least partly on genetic information descriptive of the patient.

7. The system of claim 1, wherein the therapeutic recommendation is further selected based at least partly on biometric information in view of additional patient information.

8. The system of claim 7, wherein the additional patient information is selected from the group consisting essentially of lifestyle data, patient adherence information, behavioral information, emotional information and diagnostic test information.

9. The system of claim 1, wherein the therapeutic recommendation is selected from the group consisting essentially of a medicine prescription adjustment, a meditation practice, a relaxation practice, a physical exercise, a period of sleep, a procedural change, a therapy change and a dietary adjustment.

10. The system of claim 1, further comprising a motion detector configured to be coupled to the patient and to generate a patient motion datum, and wherein the therapeutic recommendation is further selected based at least partly on the patient motion datum.

11. The system of claim 10, wherein the motion detector is selected from the group consisting essentially of a cellular telephone, an accelerometer and a global positioning signal device.

12. The system of claim 1, further comprising:
a vital parameter monitor to monitor a health parameter of the patient, wherein the vital parameter monitor is communicatively coupled with the PMDS.

13. The system of claim 12, wherein the vital parameter monitor is selected from the group consisting essentially of a heart rate monitor, a blood pressure monitor, a respiration monitor, and a patient skin electrical current conductivity monitor.

14. The system of claim 1, further comprising a patient data input module to receive information from the patient, wherein the patient data input module is communicatively coupled with the PMDS.

15. The system of claim 14, wherein the patient data input module is bi-directionally communicatively coupled with the PMDS.

16. The system of claim 14, wherein the patient data input module is selected from the group consisting essentially of a telephone, a cellular telephone, a computer, a personal digital assistant, a network appliance, and an audio recorder.

17. The system of claim 1, wherein the PMDS stores at least one selectable therapeutic recommendation.

18. The system of claim 1, further comprising a motion detector to detect and to report movement of the patient to the PMDS.

19. The system of claim 1, wherein the PMDS is communicatively coupled with an electronic communications network, and wherein the selected therapeutic recommendation is transmitted via the electronic communications network.

20. The system of claim 1, wherein the target physiological site is a digestive tract internal target site.

21. The system of claim 1, wherein the environmental information associated with the body of the patient comprises sound detection information, air pressure variation information, light energy reflection information, heat detection information, or any combination thereof.

22. The system of claim 1, wherein the first vital parameter data comprises at least one of a heart rate, a blood pressure, a respiration rate, a respiration intensity, or electrical skin conductivity.

23. The system of claim 22, wherein the second vital parameter data comprises at least one of a heart rate, a blood pressure, a respiration rate, a respiration intensity, or electrical skin conductivity.

* * * * *